(12) United States Patent
Alferiev et al.

(10) Patent No.: US 8,263,127 B2
(45) Date of Patent: Sep. 11, 2012

(54) PHOTOCHEMICAL ACTIVATION OF SURFACES FOR ATTACHING BIOMATERIAL

(75) Inventors: Ivan Alferiev, Clementon, NJ (US); Ilia Fishbein, Philadelphia, PA (US); Michael Chorny, Philadelphia, PA (US); Robert J. Levy, Merion Station, PA (US); Benjamin Yellen, Durham, PA (US); Darryl Williams, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 11 days.

(21) Appl. No.: 12/633,593

(22) Filed: Dec. 8, 2009

(65) Prior Publication Data

US 2010/0210015 A1 Aug. 19, 2010

Related U.S. Application Data

(60) Division of application No. 11/250,877, filed on Oct. 14, 2005, now Pat. No. 7,635,734, which is a continuation-in-part of application No. PCT/US2004/011861, filed on Apr. 16, 2004.

(60) Provisional application No. 60/691,416, filed on Jun. 17, 2005, provisional application No. 60/545,127, filed on Feb. 17, 2004.

(51) Int. Cl.
*A61K 9/14* (2006.01)
*A61K 47/48* (2006.01)

(52) U.S. Cl. ........................ 424/484; 525/54.1
(58) Field of Classification Search ........................ None
See application file for complete search history.

(56) References Cited

U.S. PATENT DOCUMENTS

| 5,002,582 | A | * | 3/1991 | Guire et al. ............ 427/2.24 |
| 5,916,539 | A | | 6/1999 | Pilgrimm |
| 5,921,244 | A | | 7/1999 | Chen et al. |
| 5,942,555 | A | | 8/1999 | Swanson et al. |

(Continued)

FOREIGN PATENT DOCUMENTS

WO WO 02/072172 9/2002

(Continued)

OTHER PUBLICATIONS http://www.rsc.org/chemsoc/visualelements/pages/data/intro_groupiv_data.html, accessed May 31, 2011.*

(Continued)

*Primary Examiner* — Paul Dickinson
(74) *Attorney, Agent, or Firm* — RatnerPrestia

(57) ABSTRACT

A water-soluble photo-activatable polymer including: a photo-activatable group adapted to be activated by an irradiation source and to form a covalent bond between the water-soluble photo-activatable polymer and a matrix having at least one carbon; a reactive group adapted to covalently react with a biomaterial for subsequent delivery of the biomaterial to a cell; a hydrophilic group; and a polymer precursor. A composition including a monomolecular layer of the water-soluble photo-activatable polymer and a matrix having at least one carbon, wherein the monomolecular layer is covalently attached to the matrix by a covalent bond between the photo-activatable group and the at least one carbon. The composition further includes a biomaterial having a plurality of active groups, wherein the biomaterial is covalently attached to the monomolecular layer by covalent bonding between the active groups and reactive groups. Also provided is a method for delivery of a biomaterial to a cell.

45 Claims, 50 Drawing Sheets

U.S. PATENT DOCUMENTS

| | | | |
|---|---|---|---|
| 7,635,734 B2* | 12/2009 | Alferiev et al. | 525/54.1 |
| 2001/0014448 A1* | 8/2001 | Chappa et al. | 435/6 |
| 2002/0076443 A1 | 6/2002 | Stein et al. | |
| 2002/0133225 A1 | 9/2002 | Gordon | |
| 2005/0100675 A1 | 5/2005 | Mao et al. | |
| 2006/0147847 A1 | 7/2006 | Guire et al. | |

FOREIGN PATENT DOCUMENTS

| | | |
|---|---|---|
| WO | WO 2004/093643 | 11/2004 |
| WO | WO 2005/110395 | 11/2005 |
| WO | WO 2006/039675 | 4/2006 |

OTHER PUBLICATIONS http://www.coleparmer.com/TechLibraryArticle/827, accessed Dec. 22, 2011.*

Christian Plank, Ulrike Schillinger, Franz Acherer, Christian Bergemann, Jean-Serge Remy, Florian Krotz, Martina Anton, Jim Lausier and Joseph Rosenecker, The Magnetofection Method: Using Magnetic Force to Enhance Gene Delivery, May 2003, Biol. Chem., vol. 384, pp. 737-747, Walter de Gruyter, Berlin, New York.

Florian Krotz, Cor De Wit, Hae-Young Sohn, Stefan Zahler, Torsten Gloe, Ulrich Pohl and Christian Plank, Magnetofection-A Highly Efficient Tool for Antisense Oligonucleotide Delivery in Vitro and In Vivo, May 2003, Molecular Therapy, vol. 7, pp. 700-710, No. 5, The American Society of Gene Therapy.

M. Laird Forrest, James T. Koerber, and Daniel W. Pack, A Degradable Polyethylenimine Derivative with Low Toxicity for Highly Efficient Gene Delivery, Bioconjugate Chem., 2003, pp. 934-940, vol. 14, American Chemical Society.

Michael A. Gosselin, Wenjin Guo, and Robert J. Lee, Efficient Gene Transfer Using Reversibly Cross-Linked Low Molecular Weight Polyethylenimine, Bioconjugate Chem., 2001, pp. 989-994, vol. 12, American Chemical Society.

J. L. Arias, V. Gallardo, S. A. Gomez-Lopera, R. C. Plaza, and A. V. Delgado, Synthesis and Characterization of Poly(ethyl-2-cyanoacrylate) Nanoparticles with a Magnetic Core, Oct. 10, 2001, pp. 309-321, vol. 77, Journal of Controlled Release, Elsevier Science B.V.

S. A. Gomez-Lopera, R. C. Plaza, and A. V. Delgado, Synthesis and Characterization of Spherical Magnetite/Biodegradable Polymer Composite Particles, 2001, pp. 40-47, vol. 240, Journal of Colloid and Interface Science, Academic Press.

M. Igartua, P. Saulnier, B. Heurtault, B. Pech, J. E. Proust, J. L. Pedraz, and J. P. Benoit, Development and Characterization of Solid Lipid Nanoparticles Loaded with Magnetite, 2002, pp. 149-157, vol. 233, International Journal of Pharmaceutics, Elsevier Science B.V.

R. H. Muller, S. Maaben, H. Weyhers, F. Specht, and J. S. Lucks, Cytotoxicity of Magnetite-Loaded Polylactide, polylactide/Glycolide Particles and Solid Lipid Nanoparticles, 1996, pp. 85-94, vol. 138, International Journal of Pharmaceutics, Elsevier Science B.V.

Ernst Wagner, Kurt Zatloukal, Matt Cotton, Helen Kirlappos, Karl Machtler, David T. Curiel, and Max L. Birnstiel, Jul. 1992, pp. 6099-6103, vol. 89, Proc. Natl. Acad. Sci., USA.

Christian Plank, Franz Scherer, Ulrike Schillinger, Christian Bergemann, and Martina Anton, Magnetofection: Enhancing and Targeting Gene Delivery with Superparamagnetic Nanoparticles and Magnetic Fields, 2003, pp. 29-32, vol. 13, No. 1, Journal of Liposome Research, Marcel Dekker, Inc.

F. Scherer, M. Anton, U. Schillinger, J. Henke, C. Bergemann, A. Kruger, B. Gansbacher, and C. Plank, Magnetofection: enhancing and targeting gene delivery by magnetic force in vitro and in vivo, 2002, pp. 102-109, vol. 9, Gene Therapy, Nature Publishing Group.

Florian Krotz, Hae-Young Sohn, Torsten Gloe, Christian Plank, and Ulrich Pohl, Magnetofection Potentiates Gene Delivery to Culture Endothelial Cells, 2003, pp. 425-434, vol. 40, S. Karger AG, Basel.

M. De Cuyper, and M. Joniau, Magnetoliposomes Formation and Structural Characterizations, 1988, pp. 311-319, European Biophysics Journal, Springer-Verlag.

Sanaa E. Khalafalla, Magnetic Fluid, Chemtech, Sep. 1975, pp. 540-546.

Majeti N. V. Ravi Kumar, Nano and Microparticles as Controlled Drug Delivery Devices, 2000, pp. 234-258, vol. 3, No. 2, J Pharm Pharmaceut Sci.

David Quintanar-Guerrero, Eric Allemann, Hatem Fessi, and Eric Doelker, 1998, pp. 1113-1128, vol. 24, No. 12, Drug Development of Industrial Pharmacy, Marcel Dekker, Inc.

Isabelle Messai, Severine Munier, Yasemin Ataman-Onal, Bernard Verrier, and Thierry Delair, Elaboration of Poly(ethyleneimine) Coated Poly(D,L-lactic acid) Particles. Effect of Ionic Strength on the Surface Properties and DNA Binding Capabilities, 2003, pp. 293-305, vol. 32, Colloids and Surfaces B: Biointerfaces, Elsevier B.V.

Taeghwan Hyeon, Chemical Synthesis of Magnetic Nanoparticles, 2003, pp. 927-934, Chem Comm, The Royal Society of Chemistry.

MM OW Sullivan, JJ Green, and TM Przybycien, Development of a Novel Gene Delivery Scaffold Utilizing Colloidal Gold-Polyethylenimine Conjugates for DNA Condensation, 2003, pp. 1882-1890, vol. 10, Gene Therapy, Nature Publishing Group.

Ritsuko Ito, Yoshiharu Machida, Takanori Sannan, and Tsuneji Nagai, Magnetic Granules: a novel system for specific drug delivery to esophageal mucosa in oral administration, 1990, pp. 109-117, vol. 61, International Journal of Pharmaceutics, Elsevier Science Publishers B.V. (Biomedical Division).

Christian Plank, Martina Anton, Carsten Rudolph, Joseph Rosnecker & Florian Krotz, Enhancing and targeting nucleic acid delivery by magnetic force, 2003, pp. 745-758, vol. 3, No. 5, Expert Opinion Biol. Ther., Ashley Publications Ltd.

Zachary G. Forbes, Benjamin B. Yellen, Kenneth A. Barbee, and Gary Friedman, An Approach to Targeted Drug Delivery Based on Uniform Magnetic Fields, Sep. 2003, pp. 3372-3377, vol. 39, No. 5, IEEE Transactions on Magnetics.

Janet Fricker, Drug-eluting stents: flashy future or flash-in-the-pan?, Nov. 2001, pp. 1135-1137, vol. 6, No. 22, Drug Discovery Today, Elsevier Science Ltd.

Samer M. Garas, Philip Huber, and Neal A. Scott, Overview of therapies for prevention of restenosis after coronary interventions, 2001, pp. 165-178, vol. 92, Pharmacology & Therapeutics, Elsevier Science Inc.

A. H. Gershlick, Treating atherosclerosis: local drug delivery from laboratory studies to clinical trials, 2002, pp. 259-271, vol. 160, Atherosclerosis, Elsevier Science Ireland, Ltd.

Scott Goodwin, Caryn Peterson, Carl Hoh, and Craig Bittner, Targeting and retention of magnetic targeted carriers (MTCs) enhancing intra-arterial chemotherapy, 1999, pp. 132-139, vol. 194, Journal of magnetism and Magnetic Materials, Elsevier Science B.V.

Christoph Hehrlein, Amina Arab, and Christoph Bode, Drug-eluting stent: the "magic bullet" for prevention of restenosis?, 2002, pp. 417-423, vol. 97, No. 6, Basic Research in Cardiology, Steinkopff Verlag.

Hugh Herr, PhD, Presentation highlights: Prosthetic and orthotic limbs, May/Jun. 2002, pp. 11-12, vol. 39, No. 3, Journal of Rehabilitation Research and Development, VA/NIH Prosthetics Roundtable, http://www.vard.org/jour/02/39/3/sup/herr.htm.

Jing Liu, George Anthony Flores, and Rongsheng Sheng, In-vitro investigation of blood embolization in cancer treatment using magnetorheological fluids, 2001, pp. 209-217, vol. 225, Journal of Magnetism and Magnetic Materials, Elsevier Science B.V.

E. Regar, G. Sianos, and P. W. Serruys, Stent development and local drug delivery, 2001, pp. 227-248, vol. 59, British Medical Bulletin, The British Council.

Robert S. Schwartz, Elazer R. Edelman, Andrew Carter, Nicolas Chronos, Campbell Rogers, Keith A. Robinson, Ron Waksman, Judah Weinberger, Robert L. Wilensky, Donald N. Jensen, Bram D. Zuckerman, Renu Virmani and for the Consensus Committee, Drug-Eluting Stents in Preclinical Studies: Recommended Evaluation From a Consensus Group, 2002, pp. 1867-1873, vol. 106, Circulation: Journal of the American Heart Association, American Heart Association.

G. Segre and A. Silberberg, Behaviour of macroscopic rigid spheres in Poiseuille flow, 1962, pp. 115-157, vol. 14, Journal of Fluid Mechanics Digital Archive, Cambridge University Press.

R. Sheng, G. A. Flores, and J. Liu, In vitro investigation of a novel cancer therapeutic method using embolizing properties of magnetorheological fluids, 1999, pp. 167-175, vol. 194, Journal of magnetism and Magnetic Materials, Elsevier Science B.V.

International Search Report for PCT/US04/11861; Completed Jan. 10, 2005; Mailed Feb. 14, 2005.

Extended European Search Report for Application No. EP 07 75 5754, Dated Aug. 3, 2010.

* cited by examiner

PHOTOCHEMICAL ACTIVATION OF SURFACES FOR ATTACHING BIOMATERIAL

CROSS REFERENCE TO RELATED APPLICATIONS

This application is a Division of U.S. application Ser. No. 11/250,877, filed Oct. 14, 2005 now U.S. Pat. No. 7,653,734, which is a continuation in part of International Application No. PCT/US04/11861, filed Apr. 16, 2004, and claims priority benefit of U.S. Provisional Application No. 60/691,416, filed Jun. 17, 2005, U.S. Provisional Application No. 60/545,127, filed Feb. 17, 2004, U.S. Provisional Application No. 60/546,233, filed Feb. 20, 2004, and U.S. Provisional Application No. 60/463,505, filed Apr. 16, 2003, the entire disclosures of all of which are incorporated herein by reference for all purposes.

STATEMENT REGARDING FEDERALLY SPONSORED RESEARCH

Research leading to the disclosed invention was funded with funds from the National Heart Lung and Blood Institute under Contract No. HL59730. Accordingly, the United States Government has certain rights in the invention described herein.

BACKGROUND OF THE INVENTION

1. Field of Invention

This invention relates to surface modifications and more particularly to immobilization of molecules to surfaces by photochemical coupling.

2. Description of Related Art

A common shortcoming of implantable medical devices or surfaces is recognition of these devices by an organism as foreign objects followed by inflammation or even a rejection of such devices. Surface modification science concentrates on finding a better interface between a living tissue and a solid matrix. It is known to use various coatings to impart desirable properties to implantable surfaces. Such coatings are based on polymers and may include biologically active materials. Challenges in preparing such coatings include attaching biologically active materials to inert surfaces.

One of the techniques for derivatizing inert surfaces is photochemical coupling (see reference [1]). Photo-cross-linking chemistry based on organic solvents is well established (see references [2-5]). It is not known to use adsorption from aqueous solutions for application of photo-cross-linkers onto a polymer surface.

Aryl ketones (e.g., benzophenone or acetophenone derivatives) and aryl azides are known as photo-activatable cross-linkers suitable for covalent binding to virtually any type of polymer surface as described by Amos et al. Upon irradiation with long-wave UV (at about 350 nm), benzophenone residues form energy-rich excited triplet species, which are then inserted into carbon-hydrogen bonds (C—H bonds) of a polymeric surface by abstraction of hydrogen atoms from C—H bonds and form new carbon-carbon bonds (C—C bonds), resulting in covalent binding of benzophenone residues onto the polymeric surface (see FIG. 1).

U.S. Pat. No. 5,071,909 to Pappin et al. discloses a method for immobilizing proteins or peptides onto a membrane by formation of a polymeric network, which entraps the protein or peptide.

U.S. Pat. Nos. 3,959,078, 5,512,329 and 5,741,551 to Guire et al. disclose covalent bonding of polymeric molecules to surfaces through external activation. This approach is used to bind fibronectin peptide to a polystyrene surface by a photo-reaction between the peptide and a surface having a photo-activatable group.

U.S. Pat. No. 5,637,460 to Swan et al. discloses attaching a target molecule (synthetic polymers, carbohydrates, proteins, lipids, nucleic acids, etc.) to a surface by using photo-activatable groups.

It is evident from the prior art discussed above that prior to the present invention, photo-cross-linkers were not used for the attachment of functional reactive groups (other than the same photo-activatable groups used in the initial step of photo-immobilization) to the surface in order to activate it for further immobilization of biomolecules.

Replication defective adenoviruses (Ad or AdV) have been extensively used in both experimental and human gene therapy. Ad cell entry takes place through receptor-mediated endocytosis via dual Coxsackie-Adenovirus Receptor (CAR)/$\alpha v \beta 3$ integrins receptor system, although alternative pathways, such as fluid phase endocytosis might be operative under certain conditions (Meier and Greber, 2003). Various cell types differ widely in their level of CAR expression and this has proved to be a limiting factor for the level of transgene expression achievable with Ad. Furthermore, it is also clear that Ad cell entry and processing within cells via non-receptor endocytosis is a far less efficient means for vector processing than CAR-mediated cell entry. Thus, transgene expression in cells with relatively low amounts of CAR can only be achieved with high doses of Ad (Baker, 2004; Xu et al., 2005), and this has proved to be a major concern in terms of safety and toxicity (Yei et al., 1994; Thomas et al., 2001; Brunetti-Pierri et al., 2004).

Despite the foregoing developments, there is a need in the art for alternative means of attaching target molecules to surfaces.

All references cited herein are incorporated herein by reference in their entireties.

BRIEF SUMMARY OF THE INVENTION

Accordingly, the invention provides a water-soluble photo-activatable polymer comprising:
  (a) a photo-activatable group, wherein the photo-activatable group is adapted to be activated by an irradiation source and to form a covalent bond between the water-soluble photo-activatable polymer and a matrix having at least one carbon;
  (b) a reactive group, wherein the reactive group is adapted to covalently react with a biomaterial;
  (c) a hydrophilic group, wherein the hydrophilic group is present in an amount sufficient to make the water-soluble photo-activatable polymer soluble in water; and
  (d) a polymer precursor.

In certain embodiments, the polymer precursor comprises at least one monomer selected from the group consisting of allylamine, vinylamine, acrylic acid, carboxylic acid, alcohol, ethylene oxide, and acyl hydrazine.

In certain embodiments, the reactive group is a member selected from the group consisting of an amino group, a thiol-reactive group, a carboxy group, a thiol group, a protected thiol group, an acyl hydrazine group, an epoxy group, an aldehyde group, and a hydroxy group.

In certain embodiments, the thiol-reactive group is a member selected from the group consisting of a 2-pyridyldithio group, a 3-carboxy-4-nitrophenyldithio group, a maleimide group, an iodoacetamide group, and a vinylsulfonyl group.

In certain embodiments, the hydrophilic group is a member selected from the group consisting of an amino group and a carboxy group.

In certain embodiments, the photo-activatable group is a member selected from the group consisting of an aryl ketone and an aryl azide. In certain embodiments, the aryl ketone is a member selected from the group consisting of benzophenone and acetophenone.

In certain embodiments, the water-soluble polymer is represented by a formula:

$$(-CH-CH_2)_{n-k}(-CH-CH_2-)_k$$
$$\quad\ |\qquad\qquad\quad\ |$$
$$\ \ CH_2\qquad\qquad\ CH_2$$
$$\quad\ |\qquad\qquad\quad\ |$$
$$\ NH_2\qquad\qquad NH-OC-\text{C}_6H_4-COPh$$

wherein n is 50 to 2000 and k is 10 to 1000.

In certain embodiments, the water-soluble polymer is represented by a formula:

$$(-CH-CH_2)_{n-k-m}(-CH-CH_2)_m(-CH-CH_2-)_k$$
$$\quad\ |\qquad\qquad\qquad\ |\qquad\qquad\quad\ |$$
$$\ \ CH_2\qquad\qquad\quad CH_2\qquad\qquad CH_2$$
$$\quad\ |\qquad\qquad\qquad\ |\qquad\qquad\quad\ |$$
$$\ NH\qquad\qquad\qquad NH\qquad\qquad NH-OC-\text{C}_6H_4-COPh$$
$$O=C\qquad\qquad\qquad O=C$$
$$\quad\ |\qquad\qquad\qquad\ |$$
$$CH_2CH_2COOH\quad CH_2CH_2SS-\text{Py}$$

wherein n is 50 to 2000, k is 10 to 1000, and m is 10 to 1000.

Further provided is a process for producing the water-soluble photo-activatable polymer of the invention, the process comprising:

providing a polymer precursor comprising a plurality of reactive groups and a plurality of hydrophilic groups;

providing a photo-activatable reagent; and reacting the polymer with the photo-activatable reagent to obtain the water-soluble photo-activatable polymer, wherein a first portion of the reactive groups and/or hydrophilic groups is modified with the photo-activatable group.

In certain embodiments of the process, the first portion is from about 1% to about 50% of the reactive groups and/or hydrophilic groups.

In certain embodiments, the first portion is about 20% of the reactive groups and/or hydrophilic groups.

In certain embodiments, the process for producing the water-soluble photo-activatable polymer of the invention further comprises:

providing a reagent comprising a thiol-reactive group; and reacting unmodified reactive groups and/or hydrophilic groups with the reagent to obtain the water-soluble polymer, wherein a second portion of the reactive groups and/or hydrophilic groups is modified with the thiol-reactive group.

In certain embodiments, a sum of the first portion and the second portion is from about 60% to about 80%.

In certain embodiments, the thiol-reactive group is a member selected from the group consisting of a 2-pyridyldithio group, a 3-carboxy-4-nitrophenyldithio group, a maleimide group, an iodoacetamide group, and a vinylsulfonyl group.

Further provided is a composition of matter comprising a monomolecular layer of the water-soluble photo-activatable polymer of the invention and a matrix having at least one carbon, wherein the monomolecular layer is covalently attached to the matrix by a covalent bond between the photo-activatable group and the at least one carbon.

In certain embodiments, the composition further comprises a biomaterial having a plurality of active groups, wherein the biomaterial is covalently attached to the monomolecular layer by covalent bonding between the active groups and reactive groups.

In certain embodiments of the composition, at least one of the active groups is a member selected from the group consisting of amine, carboxyl, hydroxyl, thiol, phenol, imidazole, and indole. Preferably, the at least one of the active groups comprise thiol.

In certain embodiments of the composition, the biomaterial is a member selected from the group consisting of an antibody, a viral vector, a growth factor, a bioactive polypeptide, a polynucleotide coding for the bio active polypeptide, a cell regulatory small molecule, a peptide, a protein, an oligonucleotide, a gene therapy agent, a gene transfection vector, a receptor, a cell, a drug, a drug delivering agent, nitric oxide, an antimicrobial agent, an antibiotic, an antimitotic, dimethyl sulfoxide, an antisecretory agent, an anti-cancer chemotherapeutic agent, steroidal and non-steroidal anti-inflammatories, hormones, an extracellular matrix, a free radical scavenger, an iron chelator, an antioxidant, an imaging agent, and a radiotherapeutic agent. Preferably, the biomaterial is an anti-knob antibody, an adenovirus, a D1 domain of the Coxsackie-adenovirus receptor, insulin, an angiogenic peptide, an anti-angiogenic peptide, avidin, biotin, IgG, protein A, transferrin, and a receptor for transferrin.

In certain embodiments of the composition, the matrix is a member selected from a group consisting of polyurethane, polyester, polylactic acid, polyglycolic acid, poly(lactide-co-glycolide), poly(ε-caprolactone), polyethyleneimine, polystyrene, polyamide, rubber, silicone rubber, polyacrylonitrile, polyacrylate, and polymetacrylate, poly(alpha-hydroxy acid), poly(dioxanone), poly(orthoester), poly(ether-ester), poly(lactone), polytetrafluoroethylene, organosilane, mixtures thereof and copolymers thereof.

In certain embodiments of the composition, the matrix further comprises a magnetic field-responsive agent. In certain embodiments, the magnetic field-responsive agent is a superparamagnetic agent. Preferably, the superparamagnetic agent is a member selected from the group consisting of magnetite and maghemite nanocrystals as such, as aggregates or as dispersion in polymer from the list above.

In certain embodiments of the composition, the matrix is an implantable device. Preferably, the implantable device comprises at least one member selected from the group consisting of polyurethane, polyester, polylactic acid, poly(lactide-co-glycolide), poly(ε-caprolactone), polyethyleneimine, polystyrene, polyamide, rubber, silicone rubber, polyacrylonitrile, polyacrylate, polymetacrylate, polytetrafluoroethylene, organosilane, mixtures thereof and copolymers thereof.

In certain embodiments of the composition, the matrix is a particle having a diameter of about 5 nm to about 10 microns. Preferably, the particle comprises at least one member selected from the group consisting of polylactic acid, poly (lactide-co-glycolide), poly(ε-caprolactone), polyethyleneimine, mixtures thereof and copolymers thereof.

Further provided is a method of making the composition of the invention, the method comprising:

providing the matrix having at least one carbon;

providing an aqueous solution of the water-soluble photo-activatable polymer having the photo-activatable group and the reactive group;

contacting the matrix with the aqueous solution; and photo-activating the photo-activatable group by irradiation to covalently attach the water-soluble polymer via the photo-activatable group to the matrix and thereby forming the monomolecular layer of the composition.

In certain embodiments of the method of making the composition of the invention, the irradiation is performed at a wavelength from about 190 to about 900 nm. Preferably, the irradiation is performed at a wavelength of 280 to 360 nm.

Additionally, certain embodiments of the method further comprise providing a biomaterial having a plurality of active groups and reacting the plurality of active groups with the water-soluble photo-activatable polymer to covalently attach the biomaterial to the matrix.

Also provided is a process for delivery of a biomaterial, the process comprising:

providing the composition of the invention as a monomolecular layer and a matrix having at least one carbon, wherein the monomolecular layer is covalently attached to the matrix by a covalent bond between the photo-activatable group and the at least one carbon;

providing a biomaterial having a plurality of active groups, wherein the biomaterial is covalently attached to the monomolecular layer by covalent bonding between the active groups and the reactive groups; and administering the matrix to the cell and thereby delivering the biomaterial.

Replication-defective adenoviral vectors have shown promise as a tool for gene delivery-based therapeutic applications due to a number of unique advantages, including an efficient mechanism of nuclear entry and ability to transduce both quiescent and dividing cells in vivo with transgenes of more than 30 kb without integration into the host cell genome. Their use is however limited by their low efficacy in cells characterized by scarce expression of Coxsackie-adenovirus receptor (CAR), the primary receptor responsible for the cell entry of the virus, and by systemic adverse reactions resulting from the inability to effectively localize and provide the sustained presence of the vector in the target tissue, while minimizing its escape from the delivery site. To address these problems, inventors investigated the affinity immobilization of adenovirus (AdV) on a biodegradable nanoparticle (NP) platform. Stable vector-specific association of AdV with nanoparticles (NP) leads to formation of composites that enter cells through a CAR-independent pathway allowing for use of substantially lower vector doses for efficient transduction. Additionally the dissemination of the vector may be prevented by its association with 300-500 nm sized NP exhibiting lower rates of diffusion across solid tissues.

Biodegradable polyester-based nanoparticles possess high biocompatibility, and can be prepared with strictly controlled size and narrow size distribution, a prerequisite for safe parenteral administration. Such particles have been extensively investigated as injectable drug and gene carriers. The enhancement of the viral gene delivery by forming an affinity complex with biodegradable nanoparticles present a novel approach for improving and extending the applicability of the viral gene therapeutic strategies.

BRIEF DESCRIPTION OF SEVERAL VIEWS OF THE DRAWINGS

The invention will be described in conjunction with the following drawings in which like reference numerals designate like elements and wherein.

Figure 4A:
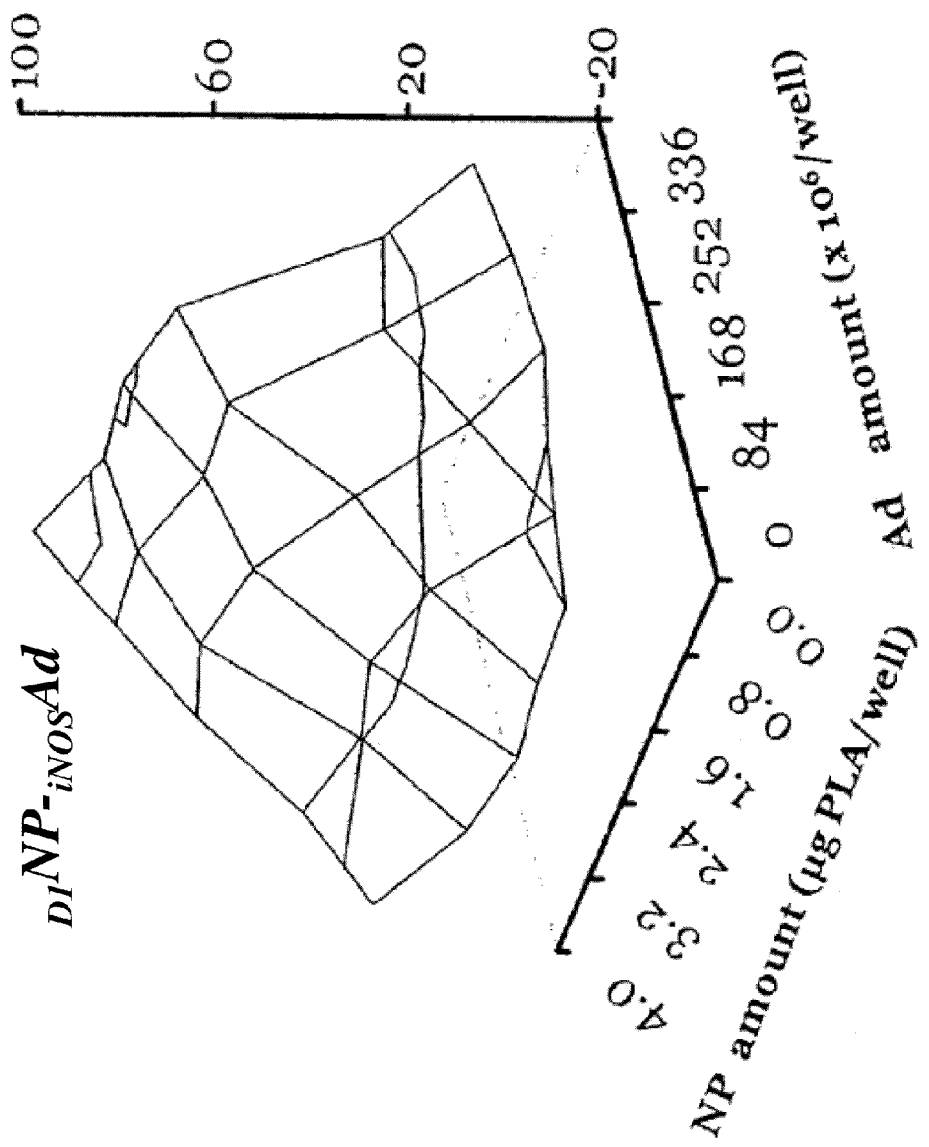
FIG. 4A demonstrates A10 cell growth inhibitory effect using nanoparticles modified with D1 domain of CAR and adenoviral vector encoding inducible nitric oxide synthase (iNOS-AdV).
Figure 4B:
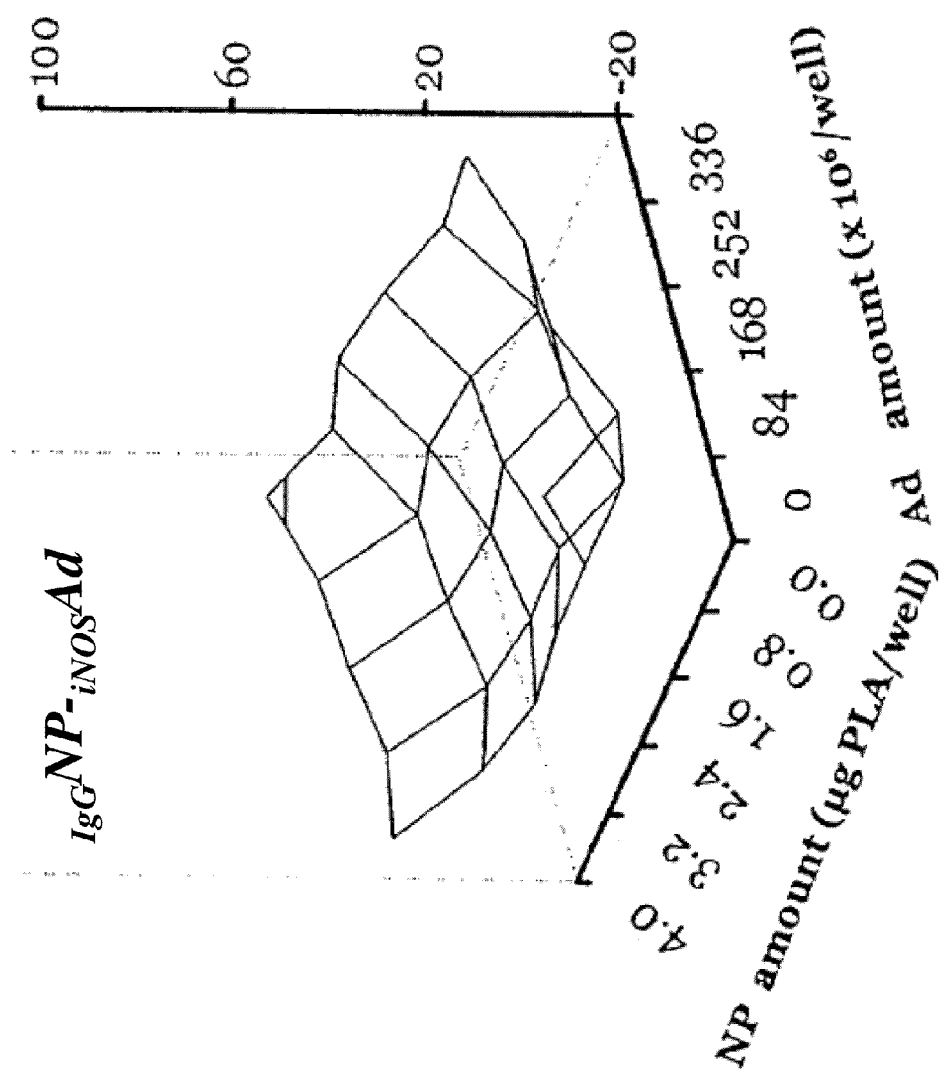
FIG. 4B demonstrates A 10 cell growth inhibitory effect using nanoparticles modified with IgG and iNOS-AdV.
Figure 4C:
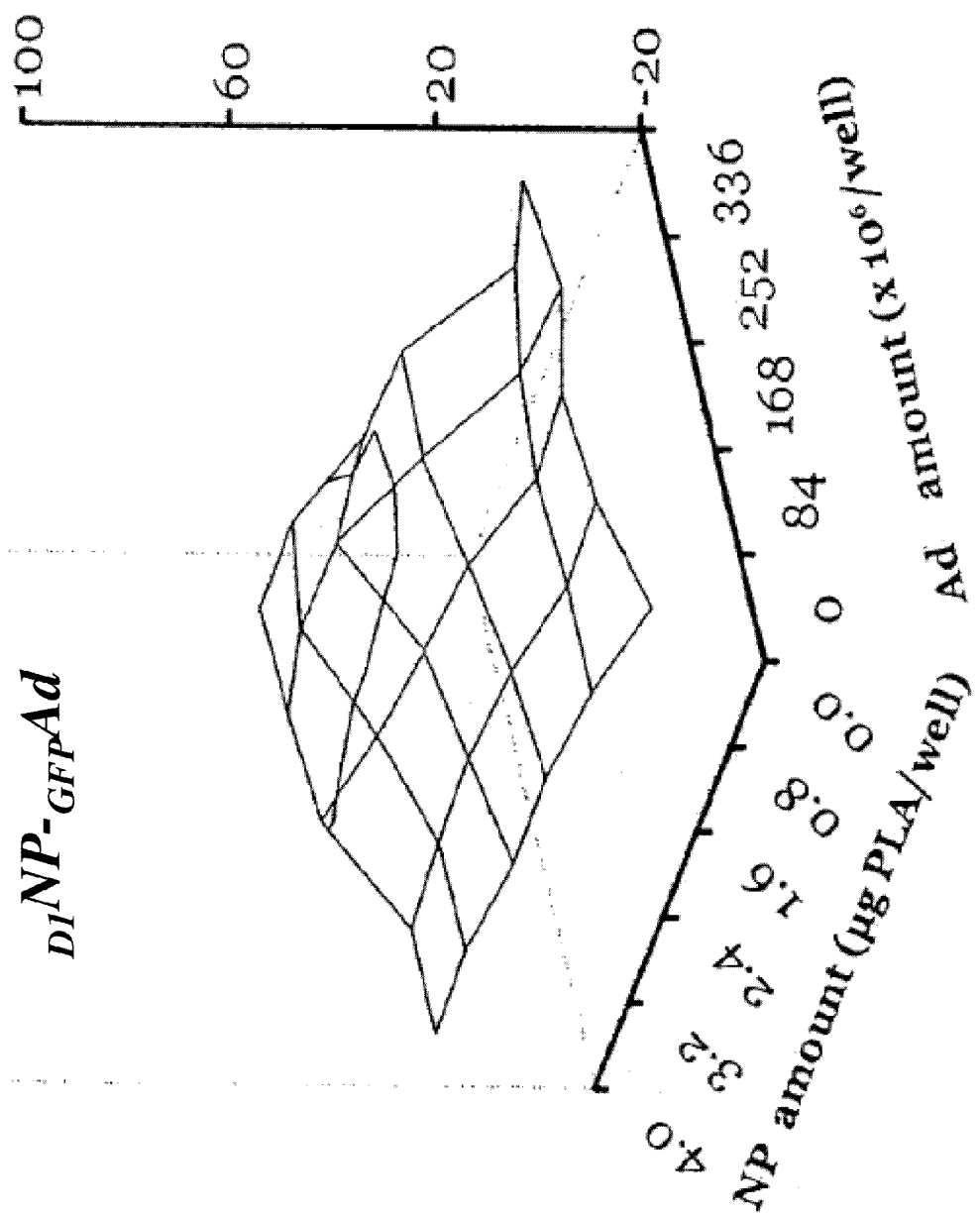
FIG. 4C demonstrates A10 cell growth inhibitory effect using nanoparticles modified with D1 and GFP-AdV.
Figure 4D:
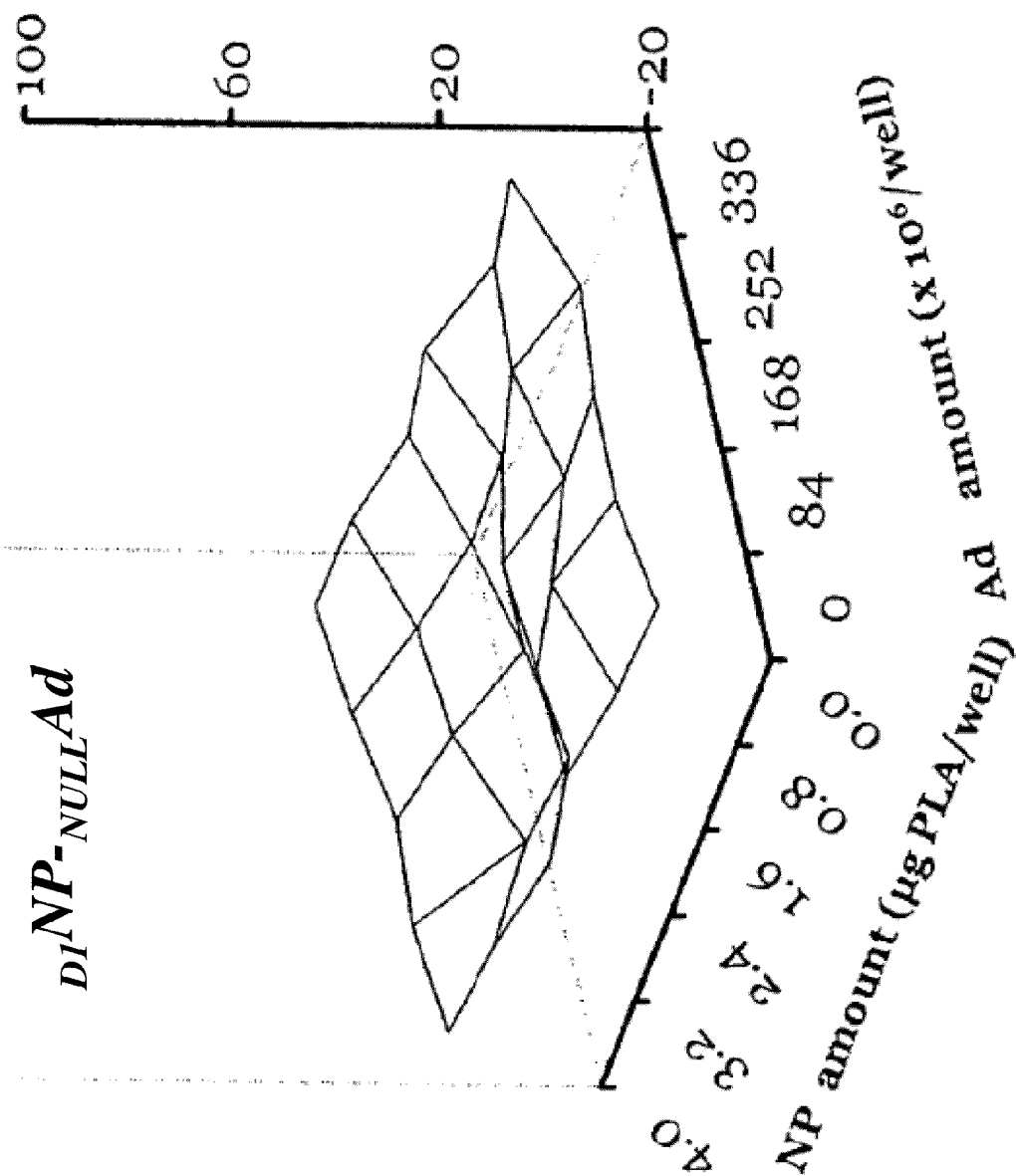
FIG. 4D demonstrates A10 cell growth inhibitory effect using nanoparticles modified with D1 and null-AdV. A null adenovirus is one that contains no transgene.
Figure 4E:
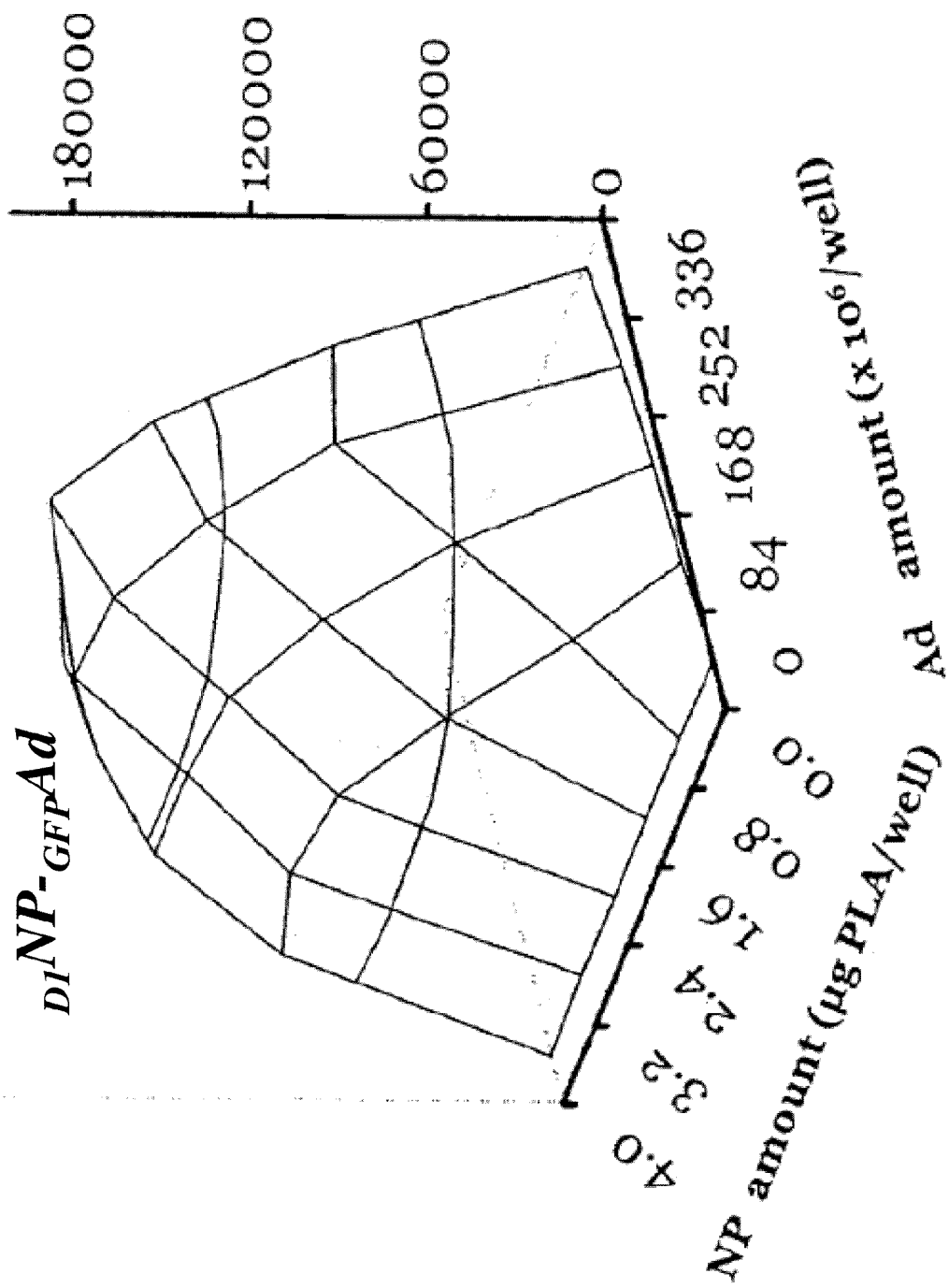
FIG. 4E demonstrates GFP fluorescence (in relative units) of nanoparticles modified with D1 and GFP-AdV.
Figure 4F:
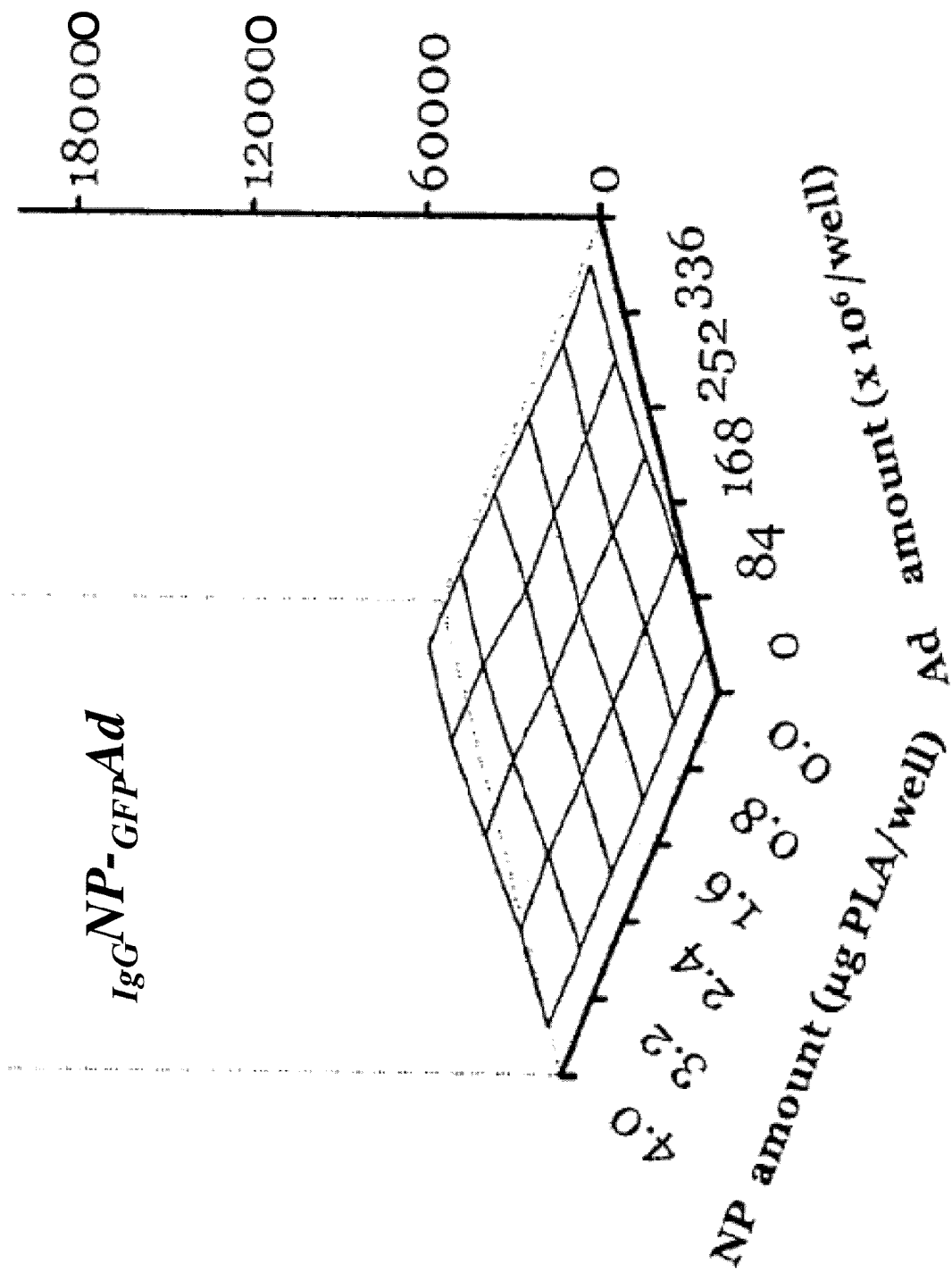
FIG. 4F demonstrates GFP fluorescence of nanoparticles modified with IgG and GFP-AdV.

The A10 cell growth inhibitory effect of $_{iNOS}$Ad in the presence of NP modified with D1 ($_{D1}$NP, FIG. 4A) and non-immune IgG ($_{nIgG}$NP, FIG. 4B) in comparison to the reporter gene expression mediated by respective formulations prepared with $_{GFP}$Ad vector (FIGS. 4E, 4F). A10 growth inhibition was also studied for control formulations including NP-Ad formulated with $_{GFP}$Ad (C) and $_{NULL}$Ad (FIG. 4D). The reporter gene expression and cell growth inhibition were assayed 48 hr post treatment by direct cell fluorimetry ($\lambda_{em}/\lambda_{ex}$ 485 nm/535 nm) and using the Alamar Blue assay ($\lambda_{em}/\lambda_{ex}$ 544 nm/580 nm), respectively.

Figure 5:
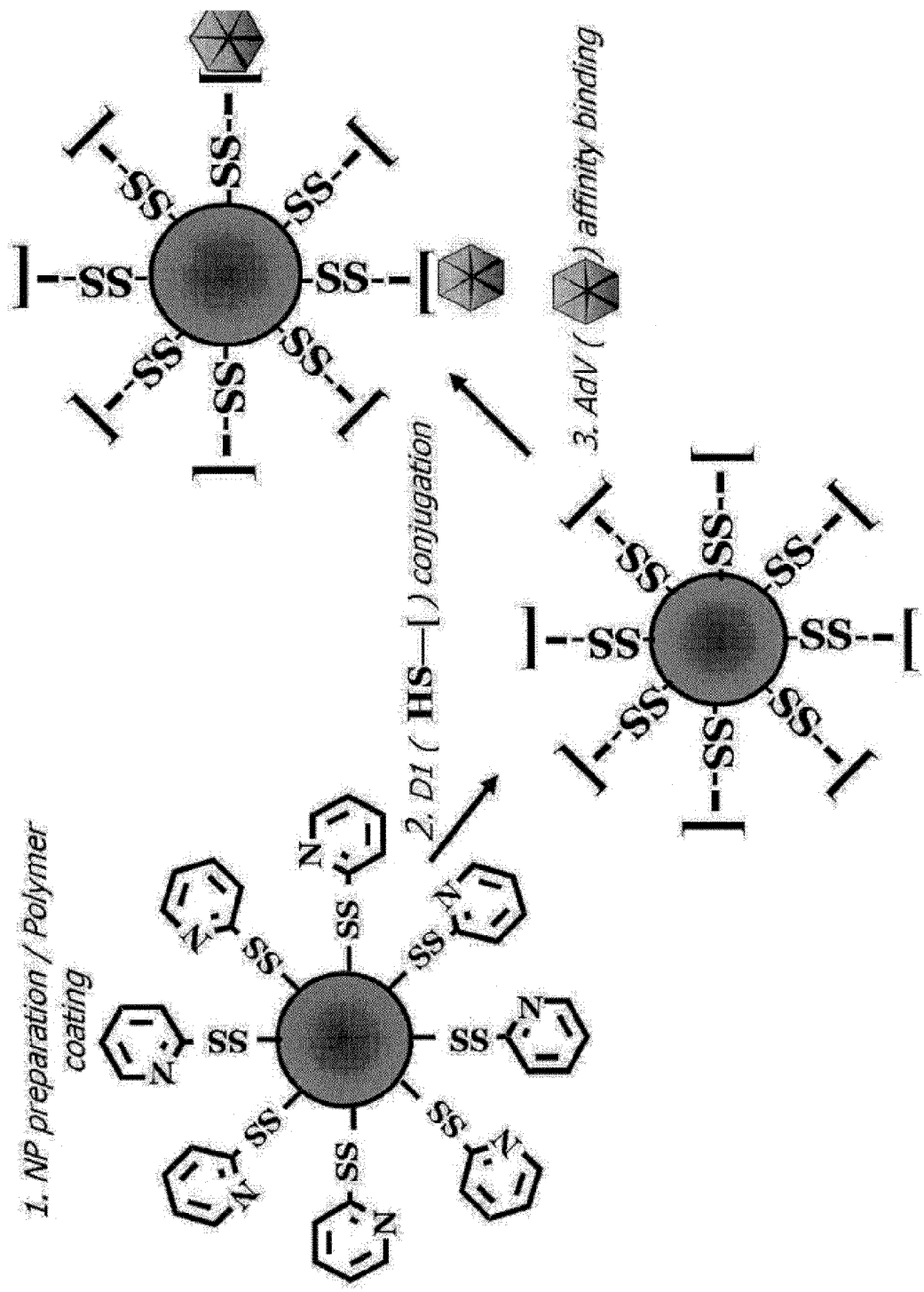

FIG. 5 is a schematic representation of the method of preparing AdV immobilized nanoparticles (AdV-NP).

Figure 6A:
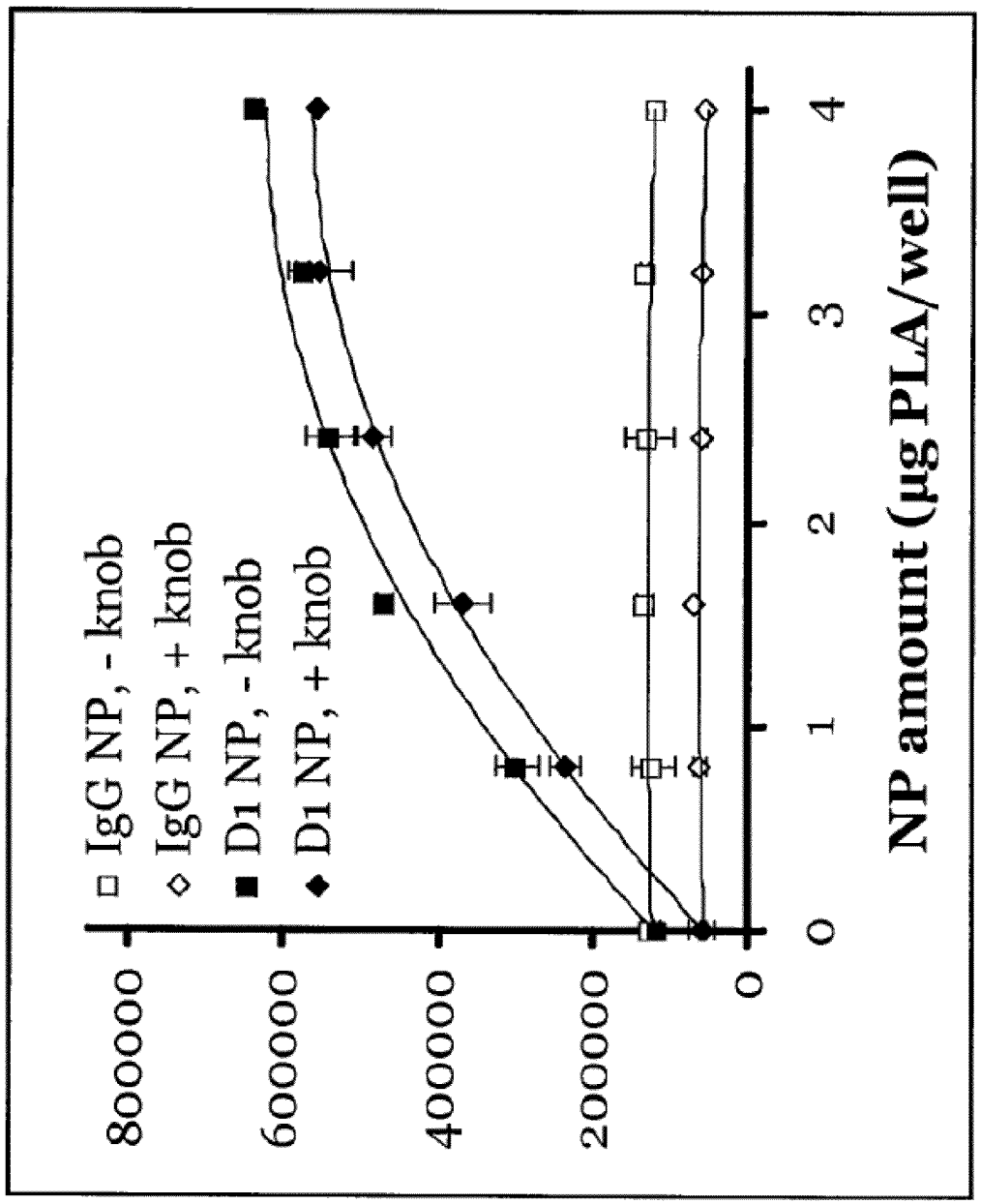
Figure 6B:
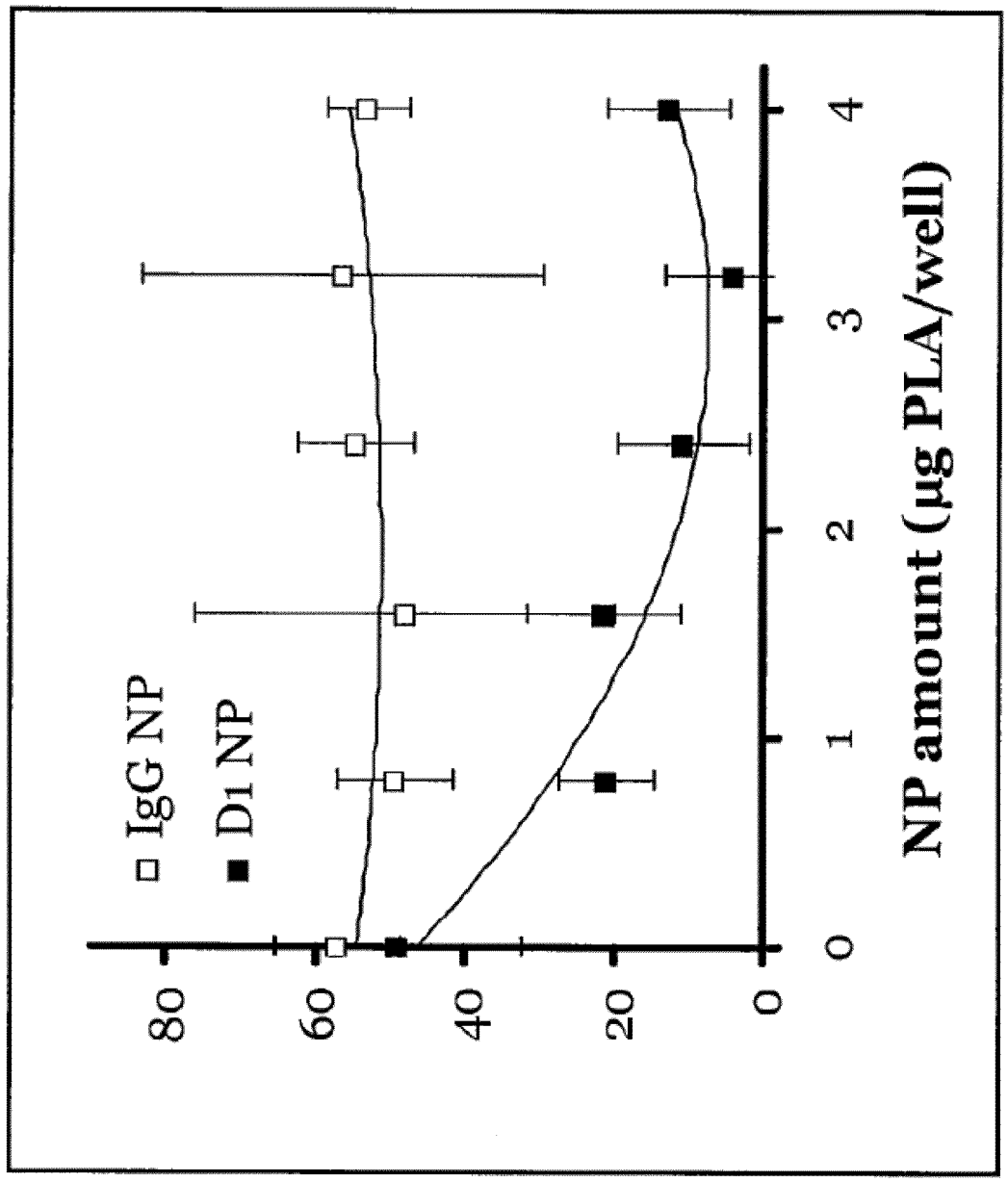
Figure 6C:
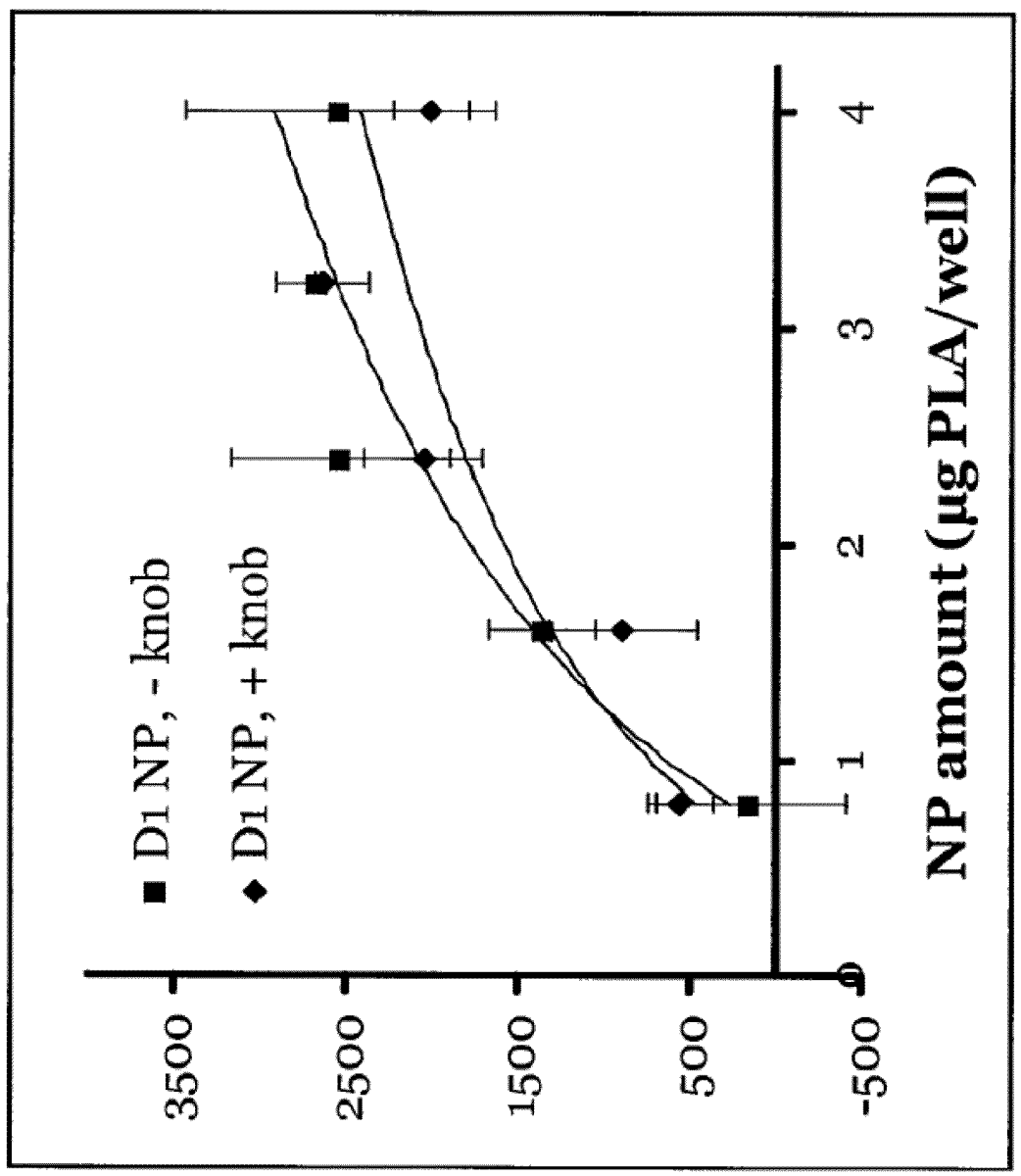

FIGS. 6A-6C show the effect of knob fiber protein on the transduction and uptake of composite-forming nanoparticles (NP) measured as a function of NP dose in smooth muscle cells (A10). The cells were pretreated with knob dissolved in the medium at 5 µg/ml for 1 hr prior to addition of Ad ($2 \times 10^8$/well) in the presence of $_{D1}$NP (0-4 µg PLA/well), or $_{nIgG}$NP used as a control. Knob-containing cell medium was aspirated, the cells were washed with PBS and incubated for 2 hr with the formulations. Gene expression was assayed fluorimetrically ($\lambda_{em}$ and $\lambda_{ex}$ 485 nm and 535 nm, respectively) in live cells 2 days post treatment (FIG. 6A). The comparative effect of knob on the gene transfer in the presence of the complexes and the control nIgGNP, expressed as inhibition of expression, is presented in (FIG. 6B). The comparative effect of knob pretreatment on the intracellular level of NP (FIG. 6C) was measured using $\lambda_{em}/\lambda_{ex}$ 544 nm/580 nm. Ad immobilization on NP resulted in a significantly greater expression (p<0.001, FIG. 6A). Error bars indicate standard deviation.

Figure 7A:
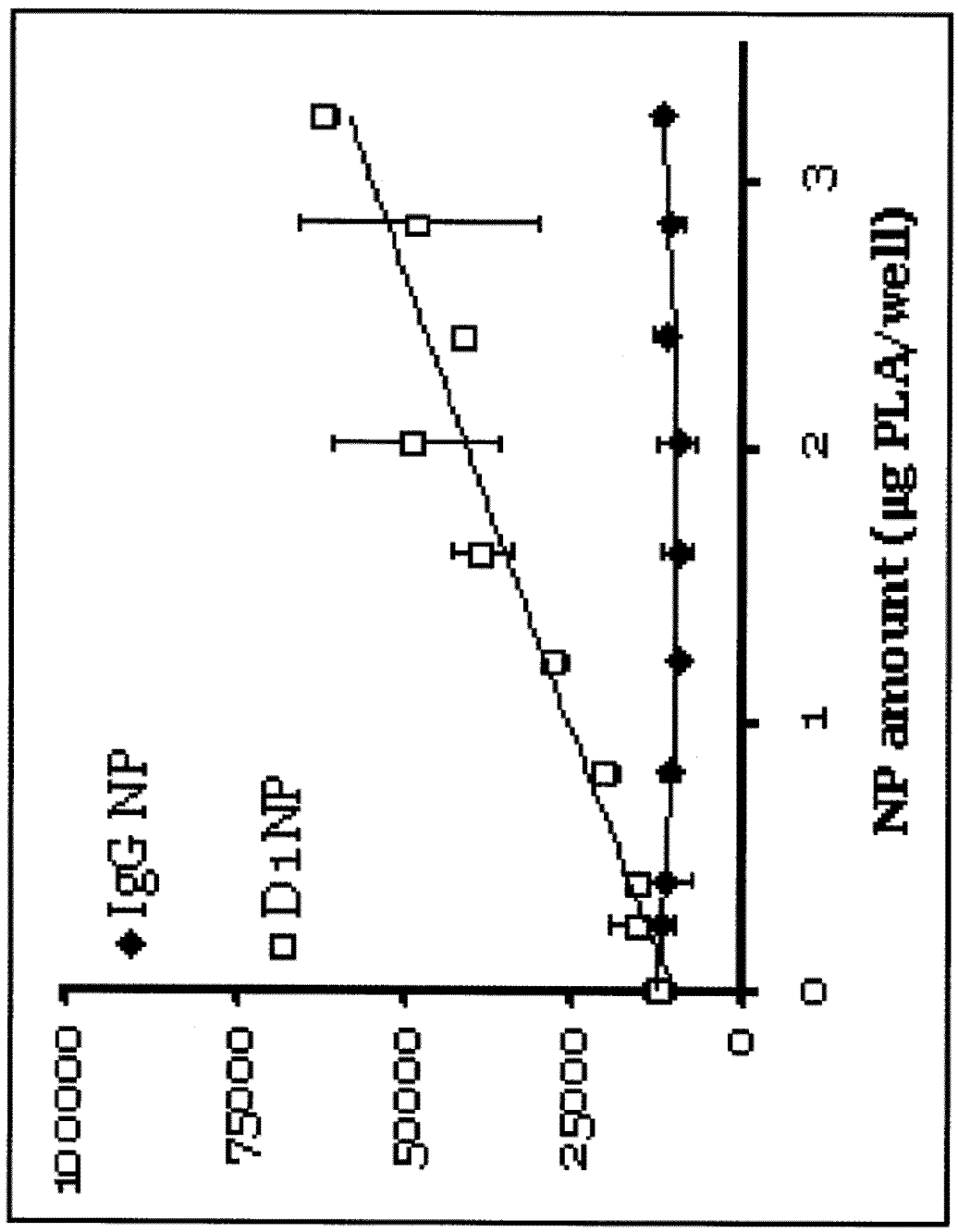
Figure 7B:
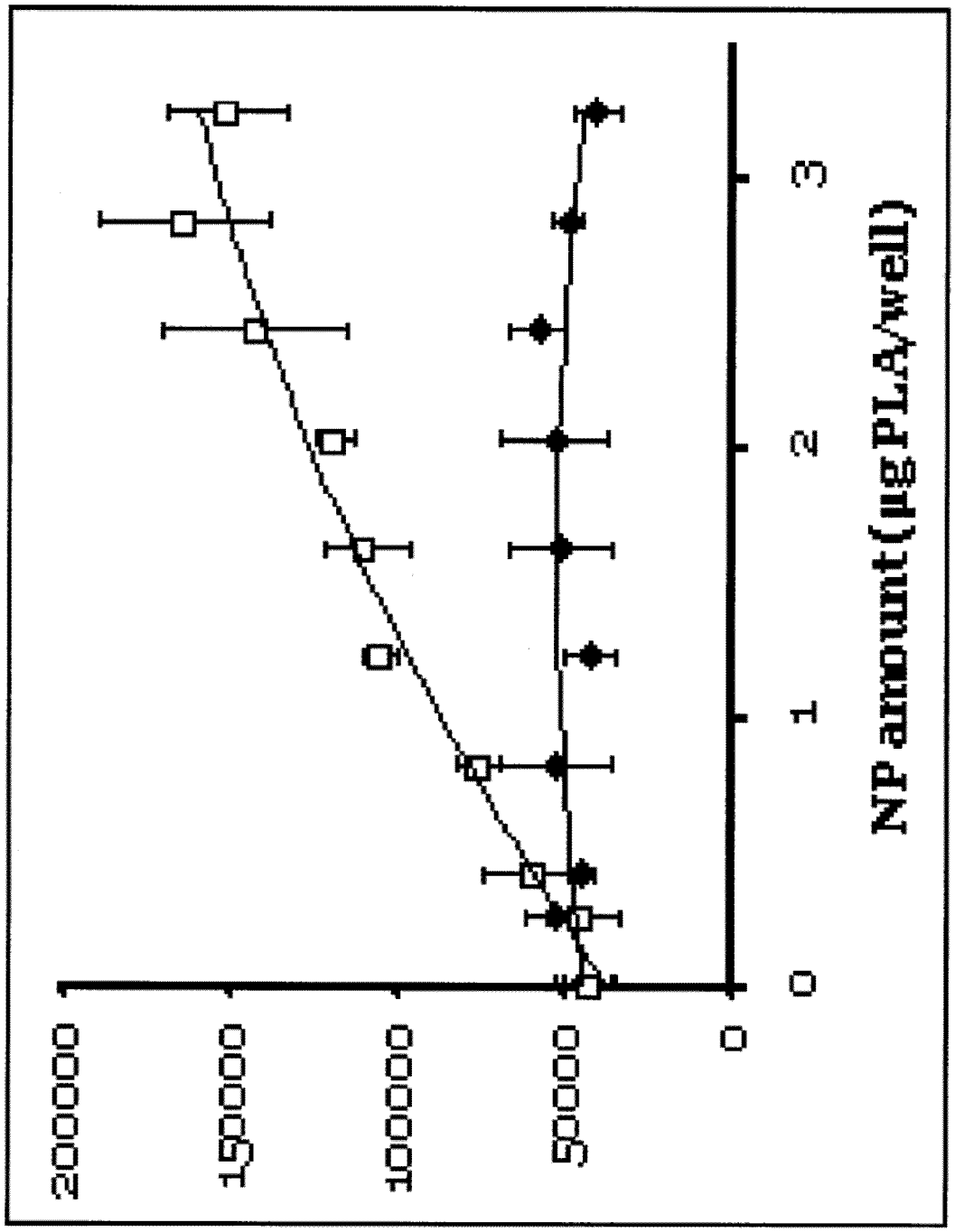
Figure 7C:
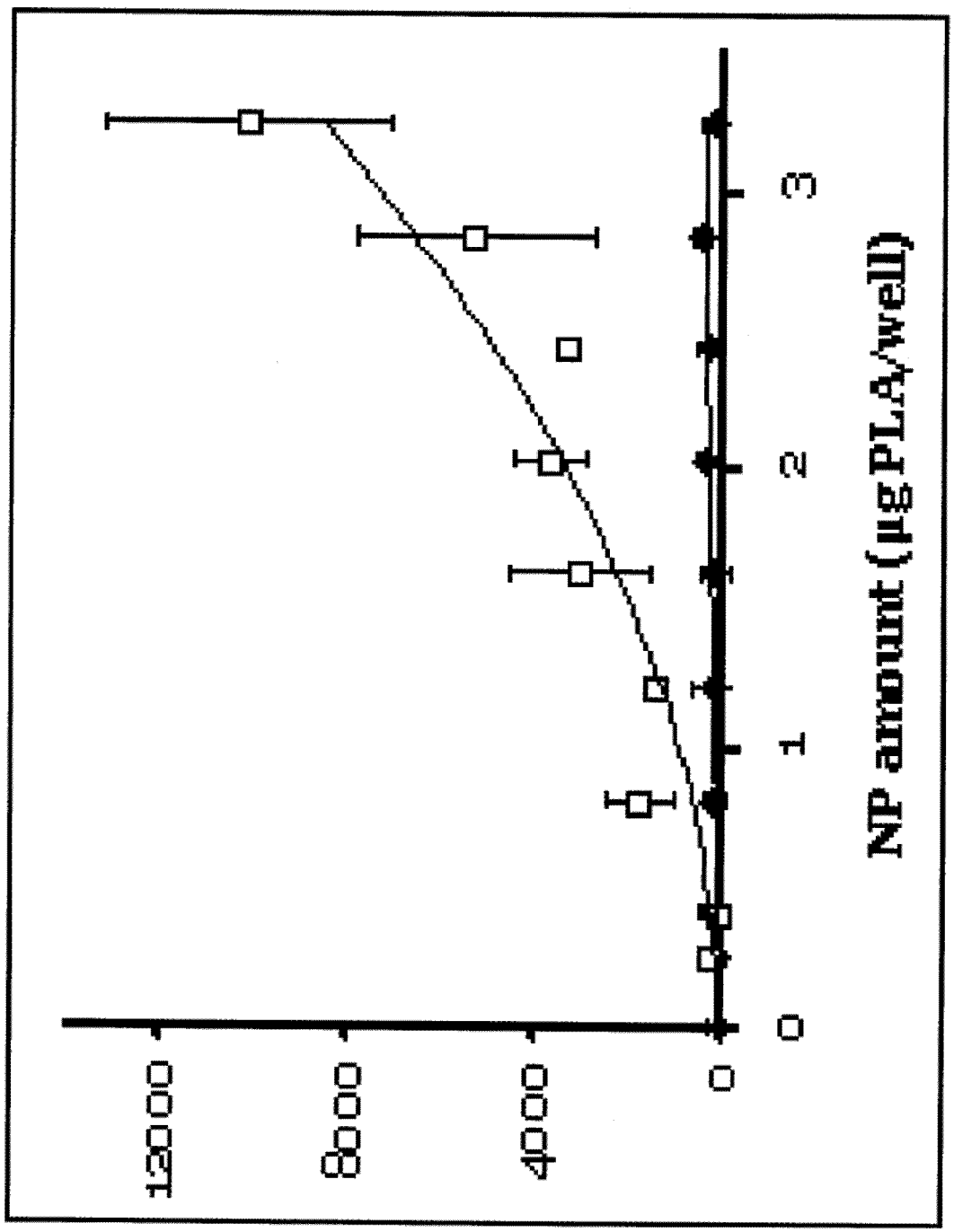
Figure 7D:
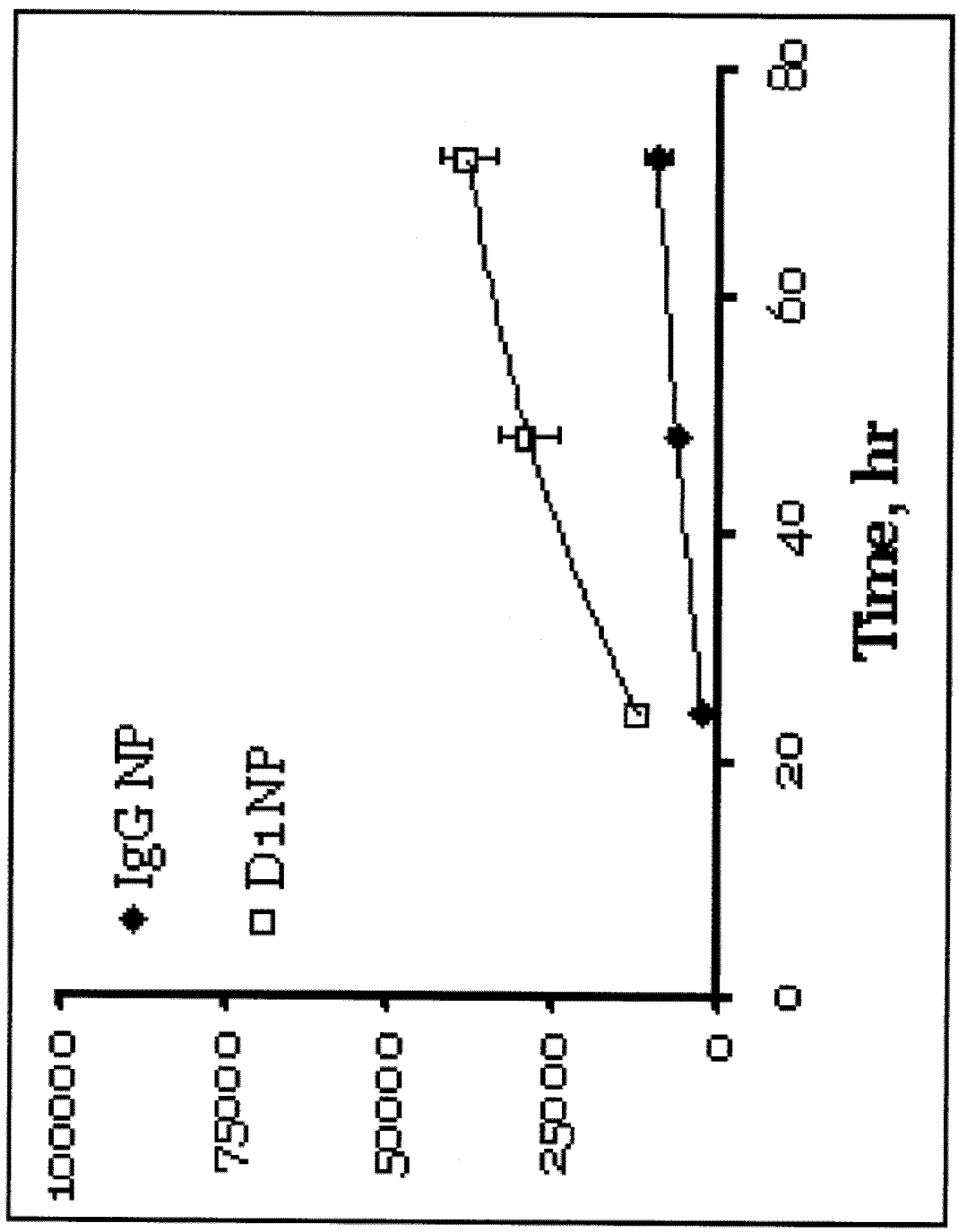
Figure 7E:
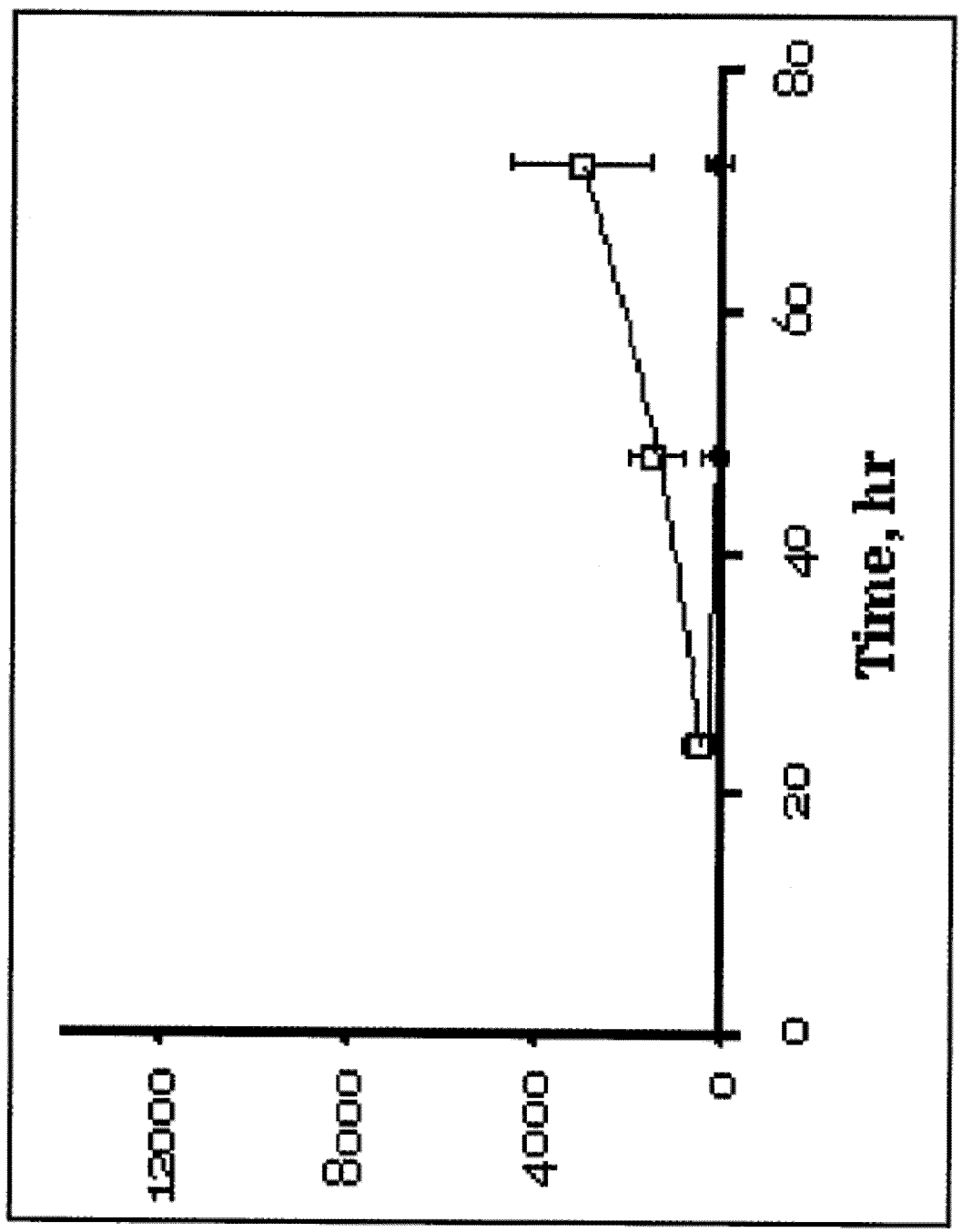
Figure 7F:
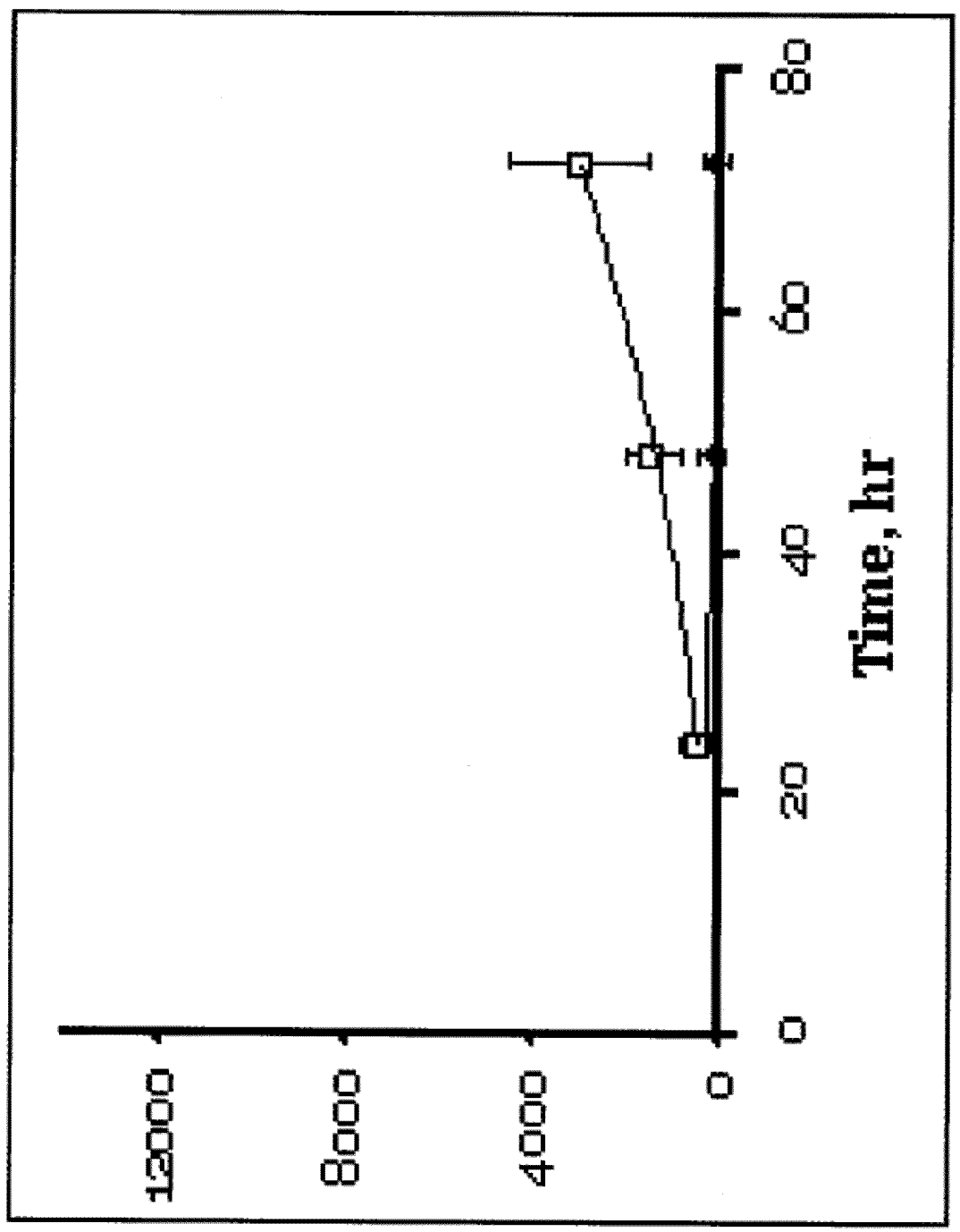

FIGS. 7A-7F are graphs demonstrating levels of GFP transgene expression following NP-Ad complex administration in cultures of rat aortic smooth muscle cells (A10) (FIGS. 7A, 7D), sheep blood outgrowth endothelial cells (BOEC) (FIGS. 7B and 7E) and murine heart endothelioma cells ($H_5V$) (FIGS. 7C and 7F). Increasing amounts of NP were combined with GFP-encoding Ad at a dose of $1.3 \times 10^8$ viral particles/well. FIGS. 7A-7C show GFP amount in cells 72 hr post treatment as a function of NP dose used to form the complexes with D1 tethering associated with significantly greater GFP expression for all NP doses (p<0.001). FIGS. 7D-7F show GFP amount in cells treated with complexes at a NP dose of 1.6 µg PLA/well as a function of time post treatment with D1 tethering demonstrating significantly greater expression at all time points (p<0.001). Error bars indicate standard deviation.

Figure 8B:
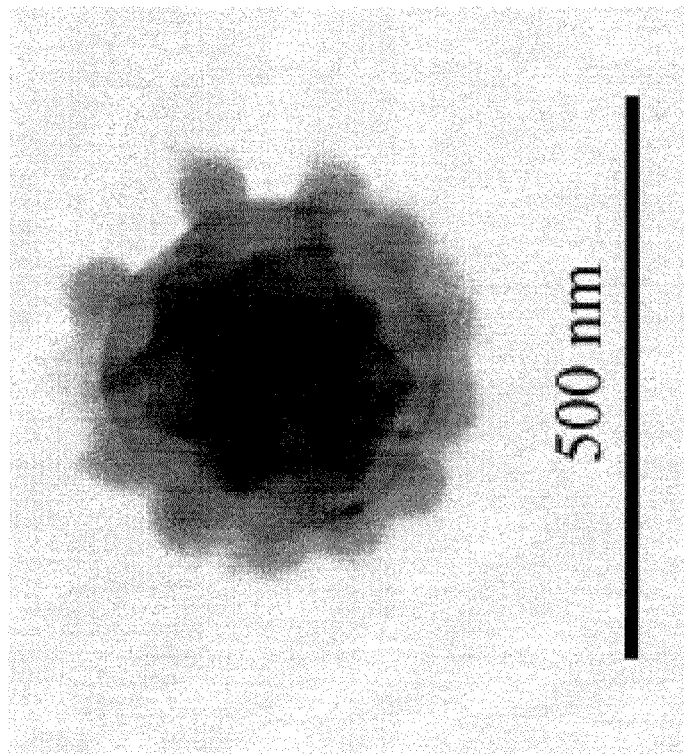
Figure 8A:
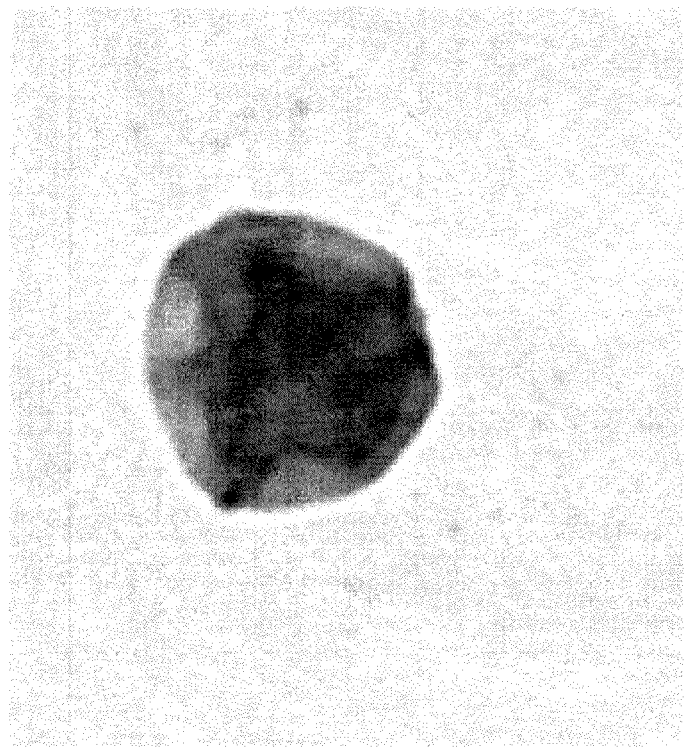

FIG. 8A is a transmission electron micrograph of a free NP and FIG. 8B is a transmission electron micrograph of a NP-Ad complex formed via tethering Ad to the surface of PLA nanoparticles using D1-Ad affinity binding. Electron microscopy (FEI Tecnai G2 Electron Microscope, Netherlands) was performed after negative staining with 2% (w/v) uranyl acetate. The original magnification is ×50000.

Figure 9A:
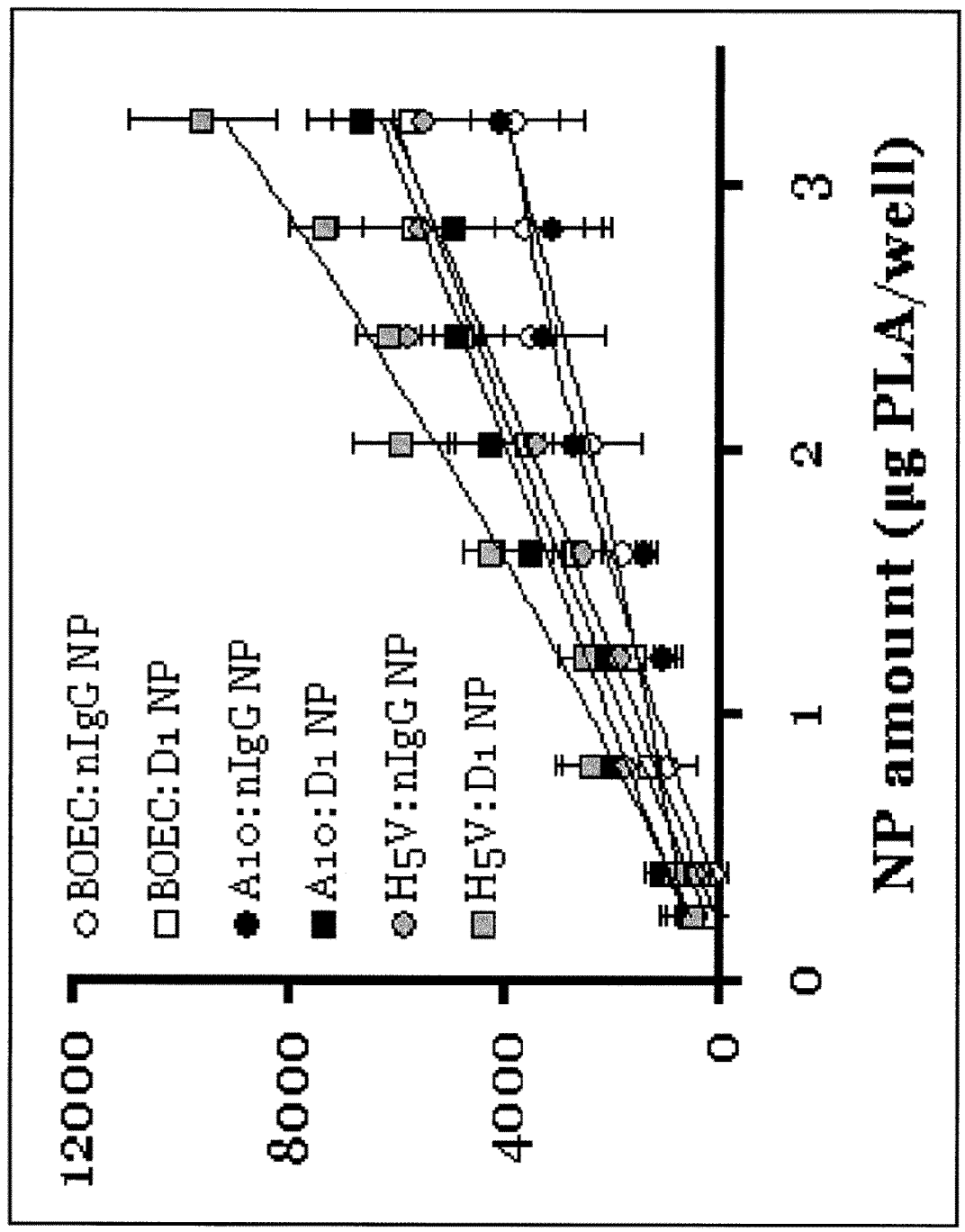
Figure 9B:
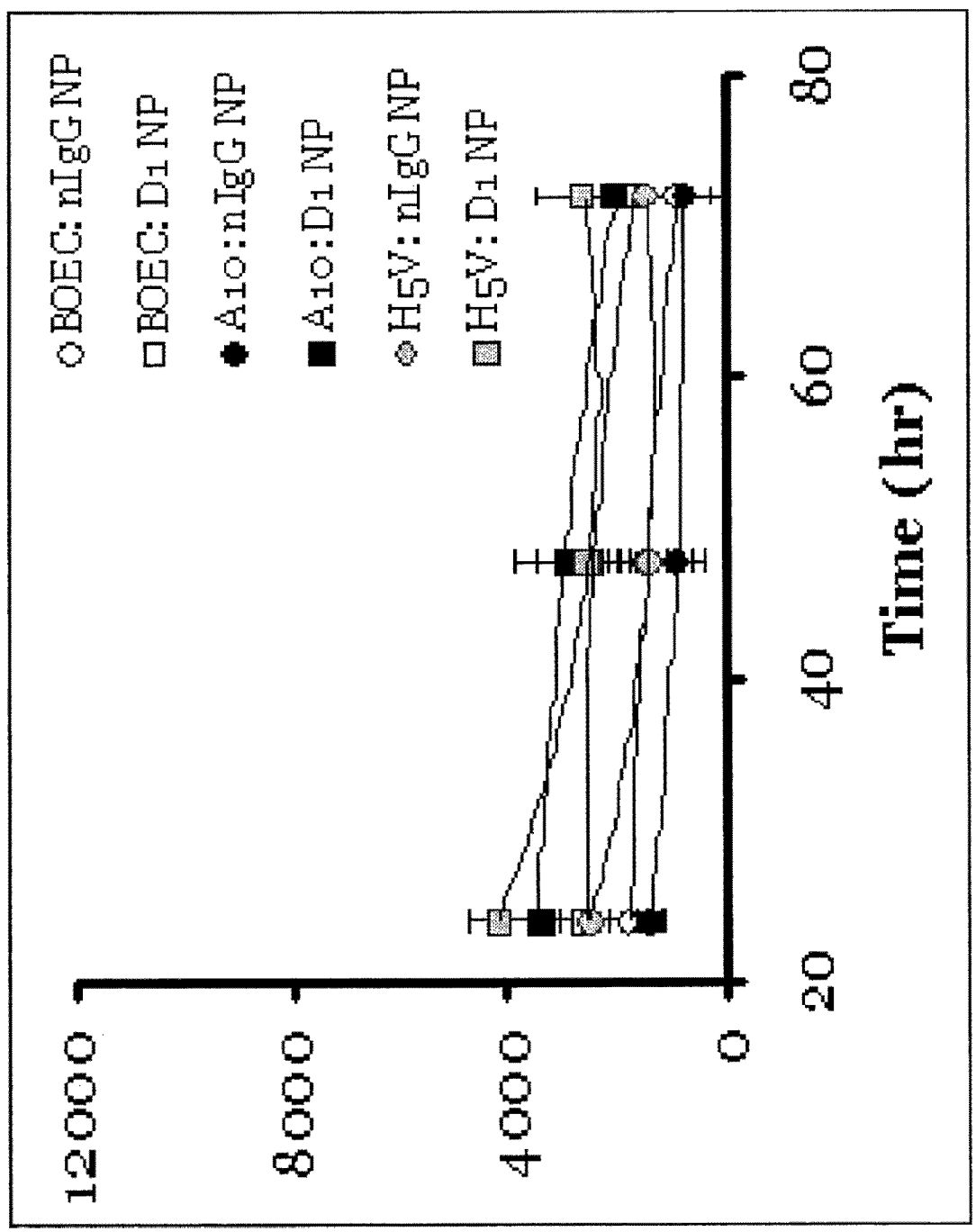

FIGS. 9A and 9B are graphs demonstrating the uptake and retention of complex-forming NPs and control NPs ($_{D1}$NP and $_{nIgG}$NP, respectively) by BOEC, A10 and H5V cells. The NPs were incubated with AdV at a dose $1.3 \times 10^8$ viral particles/well and added to the cells for 2 hr. The NP uptake (FIG. 9A) was determined 24 hr post treatment as a function of the NP dose (0-3.2 μg PLA/well). The change in the intracellular levels with time (24-72 hr) was determined for NP applied at a dose of 1.6 μg PLA/well PLA (FIG. 9B). The measurements were performed fluorimetrically in live cells using $\lambda_{em}/\lambda_{ex}$ 544 nm/580 nm Error bars indicate standard deviation.

Figure 10A:
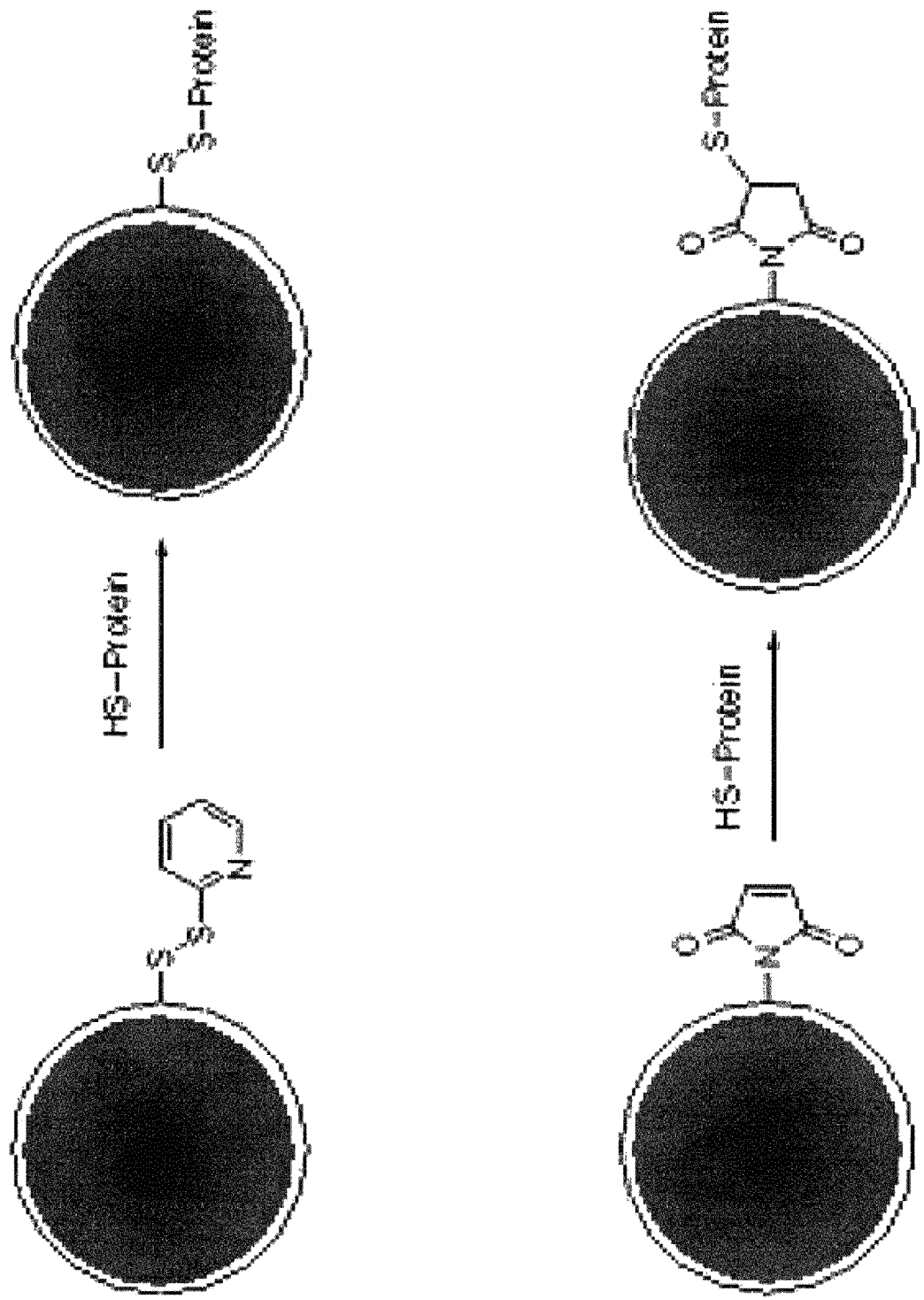
Figure 14:
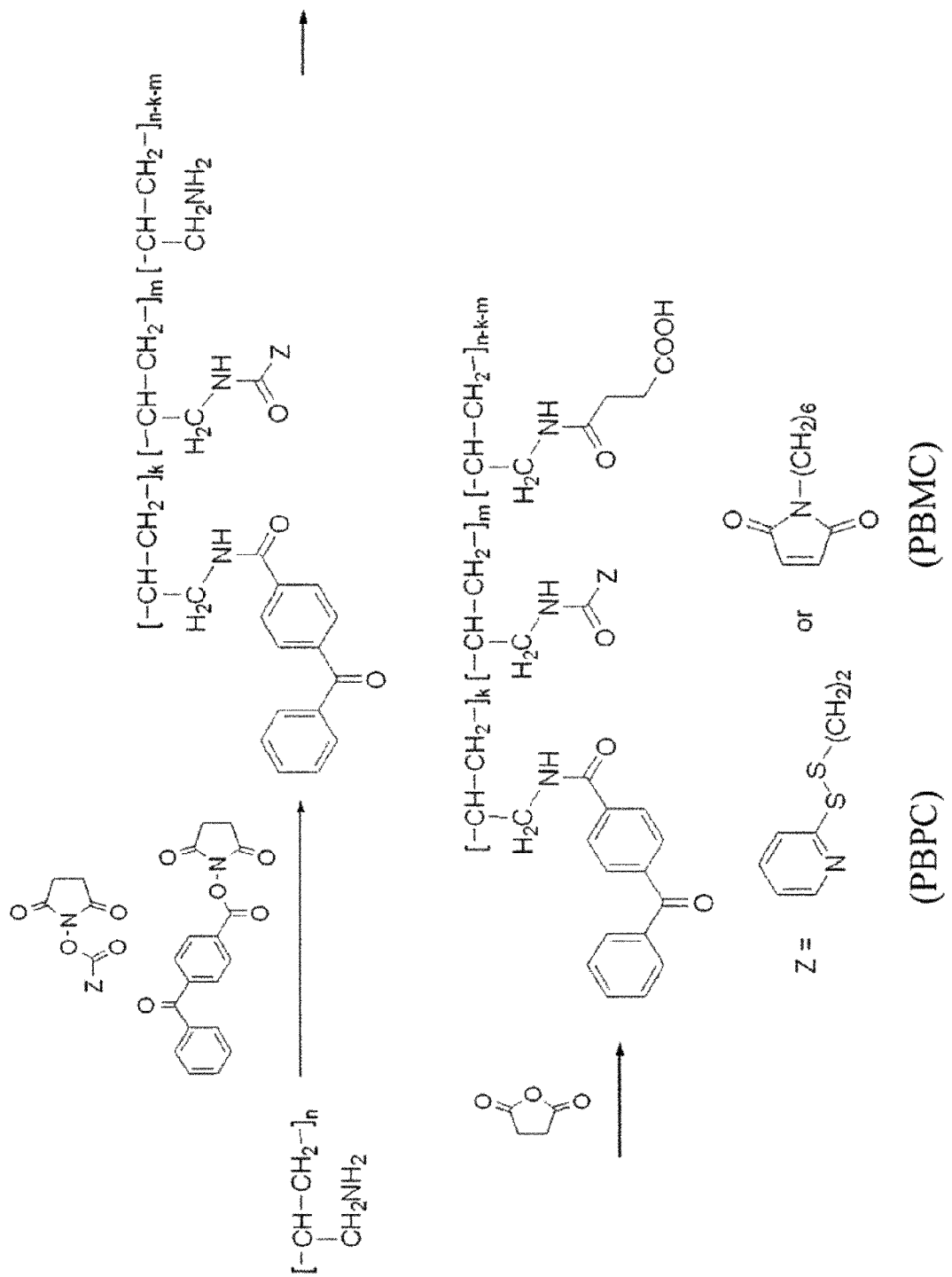

FIG. 10A shows the effect of NP surface modification with D1 using surface activation with poly(allylamine)-benzophenone-pyridyldithio-carboxylate (PBPC) and poly(allylamine)-benzophenone-maleimido-carboxylate (PBMC) (see also FIG. 14). Thiolated biomolecule (e.g., HS-Protein) reacts with the NP surface activated with PDT groups and MI groups to form a biodegradable disulfide (S—S), or a non-biodegradable thioether (C—S) bond, respectively. The respective NP were incubated with Ad at a dose of $1.3 \times 10^8$ viral particles/well and added to the cells for 2 hr.

Figure 10B:
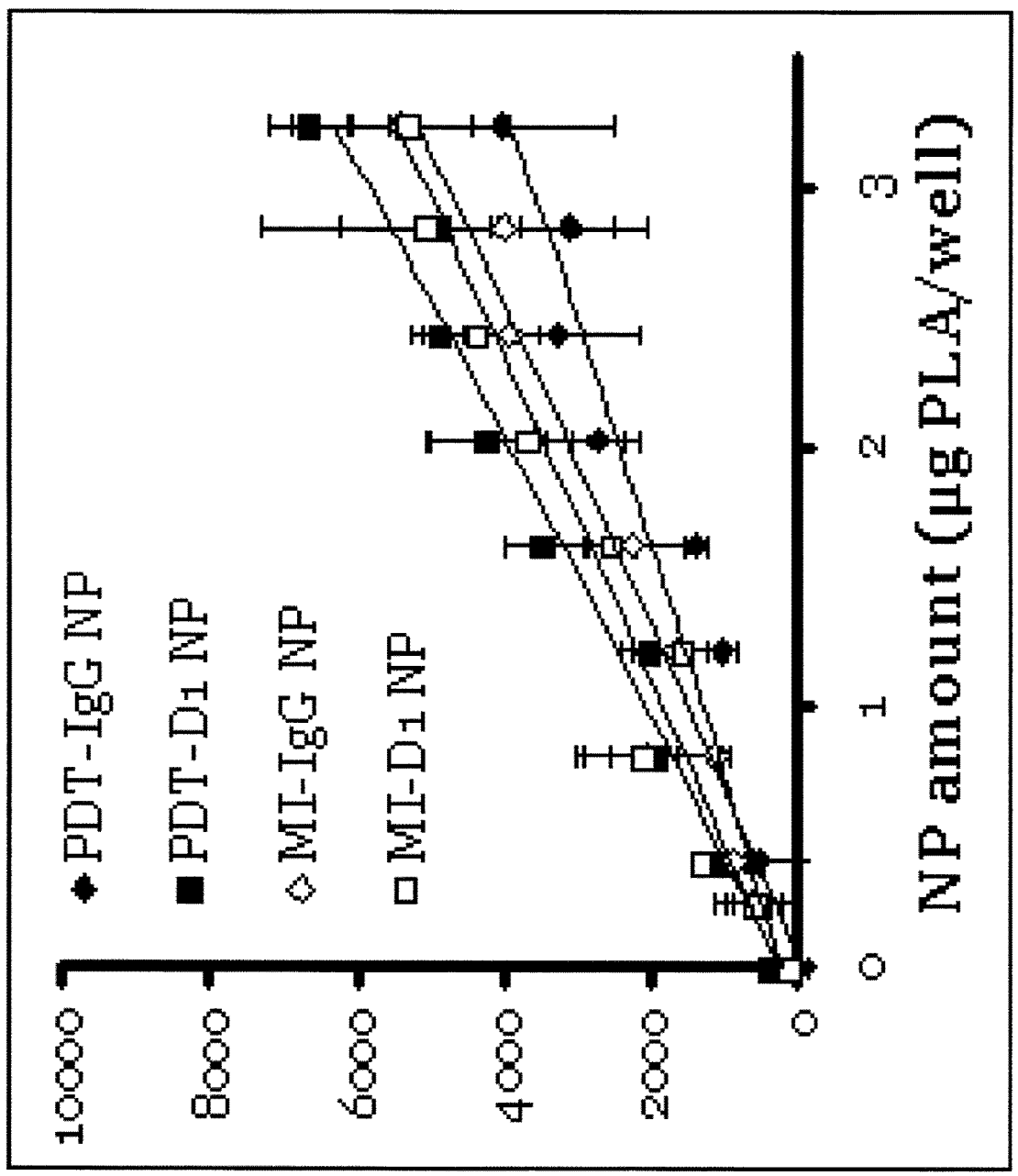
Figure 10C:
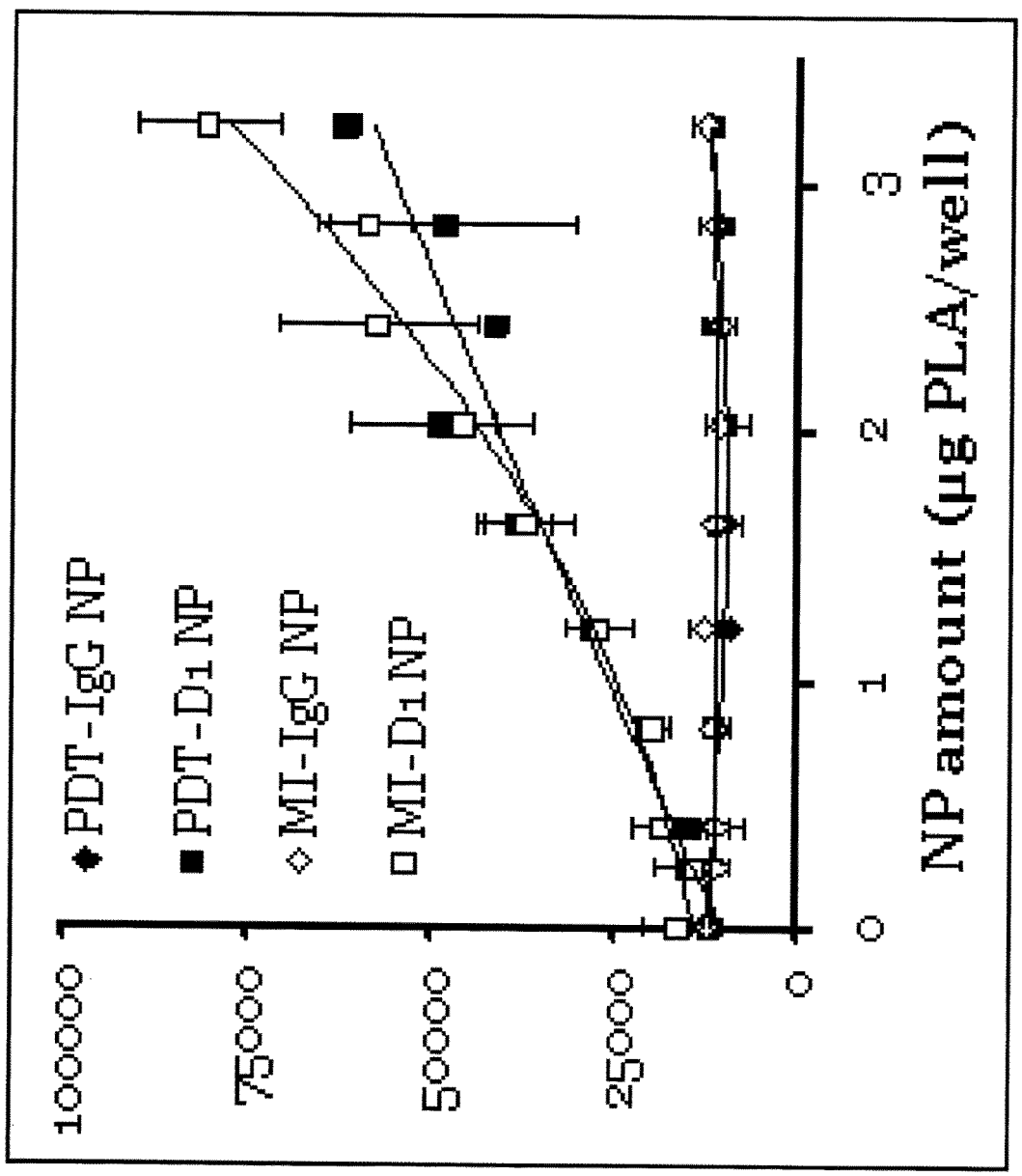

FIGS. 10B and 10C are graphs of NP uptake and GFP expression of the complexes respectively. The effect of the bond character on NP uptake and GFP expression of the complexes was measured fluorimetrically using $\lambda_{em}/\lambda_{ex}$ 544 nm/580 nm, and 485 nm/535 nm, respectively, using $_{nIgG}$NP as a control.

Figure 10D:
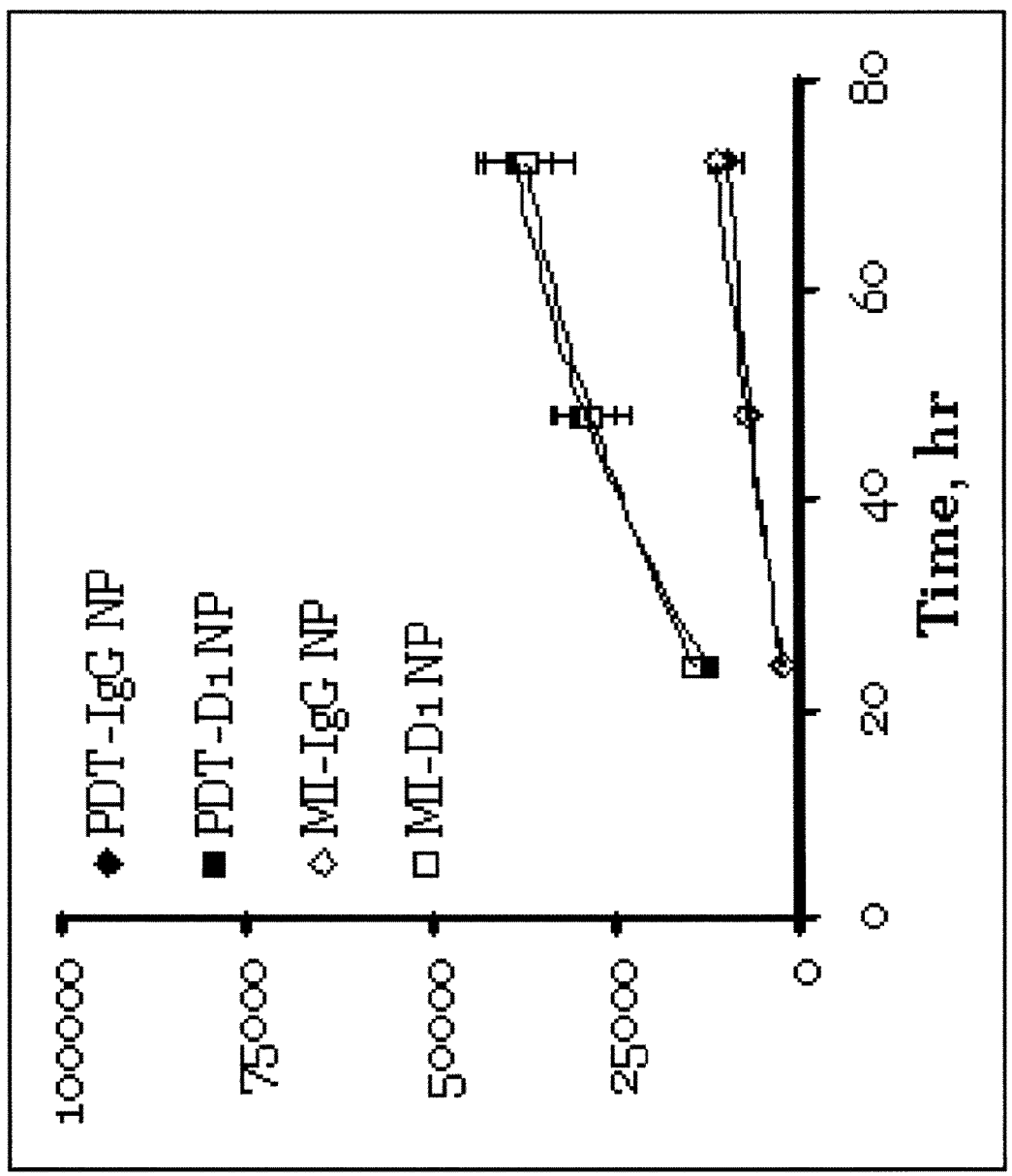

FIG. 10D is a graph demonstrating a time course of the gene expression mediated by the complexes formed at a NP dose of 1.6 μg PLA/well was followed for 72 hr. Error bars indicate standard deviation.

Figure 11A:
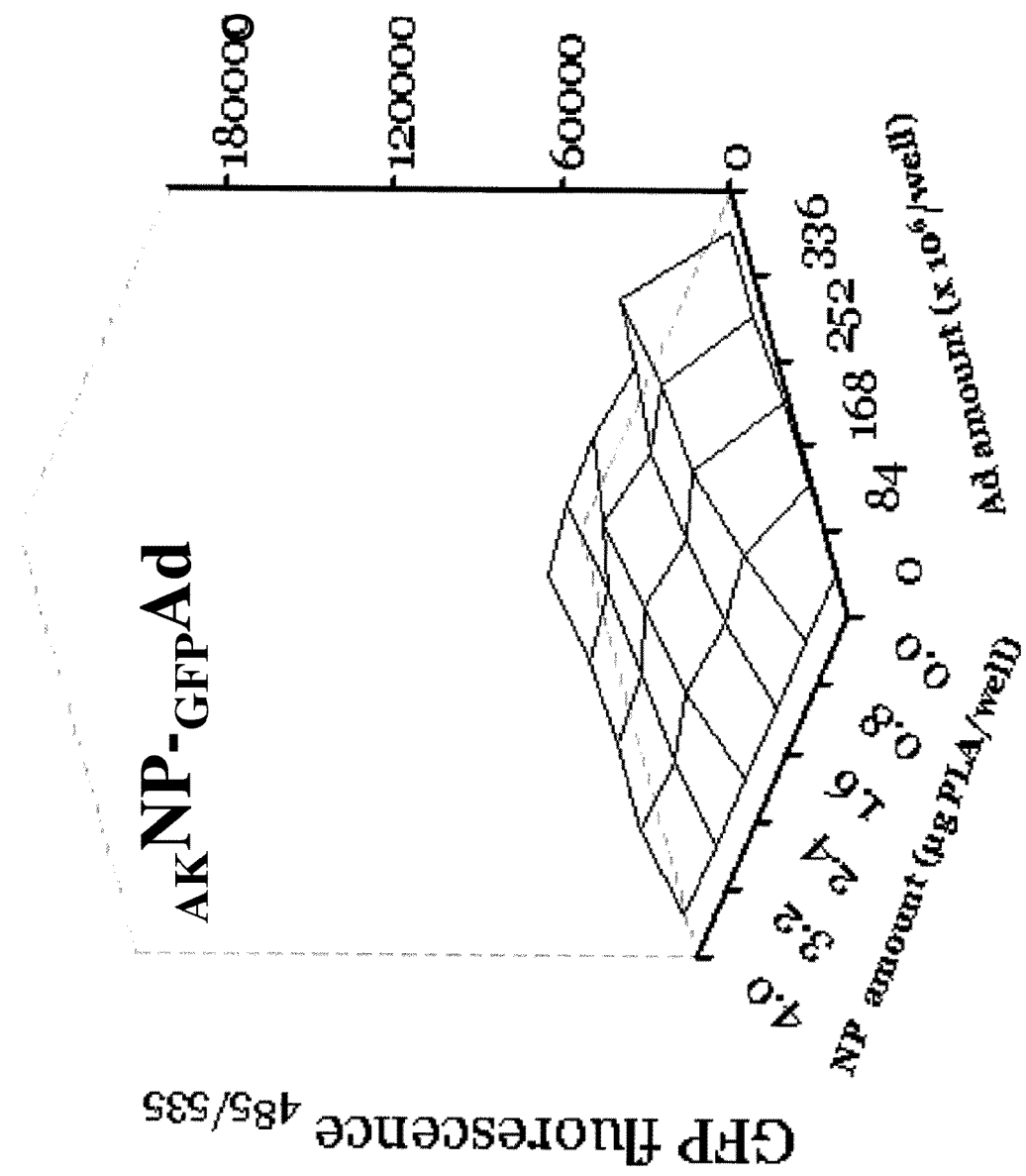
Figure 11B:
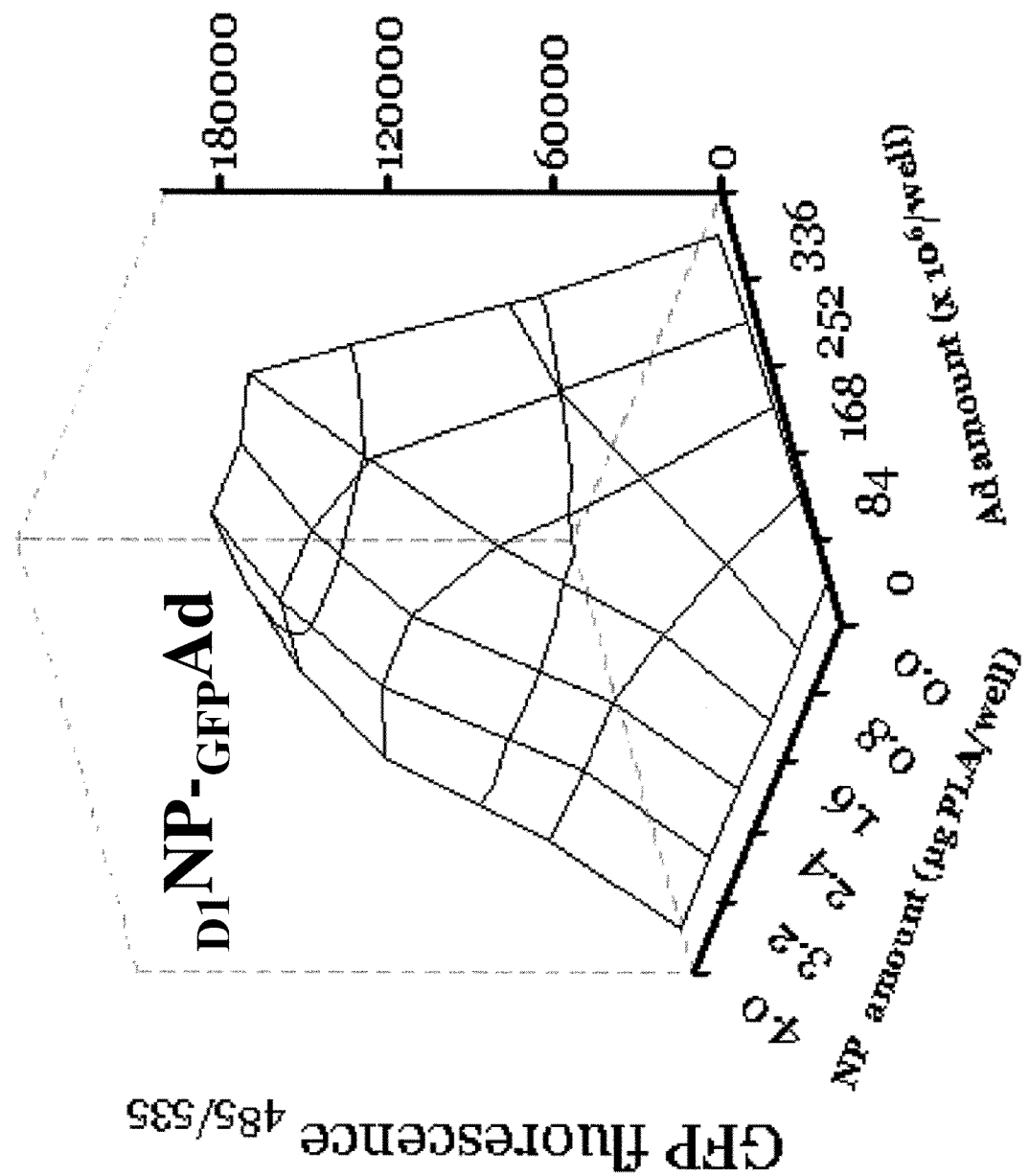

FIGS. 11A and 11B are 3D graphs demonstrating GFP expression as a function of NP and AdV dose with NP-Ad complexes employing anti-knob Ab ($_{AK}$NP-Ad) vs. D1 ($_{D1}$NP-Ad) as vector tethering agents respectively. The gene expression was assayed in A10 cells 48 hr post treatment.

Figure 12:
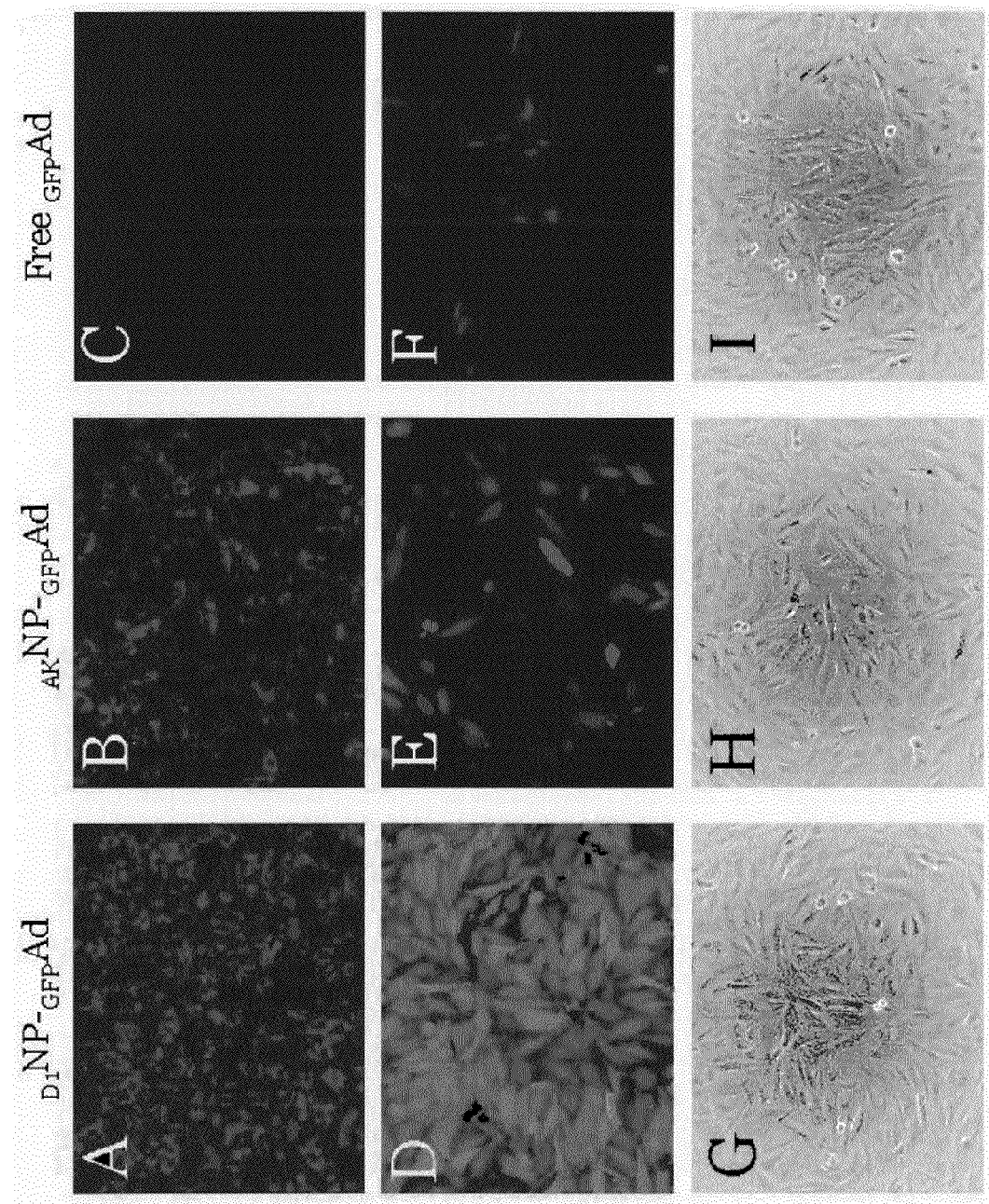

FIG. 12 shows micrographs demonstrating NP-Ad uptake and GFP expression in A10 cells employing D1 ($_{D1}$NP-Ad, first column, A, D, and G) and anti-knob Ab ($_{AK}$NP-Ad, second column, B, E, and H) with free $_{GFP}$Ad (third column, C, F, and I) included as a control. The respective NP at a dose of 4.0 μg PLA/well were incubated with Ad at a dose $3.6 \times 10^8$ viral particles/well and added to the cells for 2 hr. Free Ad was included as a control (third column). The upper row shows the cell uptake of the complexes visualized using red fluorescent-labeled NP (A, B) and the respective GFP expression (D, E) observed 48 hr post treatment. The perinuclear localization pattern and the substantially higher amount of the red fluorescence associated with $_{D1}$NP-Ad vs. $_{AK}$NP-Ad complexes (A vs. B) that corresponds to a qualitatively higher level of GFP expression in $_{D1}$ NP-Ad-treated cells (D vs. E) was observed. The absence of red fluorescence in the cells treated with free Ad (C) was observed. The A10 cells treated with NP-Ad and the free Ad exhibited no change in their characteristic morphology (G-I) consistent with a lack of toxic effects. The original magnification was ×100.

Figure 13:
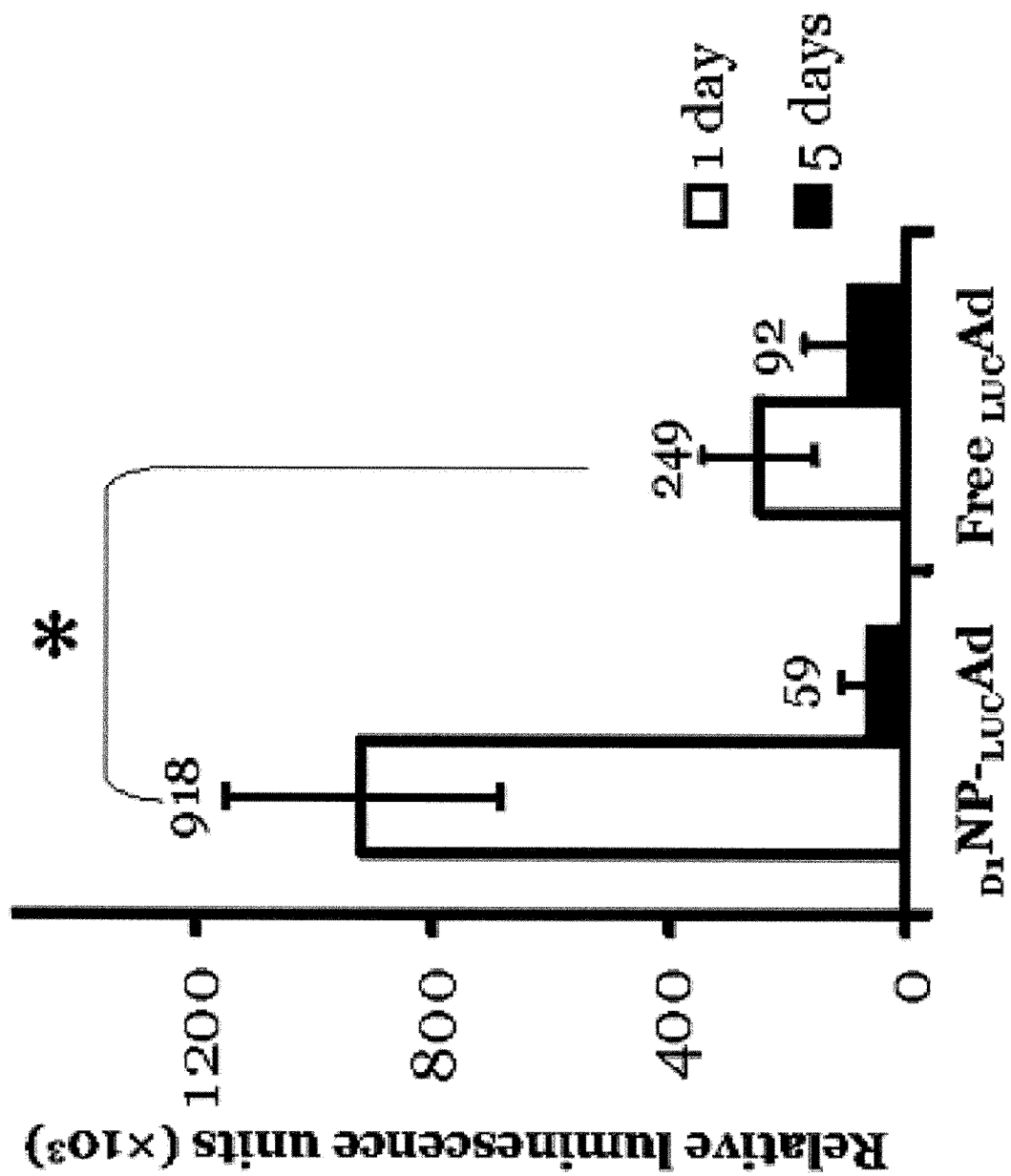

FIG. 13 is a bar graph demonstrating luciferase (LUC) gene expression in vivo in rat subcutaneous injection studies. $_{D1}$NP-Ad complexes were formed by incubating $_{LUC}$Ad with $_{D1}$NP for 60 minutes followed by injection in rats at a dose $8 \times 10^9$ Ad and 150 μg PLA in 100 μl suspension per animal (n=4). Five control animals received an identical dose of free $_{LUC}$Ad. Luciferase expression was measured in vivo assaying bioluminescence at 1 and 5 days post treatment (A). A significantly greater LUC expression was observed with NP-$_{LUC}$Ad than $_{LUC}$Ad at one day (p=0.016), but not 5 days. Representative bioluminescence images taken at 1 day time point (not shown) demonstrate focal luciferase gene expression with characteristic concentrical distribution around the injection site with more intense LUC activity in the NP-$_{LUC}$Ad group at 1 day.

FIG. 14 is a scheme demonstrating synthesis of photoreactive polymers: poly(allylamine)-benzophenone-pyridyldithio-carboxylate (PBPC) and poly(allylamine)-benzophenone-maleimido-carboxylate (PBMC).

Figure 15A:
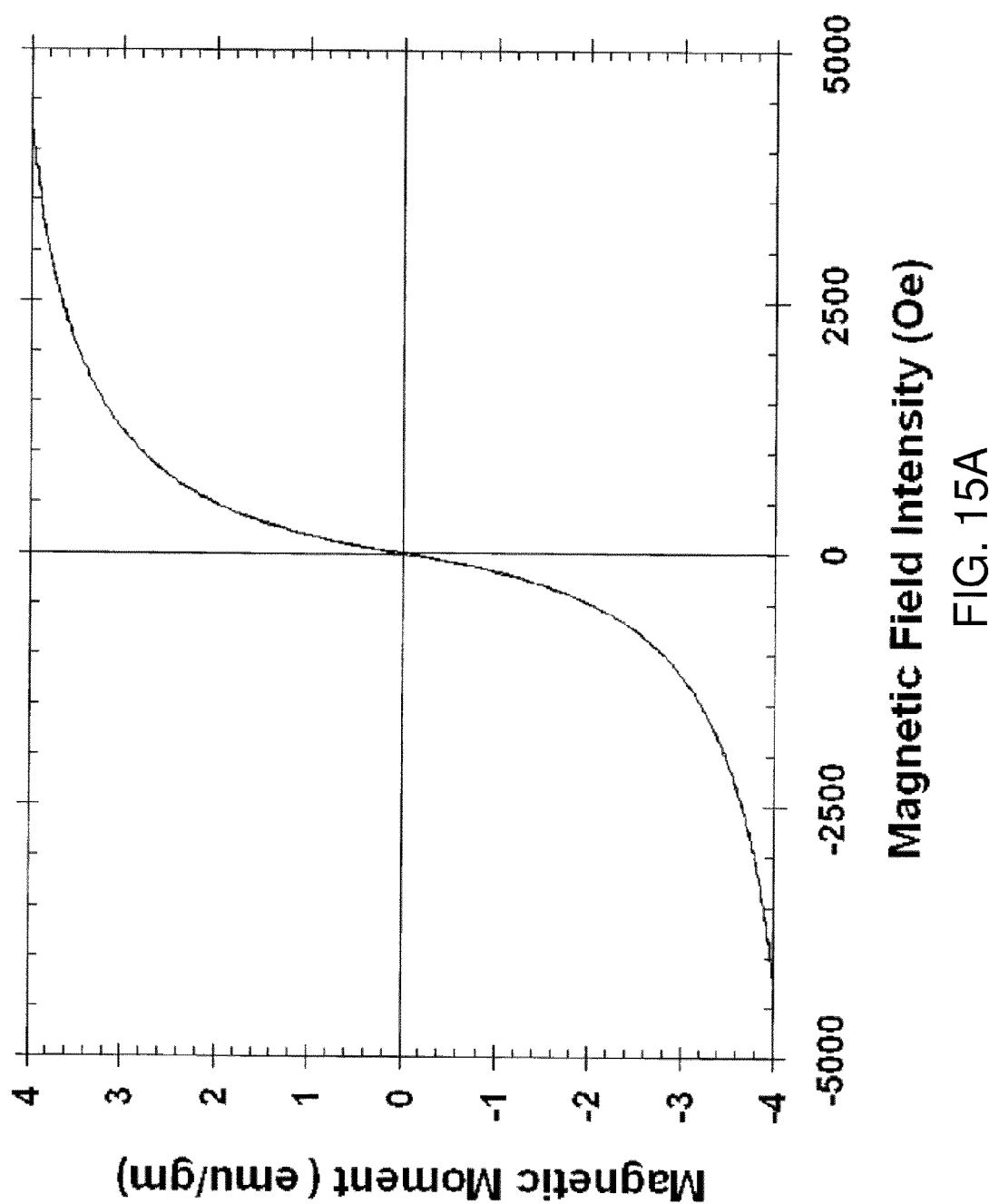
Figure 15B:
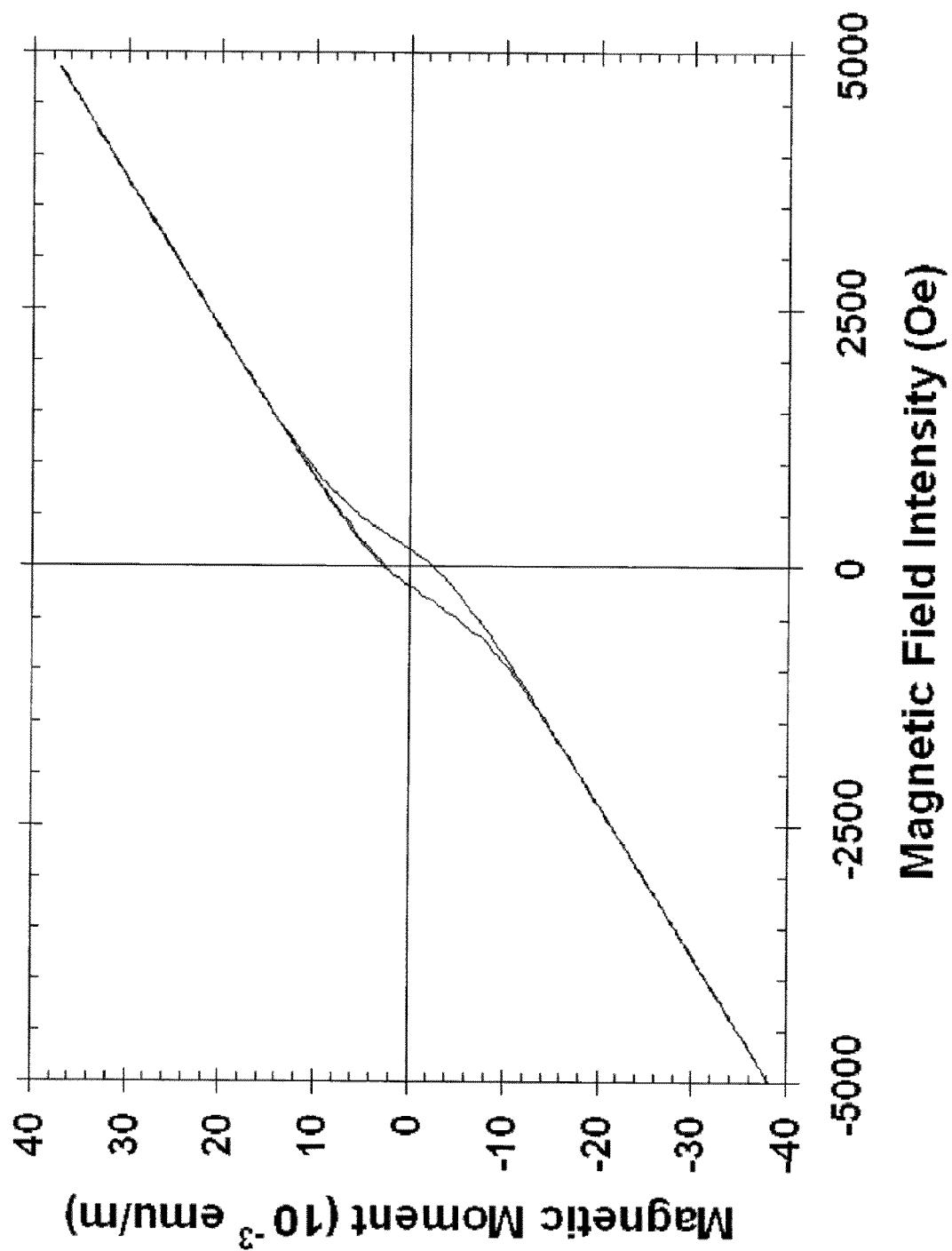
Figure 15C:
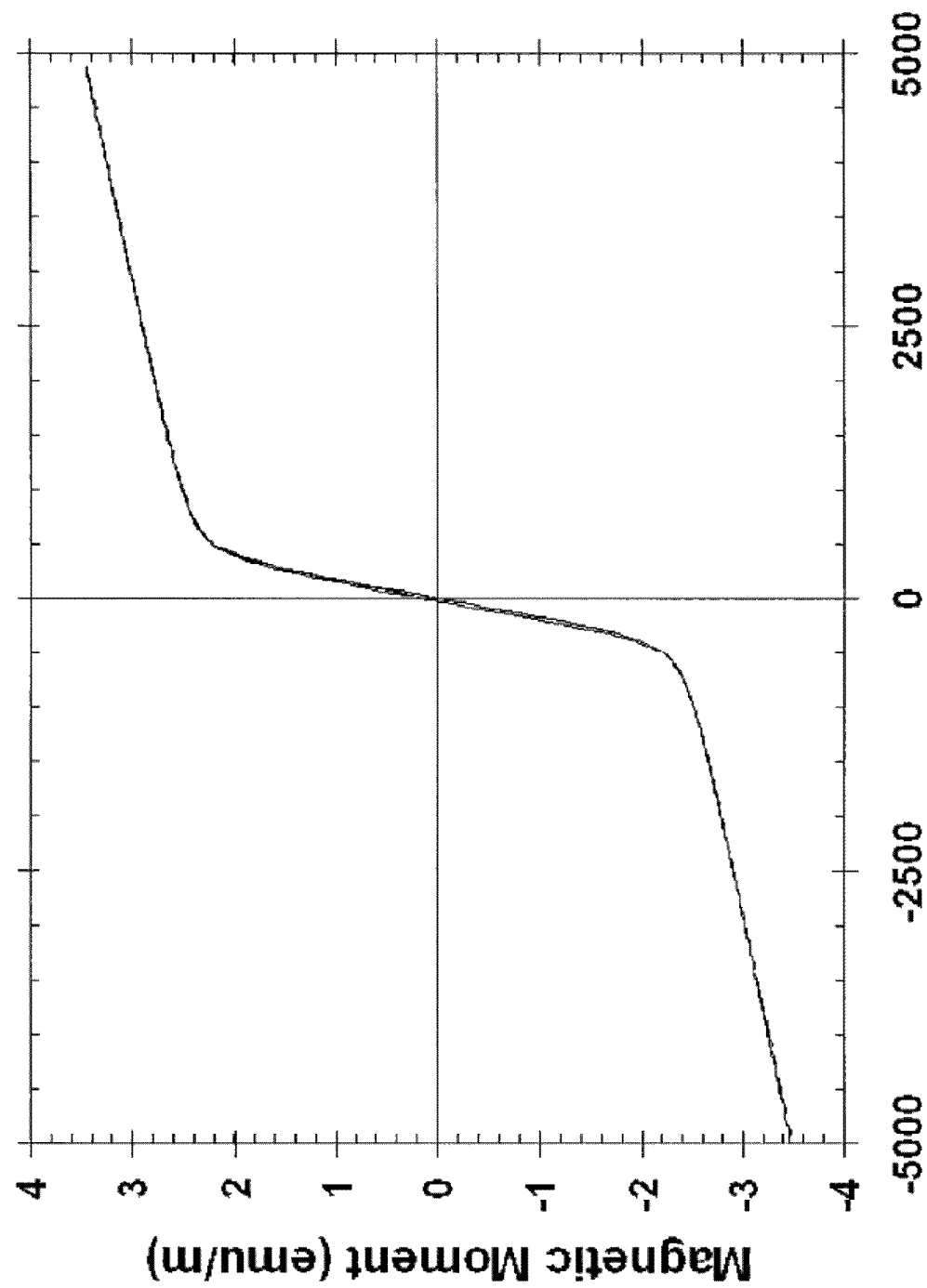

FIGS. 15 A-C are hysteresis curves for magnetic nanoparticles (FIG. 15A), 3.5 mm long segment of Palmaz-Shatz stent wire (FIG. 15B), and 3.5 mm long segment of Palmaz-Shatz stent wire coated with Nickel/Cobalt alloy (FIG. 15C). The linear region of the curve below 1000 Oerstads was used to determine the susceptibility of the nanoparticles and the normalized magnetic moment per unit length of the wires.

Figure 16A:
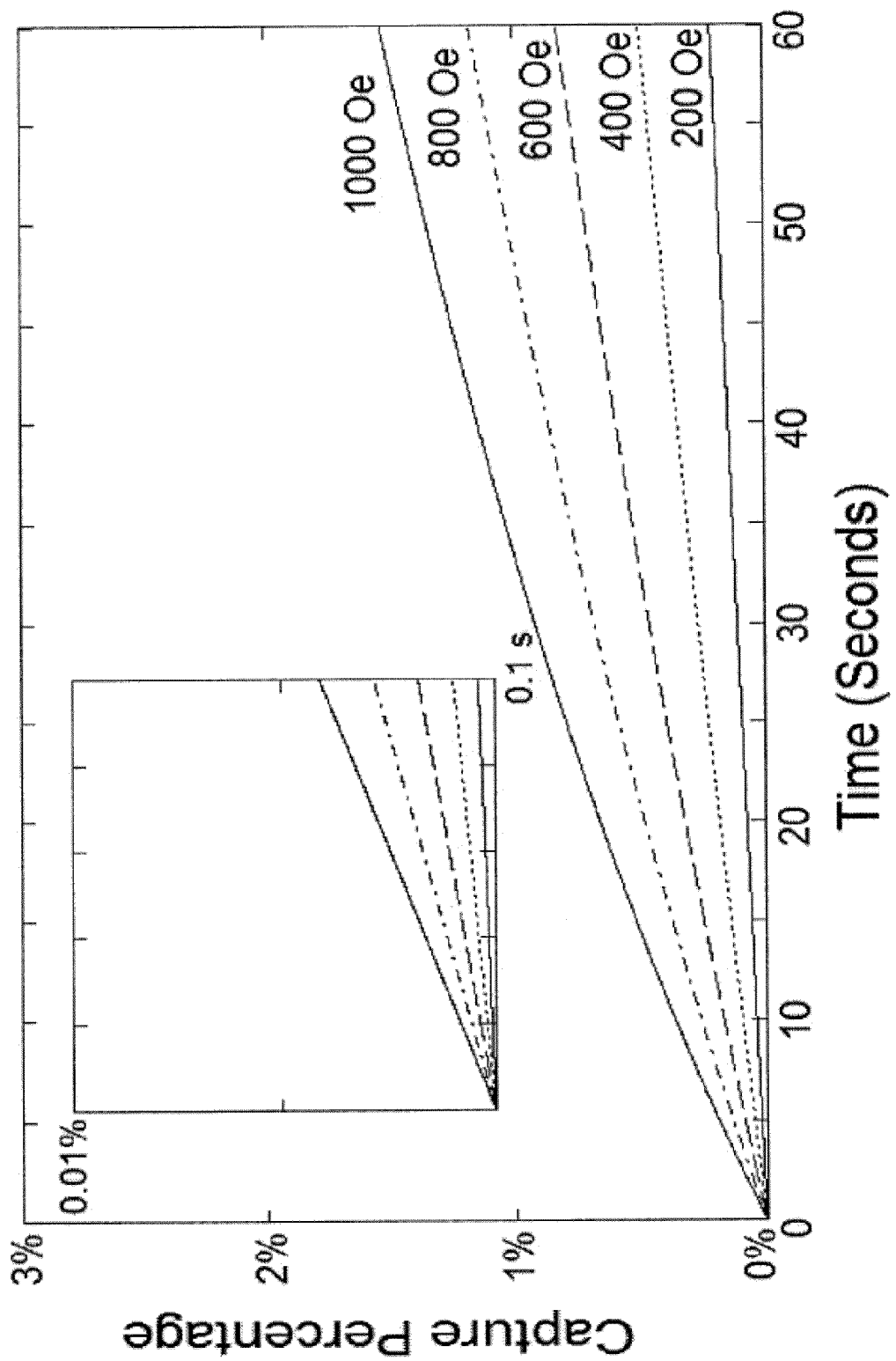
Figure 16B:
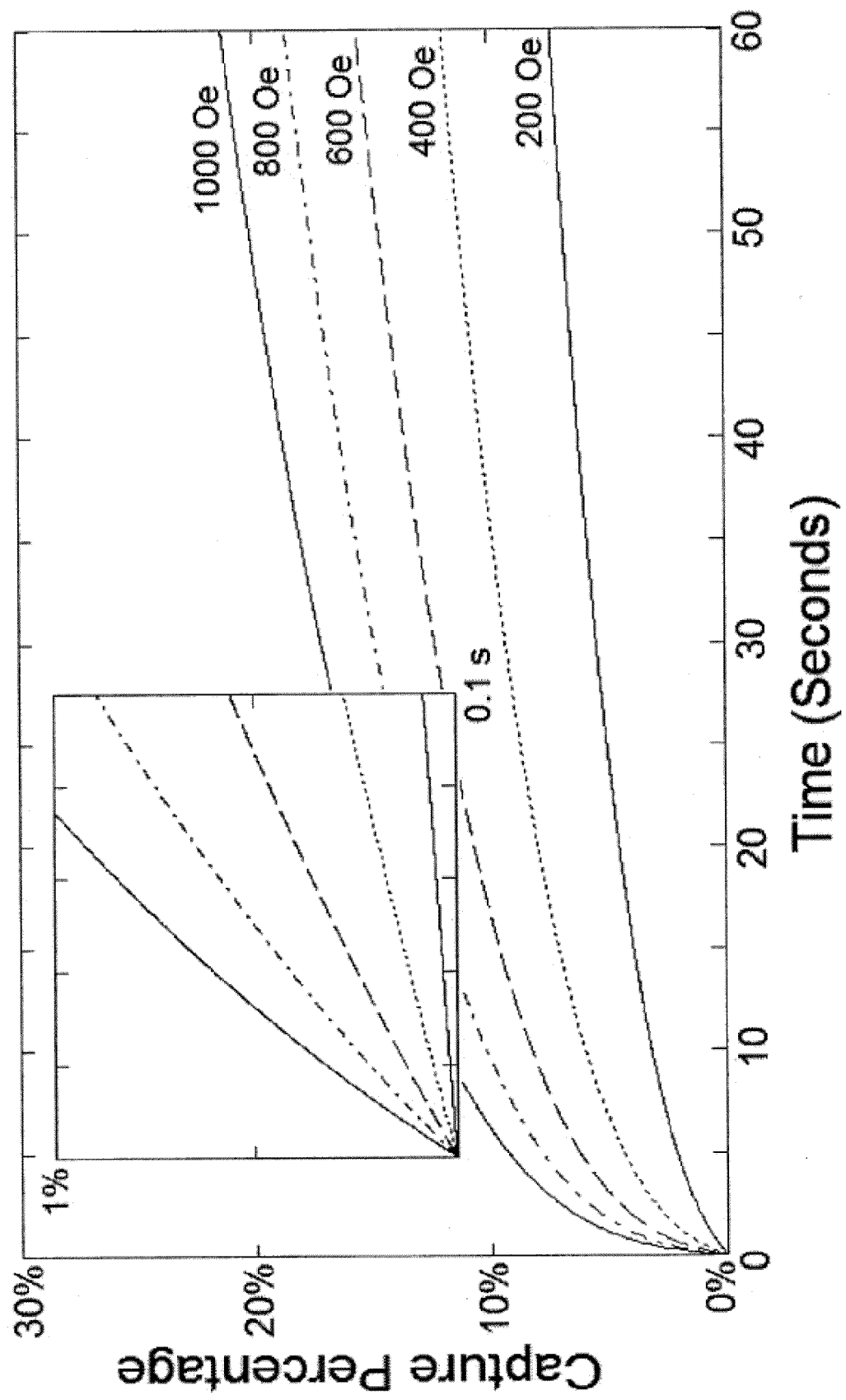
Figure 16C:
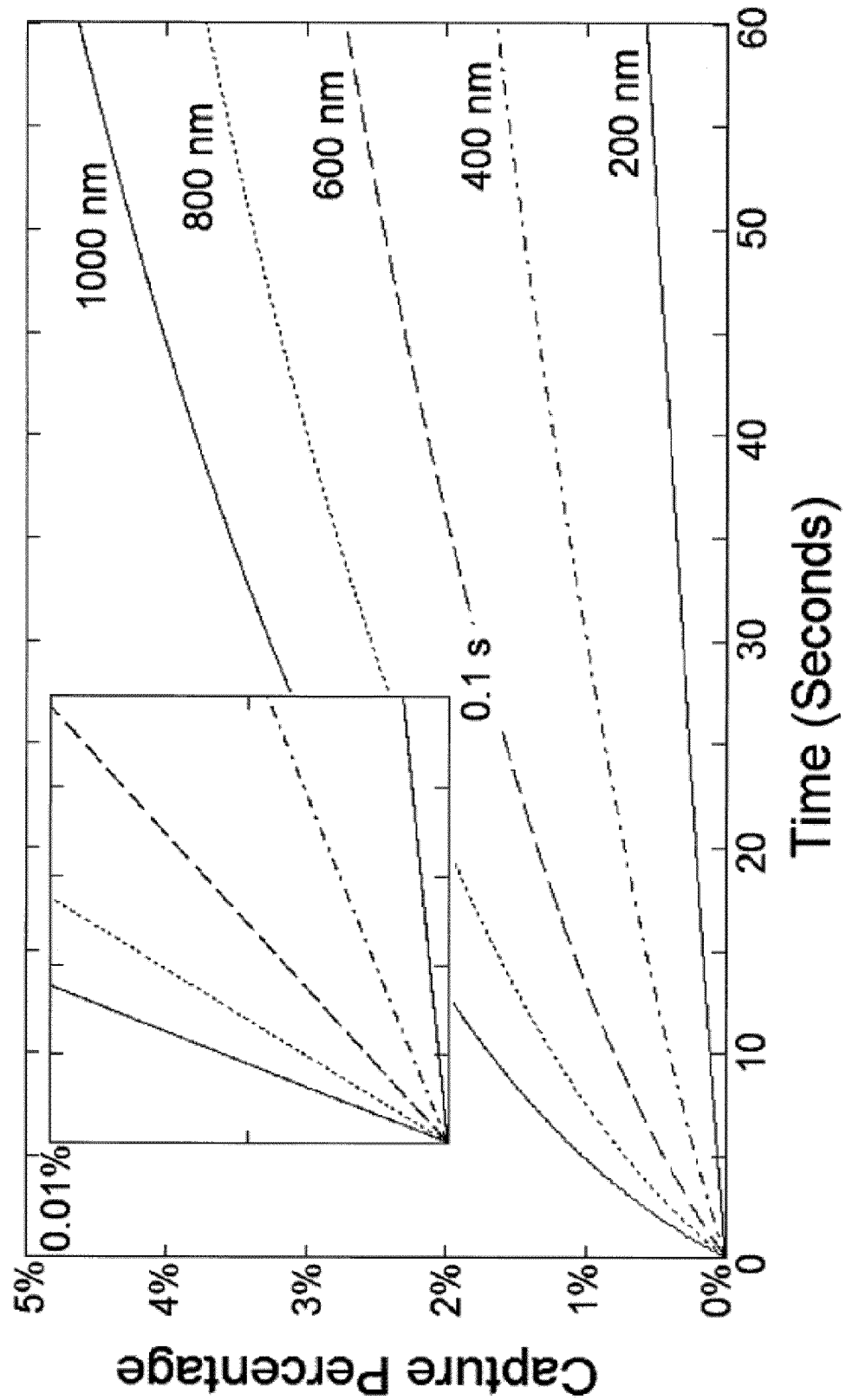

FIGS. 16A-C are graphs demonstrating simulated capture profiles of magnetic nanoparticles on implant materials as a function of time, applied field strength, and nanoparticle diameter. The capture percentage of 380 nm diameter magnetic nanoparticles on unmodified Palmaz-Shatz 316L stent wire as a function of the applied field is shown in FIG. 16A, whereas the capture percentage on Nickel/Cobalt coated Palmaz-Shatz 316L stent wire under similar conditions is shown in FIG. 16B. The capture percentage on unmodified Palmaz-Shatz 316L stent wire in 1000 Oerstad fields as a function of nanoparticle diameter is shown in FIG. 16C. In each graph, the inlay shows the capture dynamics over the first 100 milliseconds, indicating the potential for capturing particles by intravenous injection in normal blood flow.

Figure 17A:
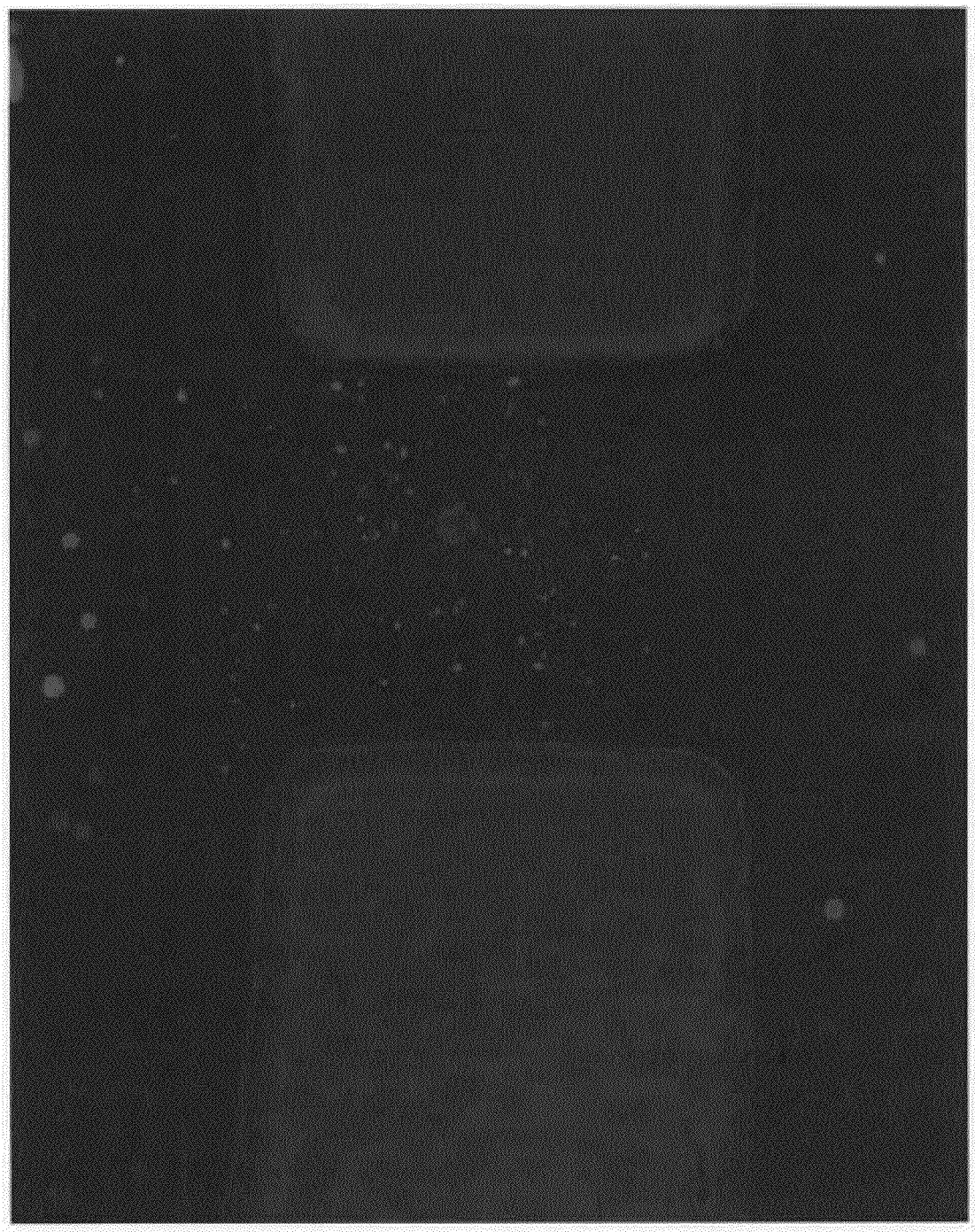
Figure 17B:
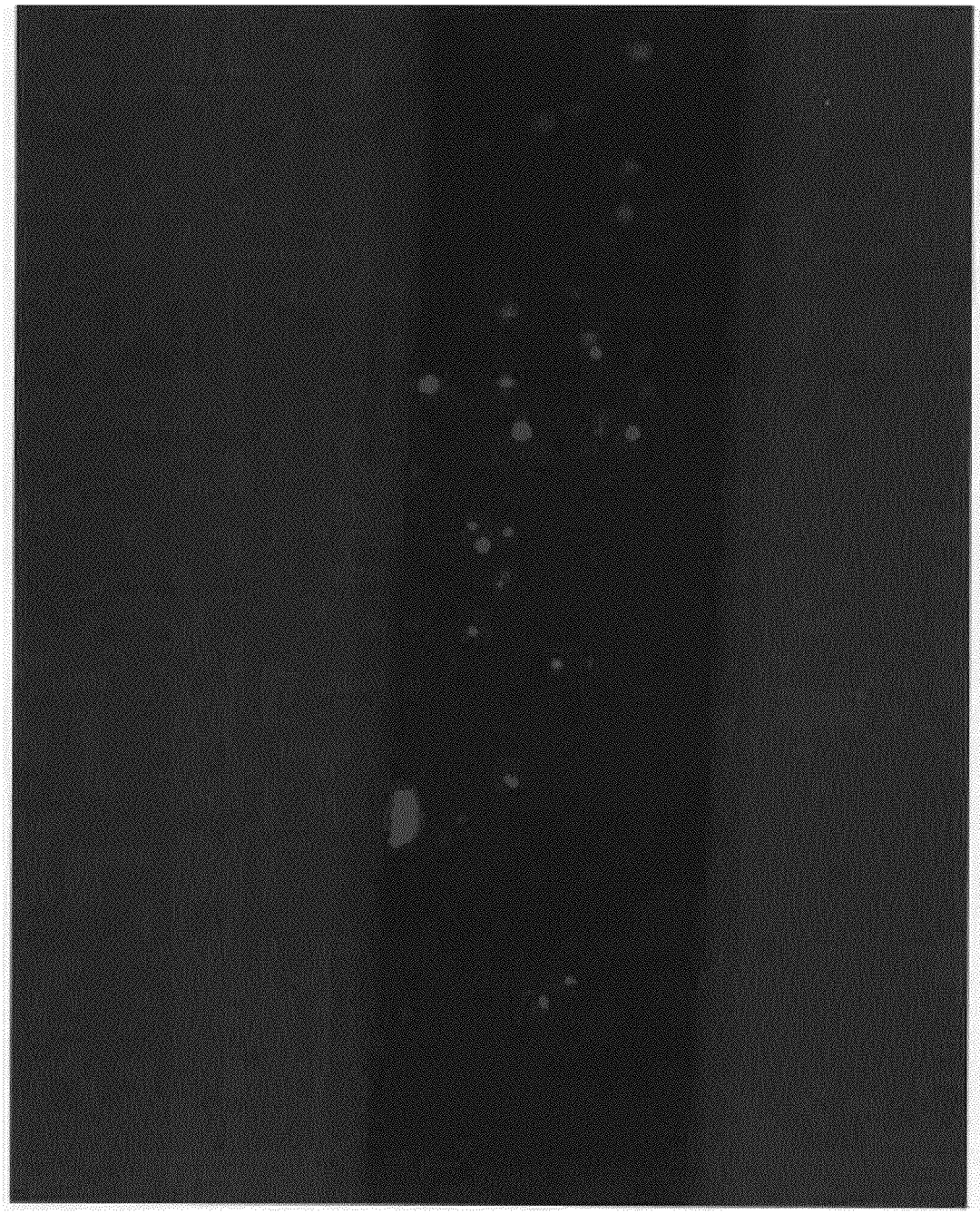
Figure 17C:
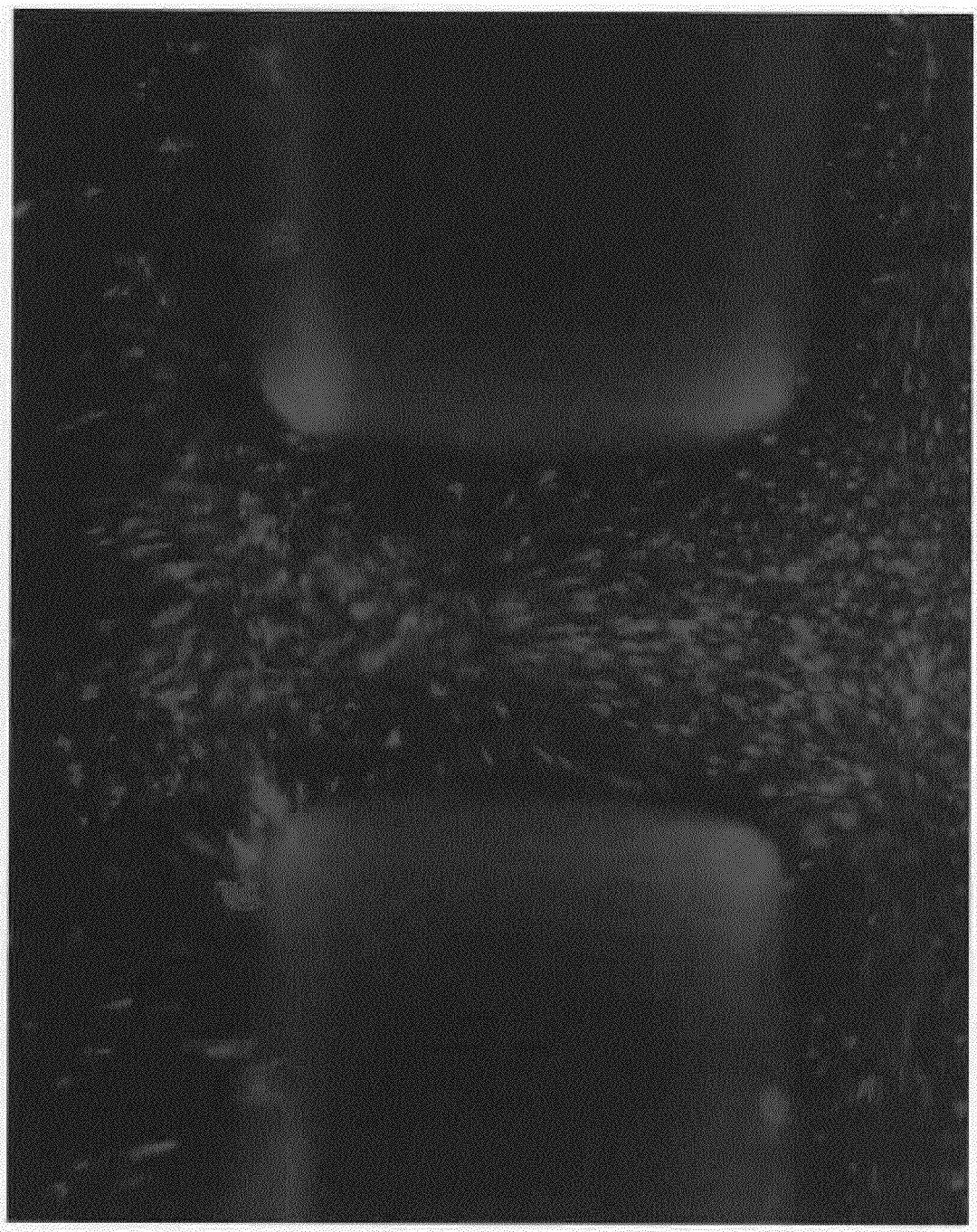
Figure 17D:
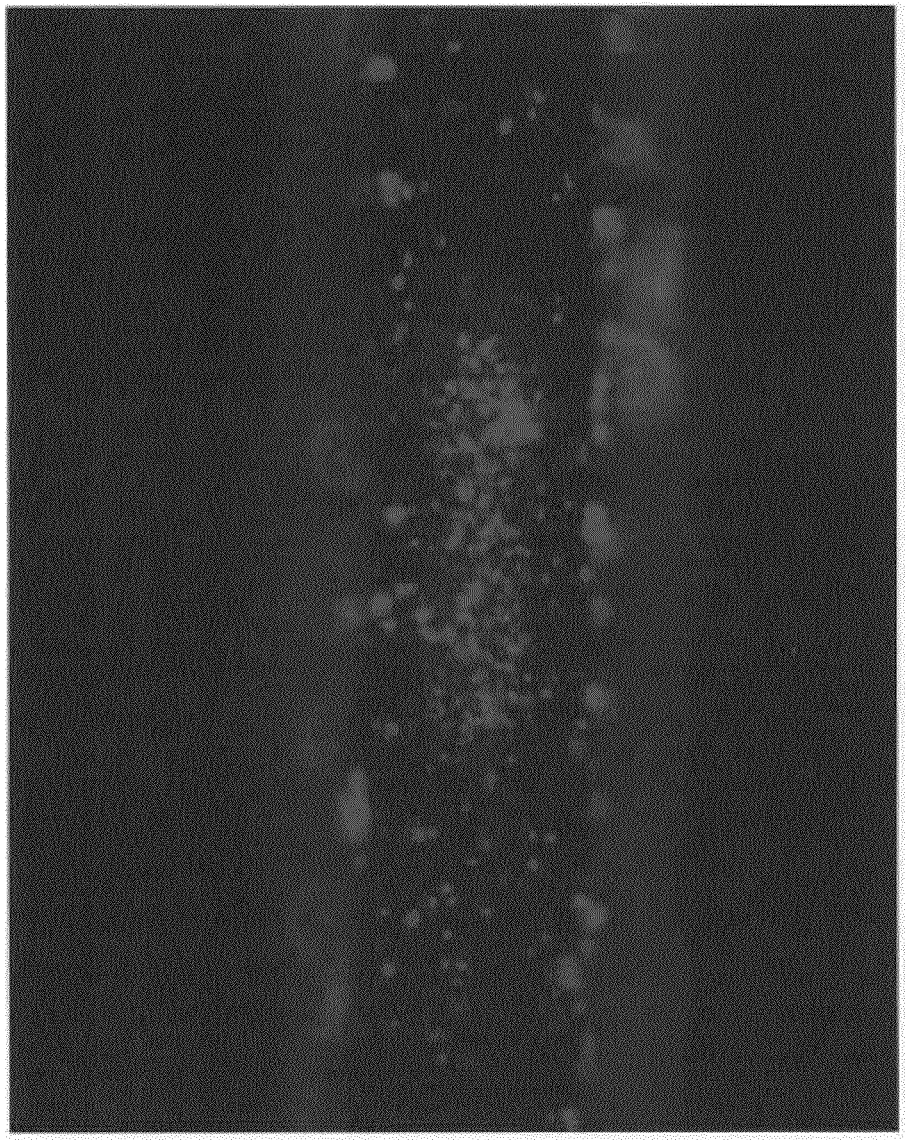
Figure 17E:
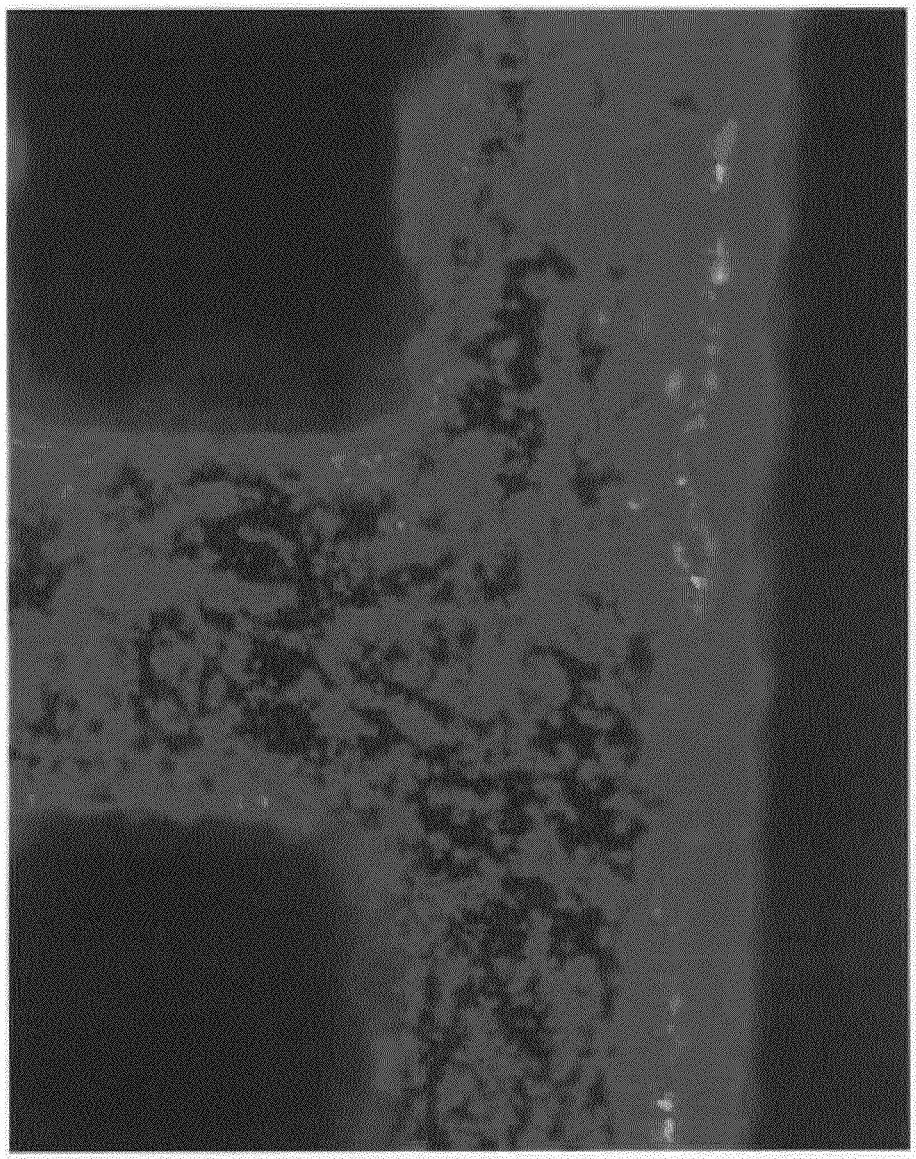
Figure 17F:
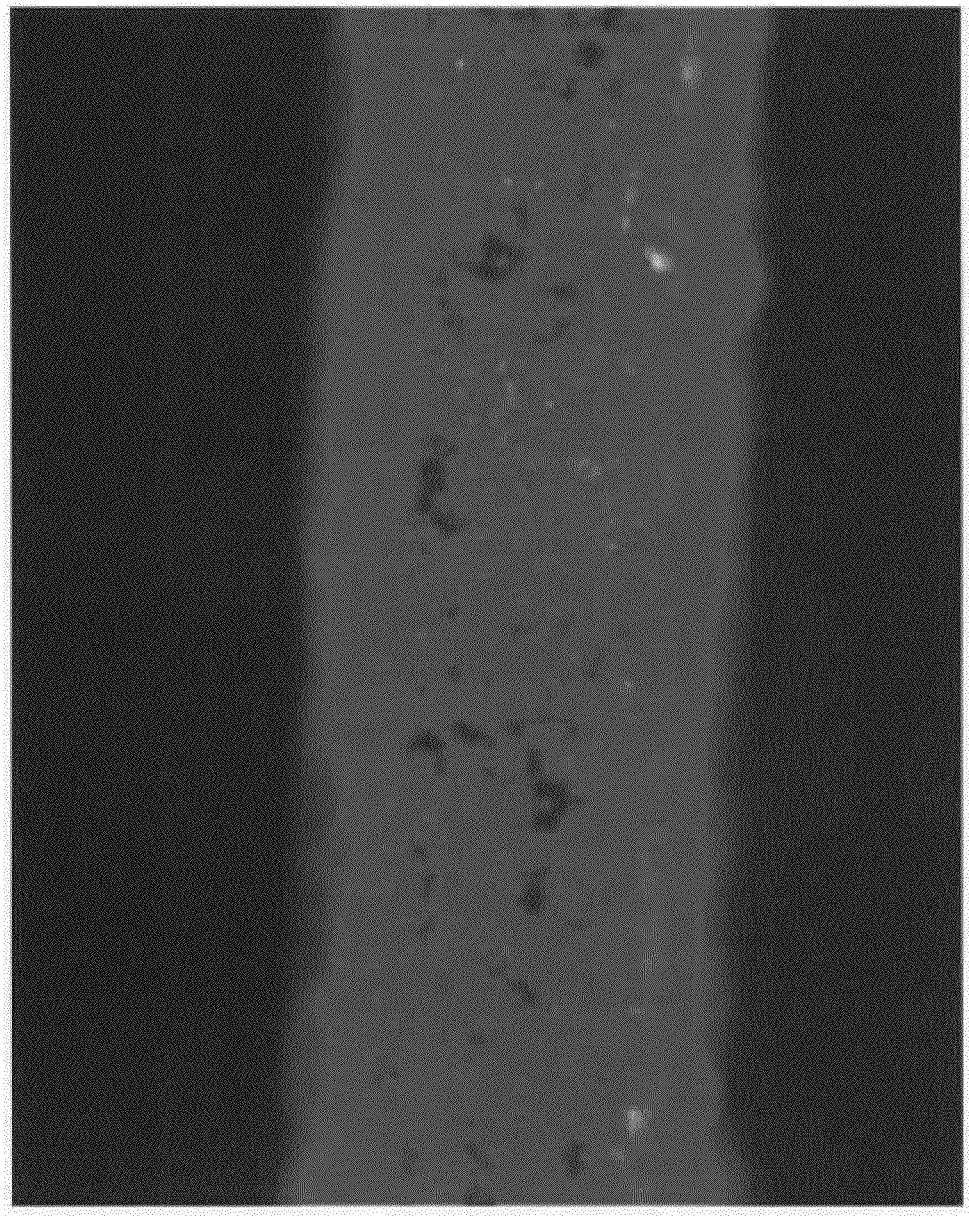

FIGS. 17A-17F are fluorescent images demonstrating the particle capture on 316L stent wires. FIGS. 17A-B show the nanoparticle accumulation on unmodified 316L stents without exposure to external field. FIGS. 17 C-D show the nanoparticle accumulation on unmodified 316L stents subjected to a 1000 Oerstad external field. FIGS. 17 E-F show the nanoparticle accumulation on Nickel/Cobalt coated 316L stents subjected to a 1000 Oerstad external field. All scale bars were 100 mm.

Figure 18A:
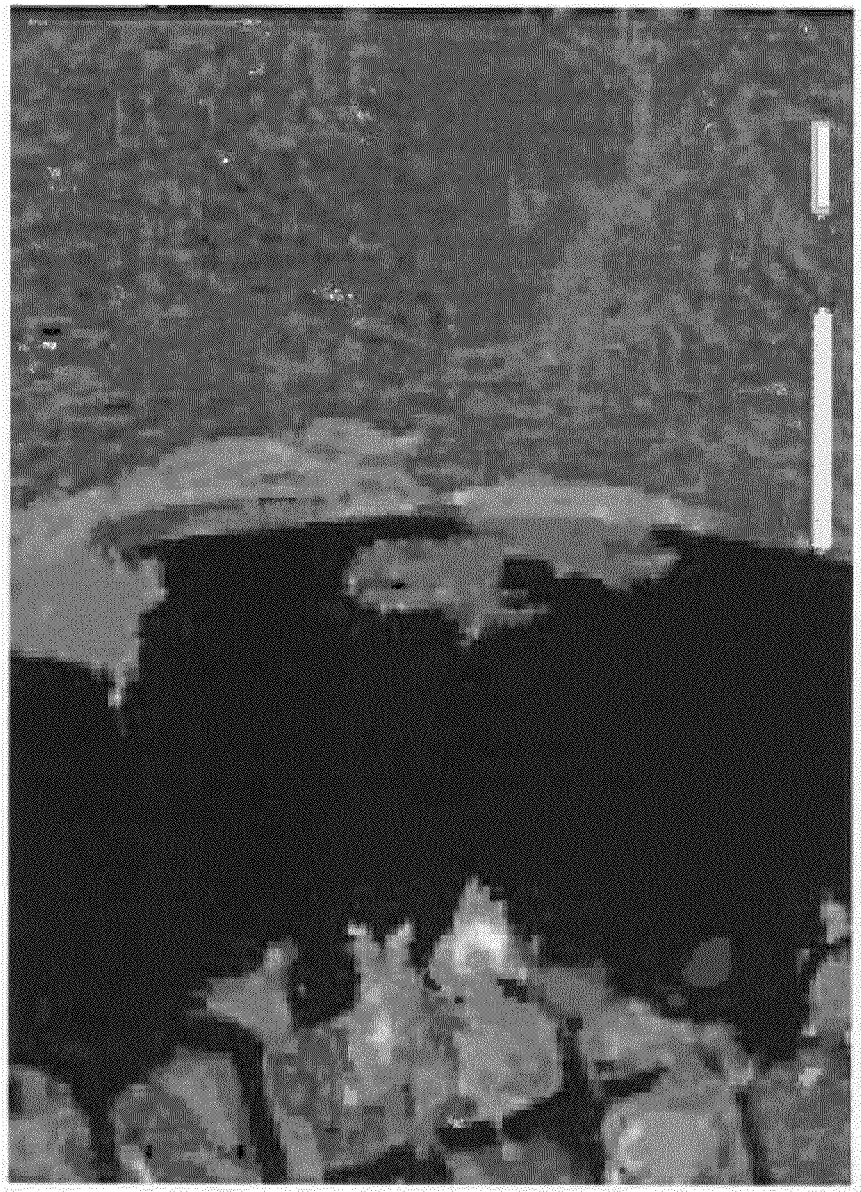
Figure 18B:
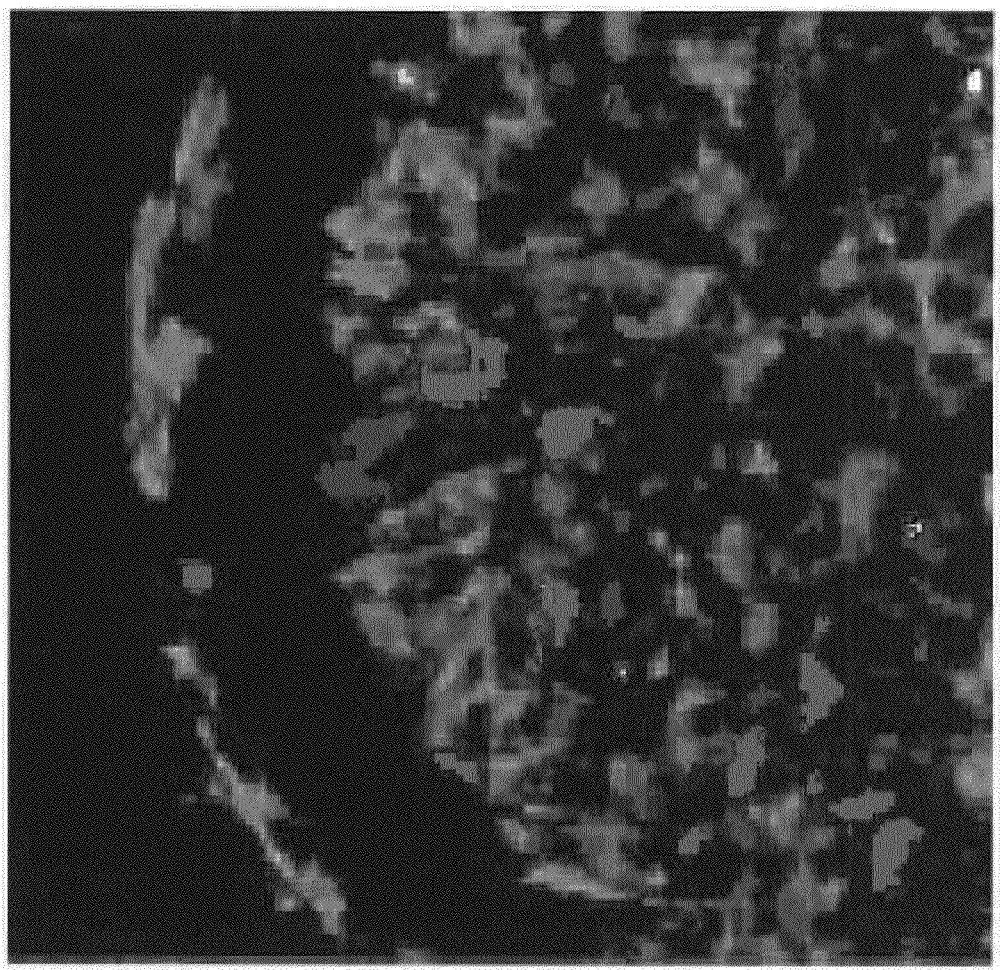
Figure 18C:
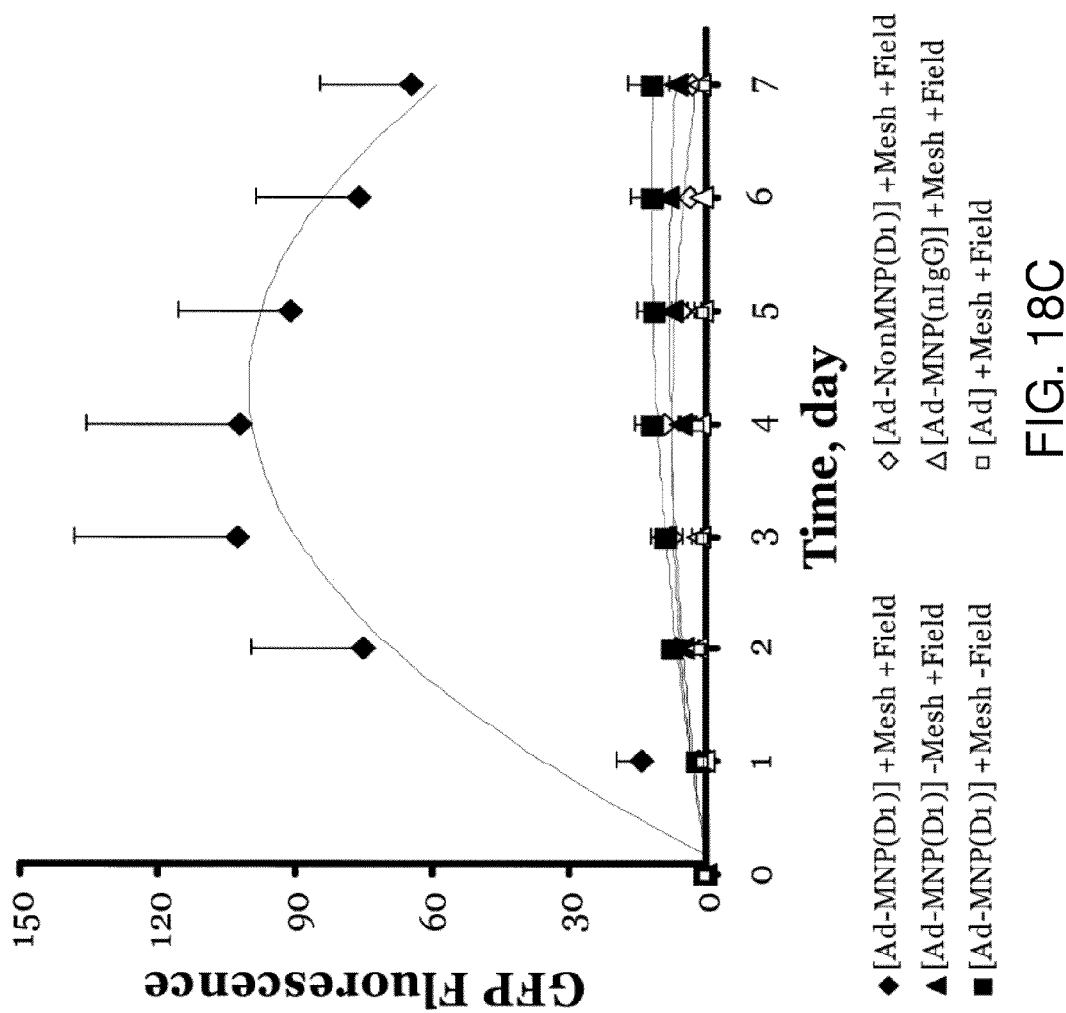

FIGS. 18A-B are micrographic images of GFP-adenovirus studies with magnetically responsive nanoparticle-adenoviral vector complexes, wherein FIG. 18A shows a closeup image of the transduction pattern in an A10 cell monolayer coated on a 316 Stainless Steel Electron Microscopy grid. The magnetic nanoparticles (red fluorescent) are co-localized in the GFP positive cells that are positioned on the mesh wires. A large area image of the transduction pattern in as shown in FIG. 18B confirms that the magnetic force direction is responsible for transfection of cells only nearby the mesh. All scale bars are 100 μm. FIG. 18C is a graph demonstrating gene expression over the course of seven days. All controls are negligible in comparison to the experimental group (black line).

Figure 19A:
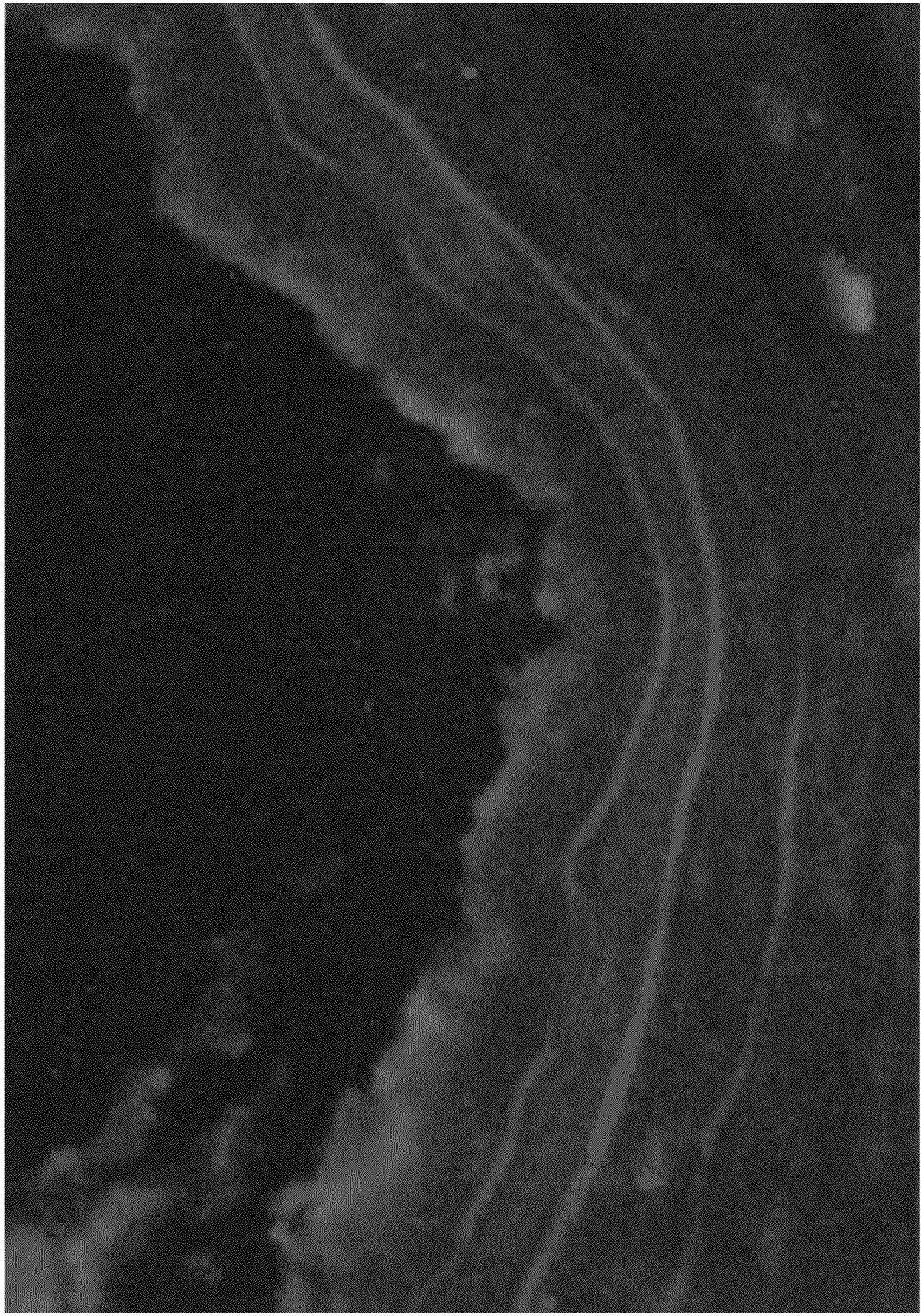

FIG. 19A is quantitative data documenting magnetically driven GFP expression in cell culture via the use of magnetically responsive nanoparticles with tethered GFP-adenoviruses in the presence of a field (versus all of the relevant controls) using the techniques illustrated in FIGS. 18A-C.

Figure 19B:
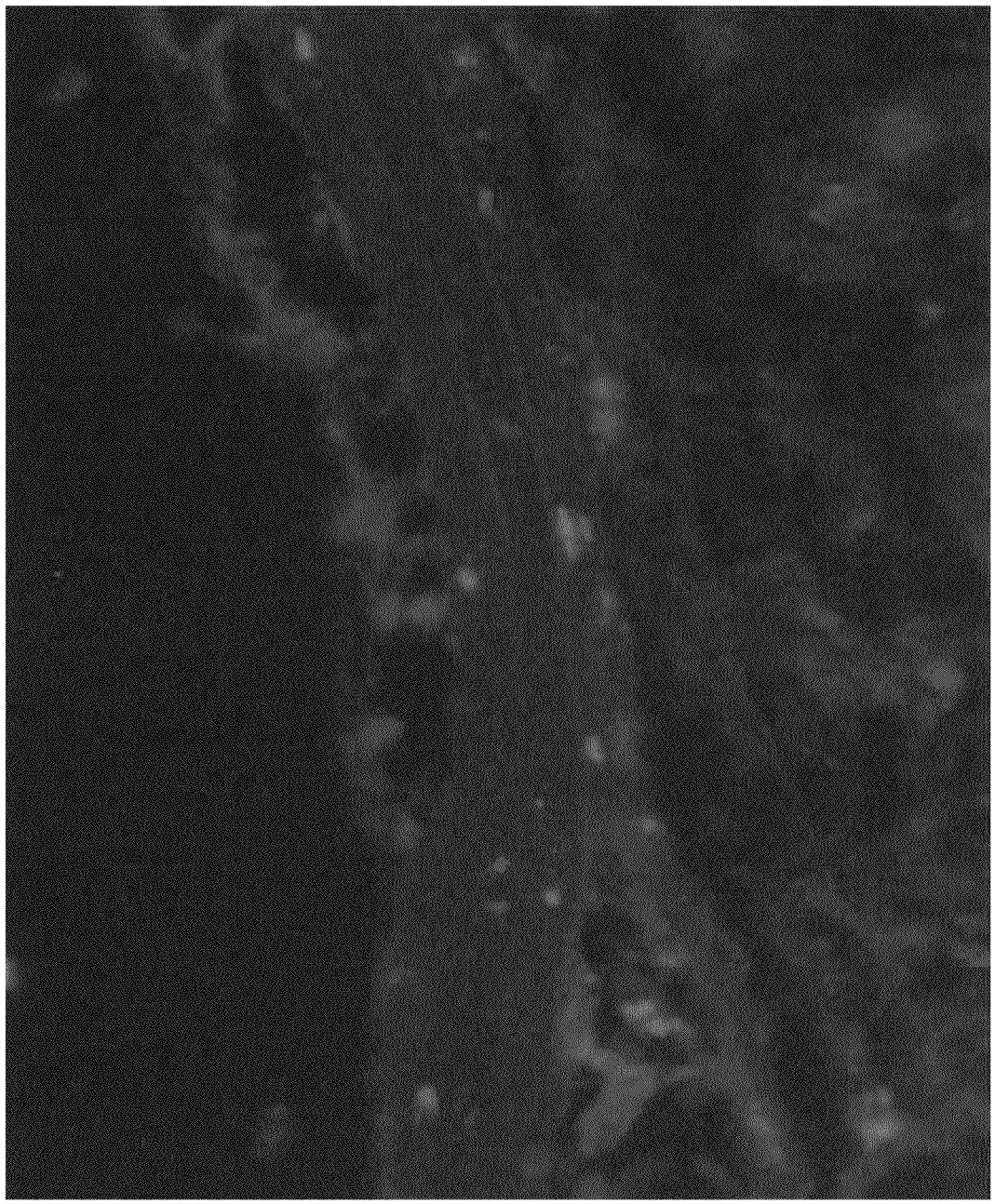

FIG. 19B demonstrates minimal GFP expression in a rat carotid artery with a steel coil deployed and injected with magnetically responsive nanoparticles with tethered GFP-adenoviruses, but without the use of a magnetic field, demonstrating little GFP expression.

Figure 19C:
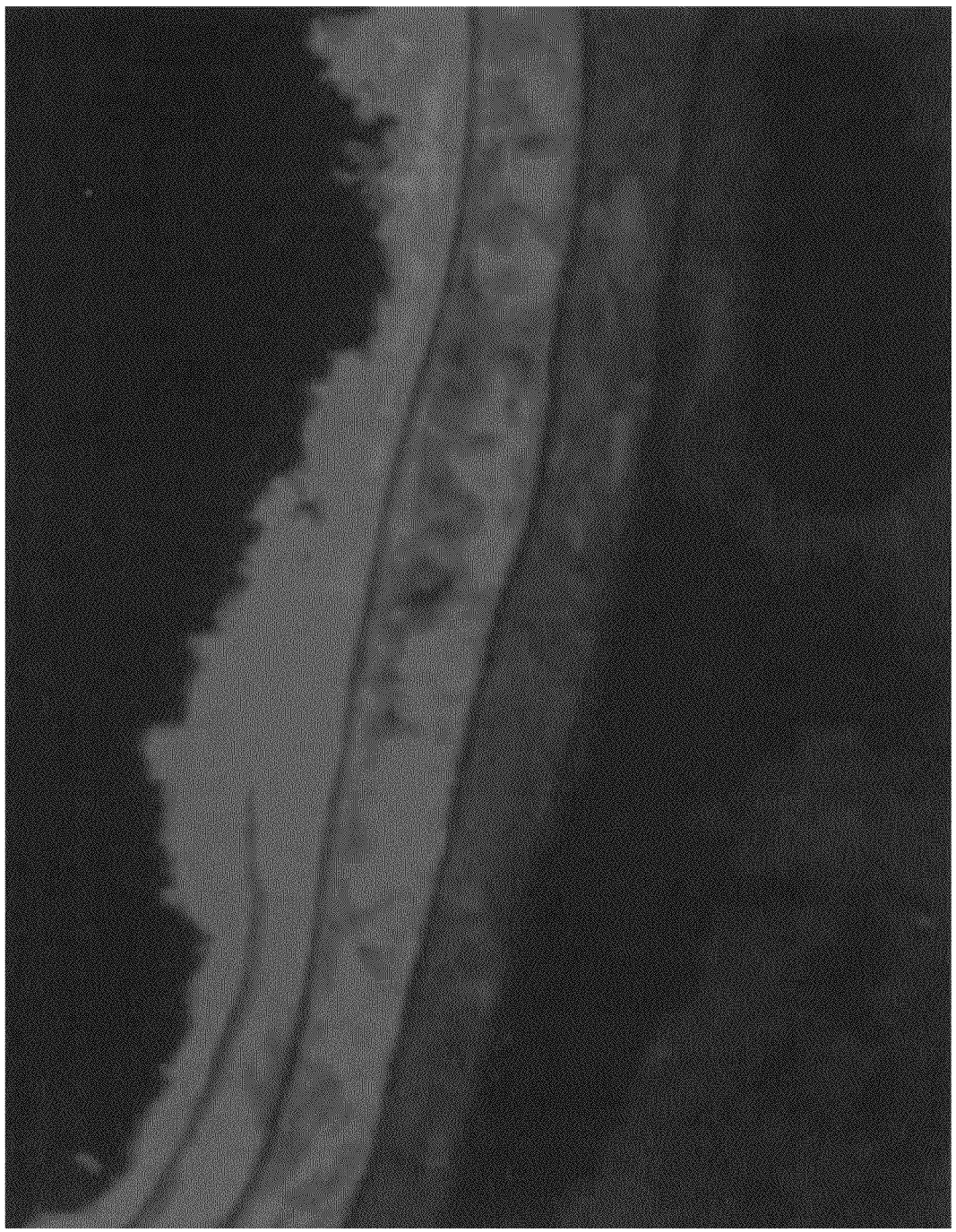

FIG. 19C demonstrates minimal GFP expression in a rat carotid artery with a steel coil deployed and injected with magnetically responsive nanoparticles with tethered GFP-adenoviruses, but with the use of a magnetic field demonstrating extensive GFP expression.

Figure 20:
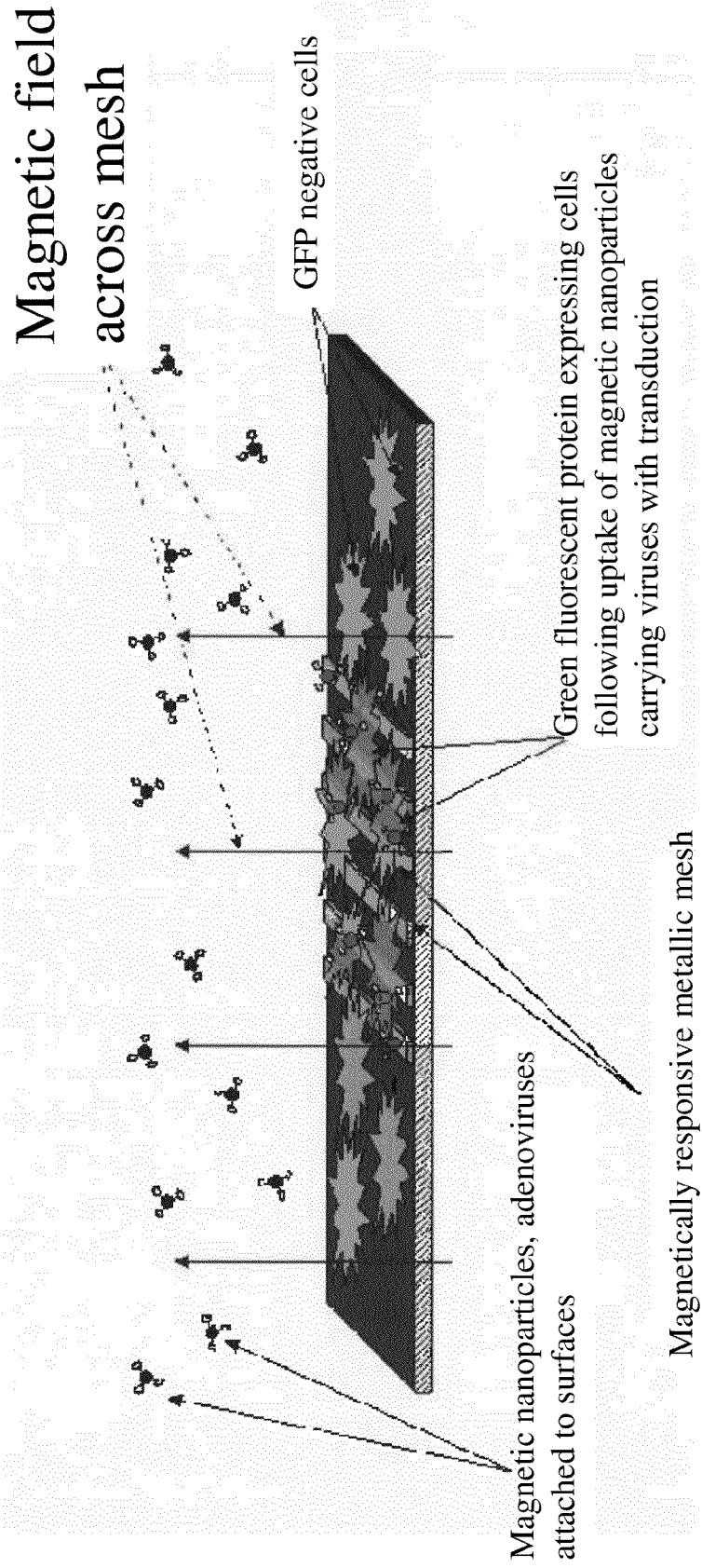

FIG. 20 is a schematic representation of the method of delivering magnetic nanoparticles carrying GFP encoding adenovirus to magnetic field gradients produced by 316L steel. The therapy (green glow) is delivered only to the cells growing on top of the 316L stent wires, in order to indicate the nature of local delivery method. The magnetic field across the mesh causes the development of high field gradients between the mesh wires which attracts and binds magnetically responsive nanoparticles.

DETAILED DESCRIPTION OF THE INVENTION

The invention was driven by the desire to develop a composition and a method for surface modification of inert surfaces useful for implantation, which would permit attachment of molecular therapeutics such as proteins, genes, vectors, or cells and avoid using organic solvents that can potentially damage both the surface and molecular therapeutics. Moreover, utilizing therapeutic potential of site-specific therapy (SST) with custom synthesized stent surfaces and heart valve leaflets, the present photochemical approach will permit surface activation of abroad range of existing medical device configurations.

The inventors have discovered that biomaterial can be covalently attached to surfaces having at least one carbon by utilizing a water-soluble photo-activatable polymer of the invention which functions as a multipoint polymeric cross-linker, wherein one function of the cross-linker is to photo-immobilize the water-soluble polymer to a desired surface and another function is to attach the desired biomaterial.

The water-soluble photo-activatable polymer of the invention comprises:

(a) a photo-activatable group, wherein the photo-activatable group is adapted to be activated by an irradiation source and to form a covalent bond between the water-soluble photo-activatable polymer and a matrix having at least one carbon;

(b) a reactive group, wherein the reactive group is adapted to covalently react with a biomaterial;

(c) a hydrophilic group, wherein the hydrophilic group is present in an amount sufficient to make the water-soluble photo-activatable polymer soluble in water; and (d) a polymer precursor.

The specific chemistry used herein has distinct advantages since it involves: 1) aqueous based exposures, thus removing any risk of damaging surfaces that could be susceptible to organic solvent damage, and 2) addition of reactive groups, e.g., PDT groups, thus enabling sulfhydryl chemistry approaches for attaching linking proteins and peptides, such as antibodies or receptor fragments.

A reaction between a thiol-reactive group (2-pyridyldithio, maleimide, etc.) attached to one protein molecule with a thiol group of another protein molecule (or other biomolecule) is widely used for preparation of protein conjugates (See Greg T. Hermanson, Bioconjugate Techniques, Academic Press, San Diego 1996). Reaction of a thiol group with most of thiol-reactive groups (particularly 2-pyridyldithio group) is very selective and fast in aqueous media at mild conditions. Proteins can be thiolated using a partial reduction of disulfide bridges or via thiolation of lysine residues with a variety of reagents (see Hermanson, pp. 57-70). The reaction of thiolated proteins with polymeric surfaces containing thiol-reactive groups would be ideal for the immobilization of proteins on polymeric supports. At the same time, there is no method for providing polymeric surfaces with such thiol-reactive groups. The present invention can efficiently solve this problem.

One of the reasons the surface-attachment of 2-pyridyldithio-groups (PDT-groups) to polymers via benzophenone photo-cross-linkers is not obvious is that PDT-groups are rather unstable and may not survive conditions of photo-immobilization wherein active, energy-rich species appear.

The invention will now be described in more detail below.

The term "photo-activatable group" used herein denotes chemical groups capable of generating active species such as free radicals, nitrenes, carbenes and excited states of ketons upon absorption of external electromagnetic or kinetic (thermal) energy. These groups may be chosen to be responsive to various portions of the electromagnetic spectrum, i.e., the groups responsive to ultraviolet, visible and infrared portions of the spectrum. The preferred photo-activatable groups of the invention are benzophenones, acetophenones and aryl azides. Upon excitation, photo-activatable groups are capable of covalent attachment to surfaces comprising at least one carbon such as polymers.

The water-soluble photo-activatable polymer of the invention may have one or more photo-activatable groups. In certain embodiments, the water-soluble photo-activatable polymers have at least one photo-activatable group per molecule. Preferably, the water-soluble photo-activatable polymers have a plurality of photo-activatable groups per molecule. More preferably, photo-activatable groups modify at least 0.1% of monomeric units of a polymer precursor, even more preferably at least 1%, and most preferably from about 20 to about 50%.

The irradiation source can be any source known in the art capable of emitting the light having a wavelength absorbable by the photo-activatable group of the invention. A UV-lamp is preferred when the benzophenone is used as the photo-activatable group.

The term "water-soluble polymer" as used in this disclosure means that the water-soluble photo-activatable polymer of the invention can be diluted with water to at least 1 wt % and preferably to at least 0.1 wt % to form a single phase at a temperature of 20° C., provided that water is essentially free of an organic co-solvent.

The terms "surface" or "matrix" as used interchangeably herein mean a surface having at least one carbon. In a preferred embodiment of the invention, the surface is a polymeric matrix. Other surfaces such as organosylated materials (e.g., organosylated metals) can also be used in the present invention.

The surface contemplated by the present invention can have any shape or form suitable for variety of purposes such as, for example, delivery of a biomaterial to an organism. In that, the surface can be an existing medical implant such as a stent or a cardiovascular valve, which can be covered with the composition of the invention. Also, the surface can be first modified with either the water-soluble polymer of the invention or the composition of the invention and then molded into the desired shape. Moreover, the surface can be in a form of polymeric particles.

Medical devices appropriate for the gene delivery system in the present invention include, but are not limited to, heart valves, wire sutures, temporary joint replacements and urinary dilators. Other suitable medical devices for this invention include orthopedic implants such as joint prostheses, screws, nails, nuts, bolts, plates, rods, pins, wires, inserters, osteoports, halo systems and other orthopedic devices used for stabilization or fixation of spinal and long bone fractures or disarticulations. Other devices may include non-orthopedic devices, temporary placements and permanent implants, such as tracheostomy devices, jejunostomy and gastrostomy tubes, intraurethral and other genitourinary implants, stylets, dilators, stents, vascular clips and filters, pacemakers, wire guides and access ports of subcutaneously implanted vascular catheters.

The polymeric matrix of the invention can be biodegradable and non-biodegradable. Non-limiting examples of the polymeric matrix used in the invention are poly(urethane), poly(ester), poly(lactic acid), poly(glycolic acid), poly(lactide-co-glycolide), poly(ϵ-caprolactone), poly(ethyleneimine), poly(styrene), poly(amide), rubber, silicone rubber, poly(acrylonitrile), poly(acrylate), poly(metacrylate), poly (alpha-hydroxy acid), poly(dioxanone), poly(orthoester), poly(ether-ester), poly(lactone), mixtures thereof and copolymers of corresponding monomers.

In certain embodiments of the composition, the matrix further comprises a magnetic field-responsive agent. In certain embodiments, the magnetic field-responsive agent is a superparamagnetic agent. Preferably, the superparamagnetic agent is a member selected from the group consisting of magnetite and maghemite nanocrystals.

The water-soluble photo-activatable polymer of the invention comprises a polymer precursor and the following groups covalently attached to the polymeric precursor: the photo-activatable group as described above, a reactive group, and a hydrophilic group.

The polymeric precursor of the water-soluble photo-activatable polymer of the invention can be prepared using methods known in the art from a polymer (biodegradable or a non-biodegradable) comprising reactive groups and hydrophilic groups, which is then modified to contain photo-activatable groups (e.g., see Example 1). Non-limiting examples of such precursors are polymers containing monomers such as allylamine, vinylamine, acrylic acid, carboxylic acid, alcohol, ethylene oxide, and acyl hydrazine. Preferably, the polymer precursor is poly(allylamine) or poly(acrylic acid). In certain embodiments of the invention, the poly(allylamine) has a molecular weight of about 5 KDa to about 200 KDa. In the preferred embodiment, the molecular weight is from 15 KDa to 70 KDa.

Also, it can be prepared by polymerization of monomeric blocks containing the above groups. Such methods are also known in the art. In certain embodiments of the invention, the polymeric precursor comprises at least one monomer selected from the group consisting of allylamine, vinylamine, acrylic acid, carboxylic acid, alcohol, ethylene oxide, and acyl hydrazine.

The reactive group of the water-soluble photo-activatable polymer of the invention is a chemical group which is selected for its ability to covalently react with a biomaterial. A person skilled in the art would understand that if a thiol reactive group is selected as reactive group of the water-soluble photo-activatable polymer, a corresponding thiol group should be selected for a reactive group in the biomaterial. Non-limiting examples of the reactive group are an amino group (primary or secondary), a thiol-reactive group, a carboxy group, a thiol group, a protected thiol group, an acyl hydrazine group, an epoxy group, an aldehyde group, and a hydroxy group. Preferably, the thiol-reactive group is selected from the group consisting of a 2-pyridyldithio group, a 3-carboxy-4-nitrophenyldithio group, a maleimide group, an iodoacetamide group, and a vinylsulfonyl group.

The hydrophilic group of the water-soluble photo-activatable polymer of the invention is present in an amount sufficient to make the water-soluble photo-activatable polymer soluble in water. In certain embodiments of the invention, the hydrophilic group is an amino group or a carboxy group.

The reactive group and the hydrophilic group of the water-soluble photo-activatable polymer of the invention can be identical or different. In one embodiment of the invention, both the reactive group and the hydrophilic group are amino groups. In another embodiment of the invention, the reactive group is the 2-pyridyldithio group, and the hydrophilic group is the carboxy group.

In certain embodiments of the invention, the photo-activatable group is at least one of an aryl ketone and an aryl azide. Preferably, the aryl ketone is benzophenone or acetophenone.

In one embodiment of the invention, the water-soluble polymer is poly(allylamine) based benzophenone (PAA-BzPh) and is represented by a formula:

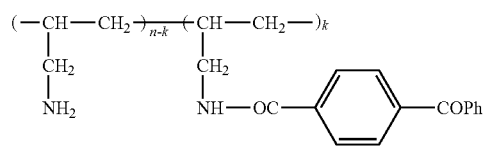

wherein n is 50 to 2000 and k is 10 to 1000.

In another embodiment of the invention, the water-soluble polymer is poly(allylamine) based benzophenone further modified to contain 2-pyridyldithio groups (PDT-BzPh) and is represented by a formula:

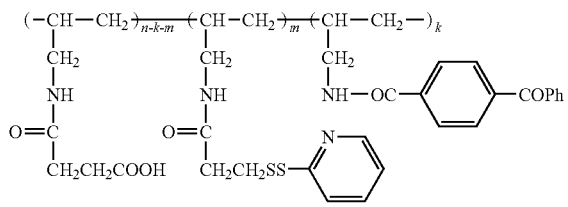

wherein n is 50 to 2000, k is 10 to 1000, and m is 10 to 1000.

In yet another embodiment, the water-soluble photo-activatable polymer of the invention is poly(allylamine)-benzophenone-pyridyldithio-carboxylate (PBPC) or poly(allylamine)-benzophenone-maleimido-carboxylate (PBMC) (see FIG. 14 and Example 9).

Methods of preparation of the water-soluble photo-activatable polymer of the invention based on poly(allylamine) and poly(acrylic acid) are described in Examples 1 and 2.

The water-soluble photo-activatable polymer of the invention can be prepared by radical polymerization of a mixture of three types of monomers (e.g., acrylamide-based monomers), each containing only one of the groups, as shown below:

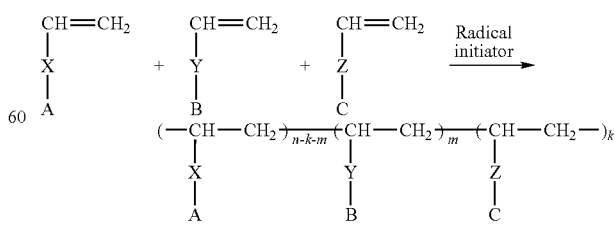

X, Y and Z are suitable spacers
A = photo-activatable group, B = hydrophilic group, C = reactive group In this invention, identity of spacers is not crucial. X, Y and Z can be residues of aliphatic, cyclo-aliphatic or aromatic hydrocarbons, which may include heteroatoms (O, N, S, etc.) and contain functional groups not interfering with both the polymerization and the further performance of the resulting multifunctional polymeric cross-linker (like OH, amide, etc.).

The ratio between these groups in the final product can be controlled by changing the ratio of monomers. Conditions for polymerization are known to persons skilled in the art. Additionally, each monomer can bear two, or all the three types of the groups. Other types of polymerization or polycondensation known in the art can also be used.

Figure 1:
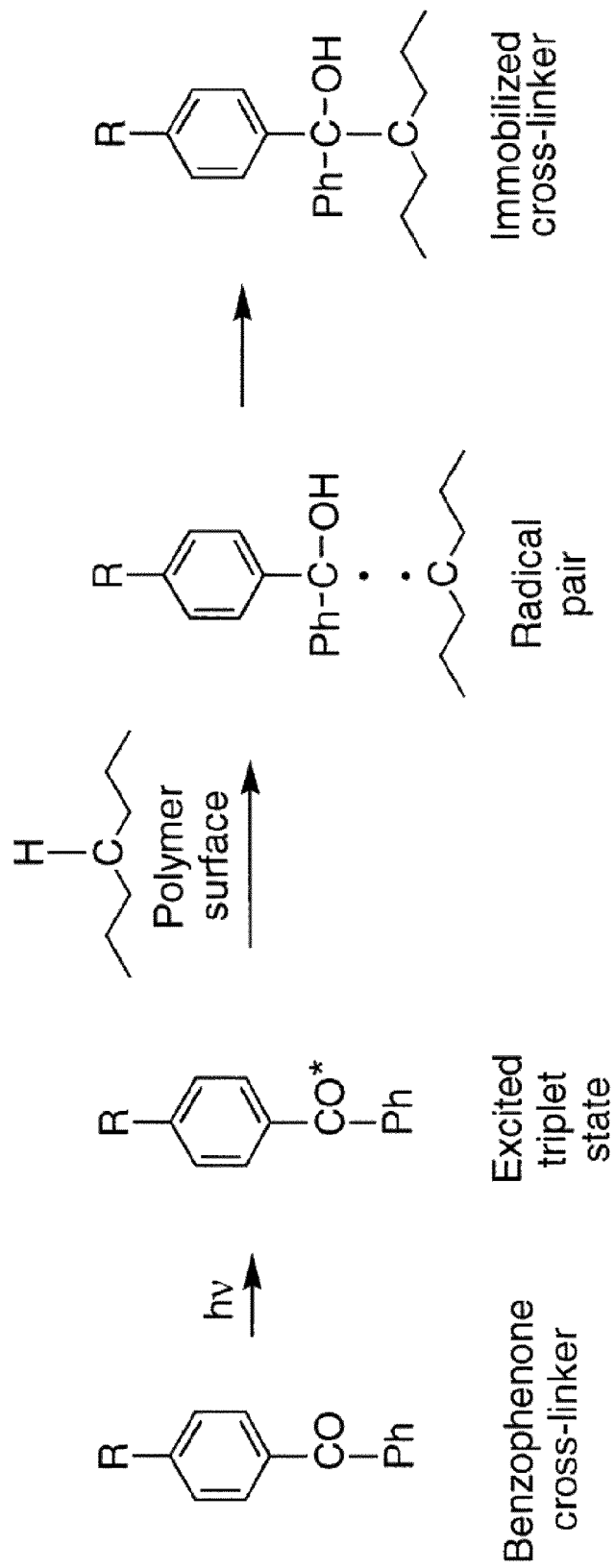
FIG. 1 is a reaction scheme illustrating binding of benzophenone cross-linkers to polymers having C—H bonds.

Upon excitation of photo-activatable groups, the water-soluble photo-activatable polymer of the invention is covalently bonded to carbon atoms of the surface and forms a monomolecular layer on the surface (see FIG. 1).

The term "layer" used herein means a contiguous and non-contiguous deposit formed by a covalent bonding of water-soluble photo-activatable polymers of the invention to the surface. Preferably, the layer is highly homogeneous and consists essentially of the water-soluble photo-activatable polymer of the invention.

Further provided is a composition of matter comprising a monomolecular layer of the water-soluble photo-activatable polymer of the invention and a matrix having at least one carbon, wherein the monomolecular layer is covalently attached to the matrix by a covalent bond formed between the photo-activatable group and the at least one carbon of the matrix.

Figure 3:
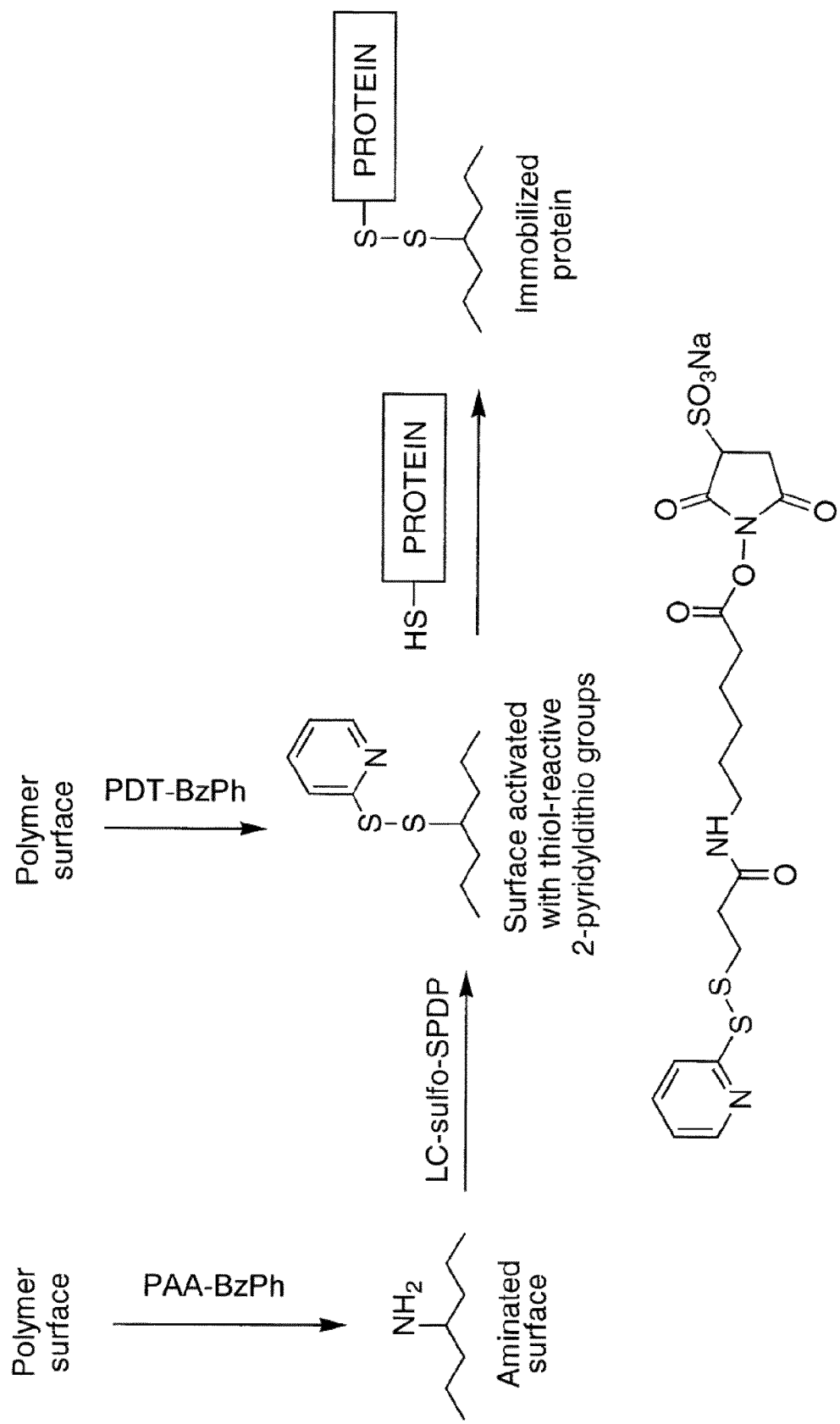
FIG. 3 is a reaction scheme depicting immobilization of thiol-containing proteins on a polymeric surface.

In certain embodiments, the composition further comprises a biomaterial having a plurality of active groups, wherein the biomaterial is covalently attached to the monomolecular layer by covalent bonding between active groups and reactive groups (see FIGS. 3, 5, and 10A).

In certain embodiments of the composition, at least one of the active groups is a member selected from the group consisting of amine, carboxyl, hydroxyl, thiol, phenol, imidazole, and indole. Preferably, at least one of the active groups is a thiol group.

Biomaterial

The biomaterial of the present invention can be any molecule or macromolecule to which a suitable reactive group, such as a carboxy (—COOH), amino (—NH$_2$) or thiol group (—SH) is attached. For example, proteins or peptides that have been modified to comprise a thiol group or comprise an amino group can be used. The biomaterial also has a therapeutic utility.

Suitable biomaterial include pharmaceuticals, nucleic acids, such as transposons, signaling proteins that facilitate wound healing, such as TGF-β, FGF, PDGF, IGF and GH proteins that regulate cell survival and apoptosis, such as Bcl-1 family members and caspases; tumor suppressor proteins, such as the retinoblastoma, p53, PAC, DCC. NF1, NF2, RET, VHL and WT-1 gene products; extracellular matrix proteins, such as laminins, fibronectins and integrins; cell adhesion molecules such as cadherins, N-CAMs, selectins and immunoglobulins; anti-inflammatory proteins such as Thymosin beta-4, IL-10 and IL-12.

In certain embodiments, the biomaterial includes at least one of heparin, covalent heparin, or another thrombin inhibitor, hirudin, hirulog, argatroban, D-phenylalanyl-L-poly-L-arginyl chloromethyl ketone, or another antithrombogenic agent, or mixtures thereof; urokinase, streptokinase, a tissue plasminogen activator, or another thrombolytic agent, or mixtures thereof, a fibrinolytic agent; a vasospasm inhibitor; a calcium channel blocker, a nitrate, nitric oxide, a nitric oxide promoter or another vasodilator; an antimicrobial agent or antibiotic; aspirin, ticlopidine, a glycoprotein IIb/IIIa inhibitor or another inhibitor of surface glycoprotein receptors, or another antiplatelet agent; colchicine or another antimitotic, or another microtubule inhibitor, dimethyl sulfoxide (DMSO), a retinoid or another antisecretory agent; cytochalasin or another actin inhibitor; a remodeling inhibitor; deoxyribonucleic acid, an antisense nucleotide or another agent for molecular genetic intervention; methotrexate or another antimetabolite or antiproliferative agent; tamoxifen citrate, Taxol™ or derivatives thereof, or other anti-cancer chemotherapeutic agents; dexamethasone, dexamethasone sodium phosphate, dexamethasone acetate or another dexamethasone derivative, or another anti-inflammatory steroid or non-steroidal anti-inflammatory agent; cyclosporin or another immunosuppressive agent; trapidal (a PDGF antagonist), angiogenin, angiopeptin (a growth hormone antagonist), a growth factor or an anti-growth factor antibody, or another growth factor antagonist; dopamine, bromocriptine mesylate, pergolide mesylate or another dopamine agonist; radiotherapeutic agent; iodine-containing compounds, barium-containing compounds, gold, tantalum, platinum, tungsten or another heavy metal functioning as a radiopaque agent; a peptide, a protein, an enzyme, an extracellular matrix component, a cellular component or another biologic agent; captopril, enalapril or another angiotensin converting enzyme (ACE) inhibitor; ascorbic acid, alpha tocopherol, superoxide dismutase, deferoxamine, a 21-amino steroid (lasaroid) or another free radical scavenger, iron chelator or antioxidant; a $^{14}$C—, $^{3}$H—, $^{32}$P— or $^{36}$S-radiolabelled form or other radiolabelled form of any of the foregoing; a hormone; estrogen or another sex hormone; AZT or other antipolymerases; acyclovir, famciclovir, rimantadine hydrochloride, ganciclovir sodium or other antiviral agents; 5-aminolevulinic acid, meta-tetrahydroxyphenylchlorin, hexadecafluoro zinc phthalocyanine, tetramethyl hematoporphyrin, rhodamine 123 or other photodynamic therapy agents; an IgG2 Kappa antibody against *Pseudomonas aeruginosa* exotoxin A and reactive with A431 epidermoid carcinoma cells, monoclonal antibody against the noradrenergic enzyme dopamine beta-hydroxylase conjugated to saporin or other antibody targeted therapy agents; gene therapy agents; and enalapril and other prodrugs, or a mixture of any of these.

Additionally, the biomaterial can be either component of any affinity-ligand pair. Examples of such affinity ligand pairs include avidin-biotin and IgG-protein A. Furthermore, the biomaterial can be either component of any receptor-ligand pair. One example is transferrin and its receptor. Other affinity ligand pairs include powerful hydrogen bonding or ionic bonding entities such as chemical complexes. Examples of the latter include metallo-amine complexes. Other such attractive complexes include nucleic acid base pairs, via immobilizing oligonucleotides of a specific sequence, especially antisense. Nucleic acid decoys or synthetic analogues can also be used as pairing agents to bind a designed gene vector with attractive sites. Furthermore, DNA binding proteins can also be considered as specific affinity agents; these include such entities as histones, transcription factors, and receptors such as the gluco-corticoid receptor.

In one preferred embodiment, the biomaterial is an anti-nucleic acid antibody. The antibody can therefore specifically bind a nucleic acid, which encodes a product (or the precursor of a product) that decreases cell proliferation or induces cell death, thereby mitigating the problem of restenosis in arteries and other vessels. The nucleic acid that is tethered to a matrix via the antibody can efficiently transfect/transducer cells. In general terms, the field of "gene therapy" involves delivering into target cells some polynucleotide, such as an antisense DNA or RNA, a ribozyme, a viral fragment, or a functionally active gene, that has a therapeutic or prophylactic effect on the cell or the organism containing it (see Culver, 1994, GENE THERAPY: A HANDBOOK FOR PHYSICIANS (Mary Ann Liebert, Inc., New York, N.Y.)). The antibody of the composition can be a full-length (i.e., naturally occurring or formed by normal immuno-globulin gene fragment recombinatorial processes) immunoglobulin molecule (e.g., an IgG antibody, or IgM or any antibody subtype) or an immunologically active (i.e., specifically binding) portion of an immunoglobulin molecule. The antibody comprises one or more sites which specifically bind with a nucleic acid (i.e., which does not substantially bind other types of molecules). The binding site can be one which binds specifically with a nucleic acid of a desired type without regard to the nucleotide sequence of the nucleic acid. The binding site can, alternatively, be one which binds specifically only with a nucleic acid comprising a desired nucleotide sequence. Preferably, the antibody is a thiol modified antibody.

The complex formed between a polynucleotide and a cognate antibody can be immobilized on a variety of surfaces such that, when the surface is exposed to a physiological environment in situ, the attached polynucleotide is released, over time, in a manner that enhances delivery of the polynucleotide to cells in the proximity. Surprisingly, DNA transfer by way of immunospecific tethering maintains the nucleic acid in regions that are subject to gene therapy.

Examples of suitable antibodies include Fv, F(ab), and F(ab')$_2$ fragments, which can be generated is conventional fashion, as by treating an antibody with pepsin or another proteolytic enzyme. The nucleic acid-binding antibody used in a composition of the present invention can be polyclonal antibody or a monoclonal antibody. A "monoclonal" antibody comprises only one type of antigen binding site that specifically binds with the nucleic acid. A "polyclonal" antibody can comprise multiple antigen binding sites that specifically bind the nucleic acid. An antibody employed in this invention preferably is a full-length antibody or a fragment of an antibody, such as F(ab')$_2$, that possesses the desired binding properties.

A nucleic acid for use in the present invention can be any polynucleotide that one desires to transport to the interior of a cell. In this context, a "therapeutic polynucleotide" is a polymer of nucleotides that, when provided to or expressed in a cell, alleviates, inhibits, or prevents a disease or adverse condition, such as inflammation and/or promotes tissue healing and repair (e.g., wound healing). The nucleic acid can be composed of deoxyribonucleosides or ribonucleosides, and can have phosphodiester linkages or modified linkages, such as those described below. The phrase "nucleic acid" also encompasses polynucleotides composed of bases other than the five that are typical of biological systems: adenine, guanine, thymine, cytosine and uracil.

A suitable nucleic acid can be DNA or RNA, linear or circular and can be single-or-double-stranded. The "DNA" category in this regard includes cDNA; genomic DNA; triple helical, supercoiled, Z-DNA and other unusual forms of DNA; polynucleotide analogs; an expression construct that comprises a DNA segment coding for a protein, including a therapeutic protein; so-called "antisense" constructs that, upon transcription, yield a ribozyme or an antisense RNA; viral genome fragments, such as viral DNA; plasmids and cosmids; and a gene or gene fragment.

The nucleic acid also can be RNA, for example, antisense RNA, catalytic RNA, catalytic RNA/protein complex (i.e., a "ribozyme"), and expression construct comprised of RNA that can be translated directly, generating a protein, or that can be reverse transcribed and either transcribed or transcribed and then translated, generating an RNA or protein product, respectively; transcribable constructs comprising RNA that embodies the promoter/regulatory sequence(s) necessary for the generation of DNA by reverse transcription; viral RNA; and RNA that codes for a therapeutic protein, inter alia. A suitable nucleic acid can be selected on the basis of a known, anticipated, or expected biological activity that the nucleic acid will exhibit upon delivery to the interior of a target cell or its nucleus.

The length of the nucleic acid is not critical to the invention. Any number of base pairs up to the full-length gene may be transfected. For example, the nucleic acid can be linear or circular double-stranded DNA molecule having a length from about 100 to 10,000 base pairs in length, although both longer and shorter nucleic acids can be used.

The nucleic acid can be a therapeutic agent, such as an antisense DNA molecule that inhibits mRNA translation. Alternatively, the nucleic acid can encode a therapeutic agent, such as a transcription or translation product which, when expressed by a target cell to which the nucleic acid-containing composition is delivered, has a therapeutic effect on the cell or on a host organism that includes the cell. Examples of therapeutic transcription products include proteins (e.g., antibodies, enzymes, receptors-binding ligands, wound-healing proteins, anti-restenotic proteins, anti-oncogenic proteins, and transcriptional or translational regulatory proteins), antisense RNA molecules, ribozymes, viral genome fragments, and the like. The nucleic acid likewise can encode a product that functions as a marker for cells that have been transformed, using the composition. Illustrative markers include proteins that have identifiable spectroscopic properties, such as green fluorescent protein (GFP) and proteins that are expressed on cell surfaces (i.e., can be detected by contacting the target cell with an agent which specifically binds the protein). Also, the nucleic acid can be a prophylactic agent useful in the prevention of disease.

A nucleic-acid category that is important to the present invention encompasses polynucleotides that encode proteins that affect wound-healing. For example, the genes egf, tgf, kgf, hb-egf, pdgf igf, fgf-1, fgf-2, vegf, other growth factors and their receptors, play a considerable role in wound repair.

Another category of polynucleotides, coding for factors that modulate or counteract inflammatory processes, also is significant for the present invention. Also relevant are genes that encode an anti-inflammatory agent such as MSH, a cytokine such as IL-10, or a receptor antagonist that diminishes the inflammatory response.

Suitable polynucleotides can code for an expression product that induces cell death or, alternatively, promotes cell survival, depending on the nucleic acid. These polynucleotides are useful not only for treating tumorigenic and other abnormal cells but also for inducing apoptosis in normal cells. Accordingly, another notable nucleic-acid category for the present invention relates to polynucleotides that, upon expression, encode an anti-oncogenic protein or, upon transcription, yield an anti-oncogenic antisense oligonucleotide. In this context, the phrases "anti-oncogenic protein" and "anti-oncogenic antisense oligonucleotide" respectively denote a protein or an antisense oligonucleotide that, when provided to any region where cell death is desired, or the site of a cancerous or precancerous lesion in a subject, prevents, inhibits, reverses abnormal and normal cellular growth at the site or induces apoptosis of cells. Delivery of such a polynucleotide to cells, pursuant to the present invention, can inhibit cellular growth, differentiation, or migration to prevent movement or unwanted expansion of tissue at or near the site of transfer. Illustrative of this anti-oncogenic category are polynucleotides that code for one of the known anti-oncogenic proteins. Such a polynucleotide would include, for example, a nucleotide sequence taken or derived from one or more of the following genes: abl, akt2, apc, bcl2-alpha, bcl2-beta, bcl3, bcl3, bcl-x, bad, bcr, brca1 , brca2, cbl, ccnd1 , cdk4, crk-II, csflr/fms, dbl, dcc, dpc4/smad4, e-cad, e2fl/rbap, egfr/erbb-1, elk1, elk3, eph, erg, ets1, ets2, fer, fgr/src2, fos, fps/fes, fral , fra2, fyn, hck, hek, her2/erbb-2/neu, her3/erbb-3, her4/erbb-4, hras1, hst2, hstf1 , ink4a, ink4b, int2/fgf3, jun, junb, jund, kip2, kit, kras2a, kras2b, ck, lyn, mas, max, mcc, met, mlh1, mos, msh2, msh3, msh6, myb, myba, mybb, myc, mycl1, mycn, nf1 , nf2, nras, p53, pdgfb, pim1, pms1, pms2, ptc, pten, raft, rb1, rel, ret, ros1, ski, src1, tal1, tgfbr2, thra1, thrb, tiam1, trk, vav, vhl, waf1, wnt1, wnt2, wt1 and yes1. By the same token, oligonucleotides that inhibit expression of one of these genes can be used as anti-oncogenic antisense oligonucleotides.

Nucleic acids having modified internucleoside linkages also can be used in composition according to the present invention. For example, nucleic acids can be employed that contain modified internucleoside linkages which exhibit increased nuclease stability. Such polynucleotides include, for example, those that contain one or more phosphonate, phosphorothioate, phosphorodithioate, phosphoramidate methoxyethyl phosphoramidate, formacetal, thioformacetal, diisopropylsilyl, acetamidate, carbamate, dimethylene-sulfide ($—CH_2—S—CH_2—$), dimethylene-sulfoxide ($—CH_2—SO—CH_2—$), dimethylenesulfone ($—CH_2—SO_2—CH_2—$), 2'-O-alkyl, and 2'-deoxy-2'-fluoro-phosphorothioate internucleoside linkages.

For present purposes, a nucleic acid can be prepared or isolated by any conventional means typically used to prepare or isolate nucleic acids. For example, DNA and RNA can be chemically synthesized using commercially available reagents and synthesizers by known methods. For example, see Gait, 1985, in: OLIGONUCLEOTIDE SYNTHESIS: A PRACTICAL APPROACH (IRL Press, Oxford, England). RNA molecules also can be produced in high yield via in vitro transcription techniques, using plasmids such as SP65, available from Promega Corporation (Madison, Wis.). The nucleic acid can be purified by any suitable means, and many such means are known. For example, the nucleic acid can be purified by reverse-phase or ion exchange HPLC, size exclusion chromatography, or gel electrophoresis. Of course, the skilled artisan will recognize that the method of purification will depend in part on the size of the DNA to be purified. The nucleic acid also can be prepared via any of the innumerable recombinant techniques that are known or that are developed hereafter.

A suitable nucleic acid can be engineered into a variety of known host vector systems that provide for replication of the nucleic acid on a scale suitable for the preparation of an inventive composition. Vector systems can be viral or non-viral. Particular examples of viral vector systems include adenovirus, retrovirus, adeno-associated virus and herpes simplex virus. Preferably, an adenovirus vector is used. A non-viral vector system includes a plasmid, a circular, double-stranded DNA molecule. Viral and nonviral vector systems can be designed, using known methods, to contain the elements necessary for directing transcription, translation, or both, of the nucleic acid in a cell to which is delivered. Methods which are known to the skilled artisan can be used to construct expression constructs having the protein coding sequence operably linked with appropriate transcriptional/translational control signals. These methods include in vitro recombinant DNA techniques and synthetic techniques. For instance, see Sambrook et al., 1989, MOLECULAR CLONING: A LABORATORY MANUAL (Cold Spring Harbor Laboratory, New York), and Ausubel et al., 1997, CURRENT PROTOCOLS IN MOLECULAR BIOLOGY (John Wiley & Sons, New York).

A nucleic acid encoding one or more proteins of interest can be operatively associated with a variety of different promoter/regulator sequences. The promoter/regulator sequences can include a constitutive or inducible promoter, and can be used under the appropriate conditions to direct high level or regulated expression of the gene of interest. Particular examples of promoter/regulatory regions that can be used include the cytomegalovirus (CMV) promoter/regulatory region and the promoter/regulatory regions associated with the SV40 early genes or the SV40 late genes. Preferably, the human CMV promoter is used, but substantially any promoter/regulatory region directing high level or regulated expression of the gene of interest can be used.

It also is within the scope of the present invention that the employed nucleic acid contains a plurality of protein-coding regions, combined on a single genetic construct under control of one or more promoters. The two or more protein-coding regions can be under the transcriptional control of a single promoter, and the transcript of the nucleic acid can comprise one or more internal ribosome entry sites interposed between the protein-coding regions. Thus, a myriad of different genes and genetic constructs can be utilized.

In certain embodiments of the composition, the biomaterial is a member selected from the group consisting of an antibody, a viral vector, a growth factor, a bioactive polypeptide, a polynucleotide coding for the bio active polypeptide, a cell regulatory small molecule, a peptide, a protein, an oligonucleotide, a gene therapy agent, a gene transfection vector, a receptor, a cell, a drug, a drug delivering agent, nitric oxide, an antimicrobial agent, an antibiotic, an antimitotic, dimethyl sulfoxide, an antisecretory agent, an anti-cancer chemotherapeutic agent, steroidal and non-steroidal anti-inflammatories, hormones, an extracellular matrix, a free radical scavenger, an iron chelator, an antioxidant, an imaging agent, and a radiotherapeutic agent. Preferably, the biomaterial is at least one of an anti-knob antibody, an adenovirus, a D1 domain of the Coxsackie-adenovirus receptor (CAR D1), insulin, an angiogenic peptide, an antiangiogenic peptide, avidin, biotin, IgG, protein A, transferrin, and a receptor for transferrin. A combination of multiple types of biomaterials bound to each other by affinity is also contemplated. For example, an adenovirus bound to a D1 domain of the Coxsackie-adenovirus receptor (CAR D1) or to a specific antibody can be attached to the matrix via the water-soluble photo-activatable polymer.

Antibodies specific for non-viral vectors or nucleic acid may require use of a transfection agent to enhance administration of nucleic acid. The transfection agent is a cationic macromolecule that is positively charged, comprises two or more art-recognized modular units (e.g., amino acid residues, fatty acid moieties, or polymer repeating units), and is preferably capable of forming supermolecular structures (e.g., aggregates, liposomes or micelles) at high concentration in aqueous solution or suspension. Among the types of cationic macromolecules that can be used are cationic lipid and polycationic polypeptides.

The amount of the transfection agent to be used when transfecting cells can be calculated based on nucleic acid content of the composition. The capacity of the medium comprising or containing the transfection agent can also affect the amount of transfection agent to be used. When the antibody of the transfection agent is immobilized on a matrix, the amount of cationic macromolecule and DNA that can be complexed with the antibody can be limited by the physical requirements of the metal support. For example, rigidity, flexibility and chemical reactivity may influence the amount of transfection agent used. Such vectors have included retroviral, adenovirus, adeno-associated viral vectors and herpes viral vectors. Cells can be infected with viral vectors by known methods.

Further provided is a method of making the composition of the invention, the method comprising providing the matrix having at least one carbon; providing an aqueous solution of the water-soluble photo-activatable polymer having the photo-activatable group and the reactive group; and photo-activating the photo-activatable group by irradiation to covalently attach the water-soluble polymer via the photo-activatable group to the matrix and thereby forming the monomolecular layer of the composition on the matrix. Example 3 describes the conditions of the method using PAA-BzPh and PDT-BzPh as non-limiting examples.

In certain embodiments of the method of making the composition of the invention, the irradiation is performed at a wavelength from about 190 to about 900 nm. Preferably, the irradiation is performed at a wavelength of 280 to 360 nm.

Additionally, certain embodiments of the method further comprise providing a biomaterial having a plurality of active groups and reacting the plurality of active groups with the water-soluble photo-activatable polymer to covalently attach the biomaterial to the matrix. Conditions of such reaction should not be damaging for the biomaterial to be attached. These conditions should involve using buffers in the physiologic range (pH 7.35-7.45) and osmotic strength, and temperature conditions between 25C and 37C, but not higher or lower.

Photochemical Modification of Micro- and Nanoparticles

The water-soluble photo-activatable polymers of the invention obtained as described above can be bound to the surface of pre-formed micro- or nanoparticles (MP and NP, respectively) to form modified particles capable of reacting with the biomaterial.

Advantageously, in the preparation of biodegradable and non-biodegradable polymeric micro- and nanoparticles, the water-soluble photo-activatable polymer of the invention (e.g., BzPh-PDT) not only makes the surface reactive towards biomolecules containing suitable reactive groups (e.g., the thiol-containing biomolecules), but also prevents the flocculation of particles and thus stabilizes the suspension.

Particles modified with water-soluble photo-activatable polymers of the invention can be delivered via various delivery routes to an organism. For example, injectable nanoparticles can be used to either provide an intravenous means of sustained delivery of proteins and peptides, or if injected into a specific site such as a tumor, or the myocardium, can provide sustained local presence of therapeutic peptides and proteins.

Particles size and composition can be tailored to a specific application. Particles can be prepared by one of the existing methods (see Couvreur P et al., Nanoparticles: preparation and characterization. In: Benita S, Editor, Microencapsulation. Methods and industrial applications. vol. 73. New York: Marcel Dekker, 1996. pp. 183-211; Kumar MNR. Nano- and microparticles as controlled drug delivery devices. J Pharm Pharmaceut Sci 2000; 3:234-58).

Most widely used are methods including emulsification-polymerization and polymer precipitation techniques. The former may be accomplished by in situ polymerization of monomers either in aqueous solution or emulsified in aqueous phase (namely, emulsification-polymerization). Alternatively, methods exploiting pre-formed biocompatible polymers, usually of polyester and polyanhydride families, can be used to form particles by polymer precipitation methods. The most popular methods are emulsification-solvent evaporation, emulsification-diffusion and nanoprecipitation methods (see Quintanar-Guerrero et al., Preparation techniques and mechanisms of formation of biodegradable nanoparticles from preformed polymers. Drug Dev Ind Pharm 1998; 24:1113-28). The latter methods are based on emulsifying an organic solution of a polymer with or without drug in an aqueous phase in presence of a stabilizer substance (e.g., Poloxamer 188, polyvinyl alcohol, etc.) achieved either by external energy input or through spontaneous diffusion of water-miscible solvents with subsequent solvent elimination to form solid particle dispersion.

While both emulsification-polymerization and polymer precipitation are applicable for preparing matrix-type particles (spheres), some of these methods with appropriate modifications can be used for producing core-shell type vesicles (capsules). The drug substance can either be encapsulated (dissolved or dispersed in the polymeric matrix of a sphere or dissolved in the liquid core of a capsule) or adsorbed/chemically bound to the particle surface. The latter approach where a substance is attached to the surface of a preformed particle has the advantage of avoiding harsh conditions (extreme pH, exposure to organic solvents or elevated temperatures) employed for the particle formulation. Covalent association of the drug with the particle surface employing biodegradable chemical bonds (e.g., by disulfide linking) provides an alternative that achieves both controlled and site-specific release of the drug. Further, affinity based association of one type of biomaterial with another type of biomaterial, which it turn is covalently found to the water-soluble photo-activatable polymer of the invention coupled to nanoparticles provides a novel delivery option for biomaterial based on the release of affinity bonds (see FIG. 5).

Attachment of biomaterial to NP has been demonstrated using D1, IgG and adenovirus. It should be understood that these embodiments are non-limiting examples.

Adenovirus (AdV or Ad were used in this disclosure interchangeably) is a promising gene vector for therapeutic applications. However, its use is compromised, since AdV-mediated gene transfer is suboptimal in cell types deficient in Coxsackie-AdV receptor (CAR). Inventors have discovered that adenovirus vector (AdV) delivery and transgene expression at levels equivalent to or greater than with CAR-processing could be achieved through a receptor-independent mechanism by affinity tethering AdV to the surface of biodegradable nanoparticles (NP).

In certain embodiments of the composition, the viral vector is adenoviral vector (AdV) encoding a desired protein such as, for example, GFP or inducible NO synthase (iNOS).

NP (350-450 nm) were prepared by a modified emulsification-solvent evaporation method and surface-modified by an anionic thiol- and photoreactive poly(allylamine) derivative by a brief exposure to UV light. The NP were coated with a thiolated D1 domain of CAR or non-immune IgG as a control, and associated with GFP- or inducible NO synthase (iNOS)-encoding AdV. The uptake of BODIPY 564/570-labeled NP and GFP expression were assayed fluorimetrically. Cell growth inhibition was determined in A10 cells two days post transduction using the AlamarBlue assay. The gene expression in A10 cells treated with AdV-NP composites was found to be dependent on the D1-modified NP amount and equaled several times that of free AdV treated cells, while no increase in efficacy was shown for the AdV applied with IgG-modified NP despite an equally effective uptake of the two NP types. Exposure to knob protein resulted in a complete inhibition of gene expression mediated by free AdV, whereas no change in the transduction efficacy was observed for AdV-NP. Composites formulated with iNOS AdV effectively inhibited A10 cell growth (e.g., 58% inhibition), whereas iNOS AdV alone or in presence of IgG-coated NP had a substantially lower effect on the cell proliferation (e.g., 0% and 22% inhibition, respectively). This inhibitory effect correlated well with the gene expression measured using GFP AdV reporter. These results demonstrate that AdV-NP composites taken up via a receptor-independent pathway can substantially increase gene transfer in vitro. This strategy is therefore advantageous for transduction of CAR-deficient cells. The potent smooth muscle cell growth inhibitory effect achieved with iNOS AdV-NP composites makes this delivery system a promising candidate for gene therapy of proliferative disorders (e.g., for restenosis, cancer treatment, vasodilation and pulmonary hypertension). Also provided is a method for delivery of a biomaterial to a cell or an organism, the process comprising (1) providing the composition of the invention as a monomolecular layer and a matrix having at least one carbon, wherein the monomolecular layer is covalently attached to the matrix by a covalent bond between the photo-activatable group and the at least one carbon, (2) providing a biomaterial having a plurality of active groups, wherein the biomaterial is covalently attached to the monomolecular layer by covalent bonding between the active groups and the reactive groups; and (3) administering the matrix to the cell or an organism.

In vivo studies examined the levels and regional differences in Ad luciferase reporter ($_{LUC}$Ad) gene expression comparing NP-Ad complexes and free Ad administered subdermally in rats using quantitative biophotonic imaging.

Amounts of the biomaterial may vary depending on the purpose of delivery, e.g., prophylactic, diagnostic, therapeutic, etc. and on the nature of the biomaterial involved.

In certain embodiments, the biomaterial delivered by this method is the biomaterial is at least one of a protein, a D1 domain of the Coxsackie-adenovirus receptor, an adenovirus, or an antibody specifically bound to a nucleic acid.

These investigations have demonstrated a number of major findings including: 1) the synthesis of a multifunctional thiol- and photoreactive polymer (PBPC/PBMC) for chemically activating the surface of nanoparticles, 2) the formulation of surface activated (via PBPC/PBMC) biodegradable NP that mediate viral vector delivery through NP-surface tethering with covalently attached vector binding proteins, and 3) demonstrating that these NP-Ad complexes achieve gene expression levels both in vitro and in vivo that exceed those with equivalent amounts of free Ad. Other groups have not reported the synthesis and functionality of photoreactive polymers comparable to PBPC, which can in fact react following ultraviolet light exposure with virtually any C—H bond, thus making this reagent a particularly potent tool for creating surface modifications for a wide variety of synthetic and biopolymers. PLA as a substrate is abundant with C—H bonds capable of reaction with the excited aromatic ketone functions of PBPC, which is another important advantage of the present approach as opposed to a recently described end-group modification of NP-forming PLA (Nobs et al., 2003, 2004) that is limited by the number of exposed carboxylic functions.

The vector tethering strategy reported herein has previously been investigated by our group for gene delivery from the surfaces of collagen coated stents using anti-knob antibodies (Klugherz et al., 2002). However, the present NP studies are the first demonstration of NP-Ad delivery with D1 as a tethering agent. The receptor-independent mechanism for Ad-NP cell entry is another important unique feature of this formulation, enabling the transduction of cells with relatively low to absent levels of CAR.

Several of the individual components of the present formulations have been investigated by others with results that support the findings of our studies. Surface tethering of viral vectors to nondegradable particles has been investigated and varying degrees of gene expression enhancement were observed in these studies following delivery of Ad in a form of conjugates to nondegradable nano- and microbeads in vitro and in vivo (Pandori et al., 2002a; Qiang et al., 2004; Pandori and Sano, 2005). However, an increased gene transfer by Ad immobilized on the surface of biodegradable NP using an Ad-specific binding protein has not been described. Furthermore, while the potentiating effect of association with solid particles has been demonstrated for different types of viral vectors, including lentivirus (Haim et al., 2005), retrovirus (Hughes et al., 2001) and adeno associated virus (Mah et al., 2002), the mechanism of the enhancement has not been studied in sufficient detail, and its correlation with the nature of the virus binding to the carrier particles and their cell entry has not been clearly delineated in these prior investigations.

The D1 protein used in this study for Ad immobilization is an extracellular immunoglobulin-like domain of CAR possessing a high binding affinity to the adenoviral fiber knob domain ($K_d$ in the order of 20-25 nM) (Lortat-Jacob et al., 2001). The approach employing D1 as an Ad-specific affinity ligand allows for immobilization of the viral vector on the preformed NP in one step without need for prior chemical modification of the virus that may potentially result in a substantial loss of vector infectivity (Pandori et al., 2002b). The modification of the NP with D1 was accompanied by some increase in the particle size that can be attributed to the layer of the surface-bound protein, whereas the colloidal stability of the formulation was not adversely affected. Furthermore, NP coated with D1 remained stable in suspension upon binding Ad in contrast to the $_{AK}$NP. The colloidal stability correlated with the gene transfer efficacies of the respective formulations favoring the submicronial-sized $_{D1}$NP-Ad complexes exhibiting high cell entry capacity, and is also of importance in terms of safety of their use in vivo.

NP-Ad were efficiently taken up by cells and exhibited sustained elimination kinetics with more than half of the initial particle load resident in the cells interior after 72 hr (FIG. 3). Despite the high intracellular levels achieved within 2 hr of exposure, the complexes elicited no cell toxic effects as evidenced by cell growth that was unaffected by $_{D1}$NP-$_{NULL}$Ad at any dose in the studied range (FIG. 4 F). The moderate cell toxicity caused by the GFP-encoding complexes (FIG. 4 E) should therefore be attributed to the GFP gene product that is known to be toxic when expressed at high levels (Liu et al., 1999). The NP-Ad internalization occurred through a CAR-independent mechanism, which is in compliance with relative increase in transduction that was most significant in the H5V cells that are completely devoid of CAR expression, and is also supported by data showing the recovery of viral gene expression inhibited by knob protein achieved by vector association with $_{D1}$NP. This is in agreement with the results recently reported by Pandori et al. (Pandori and Sano, 2005) who observed equal infectivity of Ad immobilized on non-biodegradable silica microbeads in the presence or absence of anti-CAR antibody used to block the CAR-mediated cell entry. Smooth muscle and endothelial cells are known to express relatively low levels of CAR (Wickham et al., 1996; Wickham et al., 1997) necessitating the use of high titres of Ad in order to achieve sufficiently high levels of transgene expression in vascular cells in vitro and in vivo (Baker, 2004). The potent CAR-independent cellular uptake of the NP-Ad complexes resulting in a strongly enhanced gene expression by these cell types observed in our study may therefore be of relevance for the development of effective Ad-based therapies for cardiovascular disease.

The enhancement of the gene transfer efficacy was specific to NP that were surface-modified with the binding protein enabling Ad immobilization, and was directly dependent on the doses of Ad and NP (FIGS. 11A-B), which is in accord with the uptake depending near-linearly on the NP amount used to form the complexes (FIGS. 9A-B). However, a comparable degree of internalization was observed for control $_{nIgG}$NP and these NP exhibited no infectivity enhancement (FIGS. 7A-F) apparently due to their inability to promote viral cell entry requiring a sufficiently strong NP-Ad association. The high intracellular levels of the complexes observed in cell culture with resultant increase in gene expression appear to be due to a combined effect of the vector-binding particles concentration on the cell surface (Luo and Saltzman, 2000; Pandori and Sano, 2005), and the rapid kinetics of the CAR-uncoupled internalization. The potentiating effect of the Ad immobilization was most pronounced at low doses of Ad reaching transgene levels in A10 cells up to 45-fold higher compared to the equivalent dose of free Ad. The earlier onset of expression mediated by the complexes resulted in a notably higher gain in the transgenic product levels in A10 and BOEC 24 hr post treatment than at later timepoints. However, the difference in the GFP expression level between the complexes and control-treated cells remained significant over 7 days.

The mechanism of the virus dissociation from the carrier particle may potentially have an effect on the efficacy and kinetics of gene expression in vitro and in vivo. The substitution of the reducible disulfide bond between the NP and the Ad binding protein for a non-degradable thio ether linkage ($_{PDT-D1}$NP vs. $_{MI-D1}$NP) resulted in similar patterns of the reporter expression for the two formulations (FIGS. 10 B and 10 C), which given comparable rates of their cellular uptake suggests the same fate of the internalized viral vector in both cases. Therefore, it seems plausible that the dissociation of the D1-Ad bond accounts for the release of the virus from the complex. Whereas a strong binding between NP and Ad is obviously important, the incorporation of a degradable bond apparently is not a prerequisite for effective transduction achievable by this method.

Growth inhibition of A10 cells using an inducible NO synthase (iNOS) encoding vector was chosen to examine the ability of the $_{D1}$NP-Ad complexes to exert a therapeutically relevant effect. $_{iNOS}$Ad delivery with NP has not been demonstrated prior to the present studies. However, $_{iNOS}$Ad administered as suspensions of free vector has been shown to have pleiotropic effects on a number of mechanistic targets in the arterial wall including inhibition of arterial smooth muscle proliferation, inhibition of platelet activation, and enhanced arterial wall relaxation. Thus, NP-$_{iNOS}$Ad are of potential importance for novel therapies for vascular disease in view of the broad therapeutic impact of iNOS. A profound inhibition of aortic smooth muscle cell growth in culture was observed following treatment by the $_{D1}$NP-$_{iNOS}$Ad complexes, whereas no inhibitory effect was exhibited by complexes formulated with null Ad or $_{iNOS}$Ad applied in the presence of control $_{nIgG}$NP (FIGS. 4A-F). GFP reporter expression and cell growth inhibition by the two respective types of NP-Ad revealed a similar pattern suggesting that the expression of iNOS is the main determinant of the aortic smooth muscle cell growth inhibition in vitro, and confirming the utility of complexes formulated with a reporter-encoding Ad as a useful model.

The results of the examples described below need to be viewed in the context of several limitations of this work. For example, the long term biodegradation of the PLA core of the NP was not investigated; the half time of PLA degradation ranges from several weeks to several months (Laurencin and Elgendy, 1994; Perrin and English, 1997). Thus, while this parameter would not affect the rapid processing of the NP-Ad complexes observed in the present results, the fate of NP over time would be of concern and will be addressed in longer term studies. The dissociation constants for Ad bound to NP were not determined in these studies. Prior investigations indicate the $K_d$ in solution for the antibody used is 0.31 nM (Nyanguile et al., 2003), and the $K_d$ for D1 is 20-25 nM (Lortat-Jacob et al., 2001). However, when these Ad-binding proteins are immobilized onto surfaces the $K_d$ may differ, and this has been observed for D1 (Lortat-Jacob et al., 2001). This parameter is also of potential importance in terms of the long term fate of free Ad, and is of special importance since the results of the present study show that Ad-binding agent affinity and not covalent attachment of the binding agent to the NP surface determines Ad release. Furthermore, intracellular trafficking of NP and Ad before and after dissociation involves complex events, and should also be the subject for future investigations. The in vivo experiment reported herein demonstrated significantly greater early levels of gene expression with NP-Ad versus free Ad; however 5 day expression levels were comparable. These results can best be explained by the fate of NP-Ad following subcutaneous injection when there are principally interactions of NP-Ad with mobilized white blood cells that are transient and likely traffic out of the injection region by the five day time point. Nevertheless, an in vivo efficacy experiment involving a therapeutic endpoint would constitute a more definitive comparison of NP-Ad and free Ad.

NP-Ad complexes formed with PBPC-activated PLA NP, that were surface-modified with vector binding proteins can deliver Ad to cells in a CAR independent manner, resulting in higher levels of transgene expression both in vitro and in vivo than achieved with administration of comparable amounts of free Ad. These discoveries have important implications for the safe and efficacious use of adenoviral vectors in gene therapy.

Delivery of Biomaterial Via Magnetic Nanoparticle

An additional degree of site-specificity may be achieved by rendering the particles (with and without biomaterial) responsive to magnetic field (e.g., superparamagnetic) by inclusion a magnetic field-responsive agent (e.g., magnetite/maghemite nanocrystals) in the polymeric matrix (e.g., Ito R, Machida Y, Sannan T, Nagai TU-hwscsaBTW-B-Gddaaca. Magnetic granules: a novel system for specific drug delivery to esophageal mucosa in oral administration. Int J Pharm 1990; 61:109-117). This modification allows for concentrating the particles at their target tissue using magnetic field, thereby increasing their therapeutic efficacy and minimizing the formulation toxicity.

A magnetic field-responsive agent as used herein is a paramagnetic, superparamagnetic, or ferromagnetic substance capable of moving under influence of a magnetic force. Superparamagnetic material are preferred materials. In certain embodiments, the magnetic field-responsive agent is a member selected from the group consisting of iron, cobalt or nickel, alloys thereof, oxides thereof and mixed oxides/hydroxides of Fe(II) and/or Fe(III) with at least one of Co(II), Mn(II), Cu(II), Ni(II), Cr(III), Gd(III), Dy(III), and Sm(III).

Preferably, the magnetic field-responsive agent is at least one of Fe3O4, gamma-Fe2O3, or a mixture thereof. Preferably, the magnetic field-responsive agent is iron oxide in a shape of nanocrystals.

The magnetic field-responsive agent can be prepared by methods known in the art in various shapes and sizes (see Hyeon T., Chemical Synthesis of Magnetic Nanoparticles. The Royal Society of Chemistry 2003, Chem. Commun., 2003, 927-934). In certain embodiments, iron oxide nanocrystals were obtained by precipitation of mixed iron chlorides in the presence of a base in aqueous medium (see Khalafalla S E. Magnetic fluids, Chemtech 1975, September: 540-547).

FIG. 20 is a schematic representation of delivering magnetic nanoparticles carrying GFP encoding adenovirus to magnetic field gradients produced by 316L steel. The therapy (green glow) is delivered only to the cells growing on top of the 316L stent wires, in order to indicate the nature of local delivery method. The magnetic field across the mesh causes the development of high field gradients between the mesh wires which attracts and binds magnetically responsive nanoparticles. The conceptual model (see FIG. 20) for delivery of magnetic nanoparticles may be described mathematically with analytical expressions that involve several assumptions detailed as follows.

In obtaining the force required for delivery of magnetic nanoparticles, it is reasonable to neglect the field gradients throughout the wire-metallic meshwork from all but the directly adjacent wires, since the field gradient decays inversely with the cube of distance away from the wire center. Thus, if the biomolecular-nanoparticle complexes are located within a few wire diameters from the struts, it is reasonable to approximate the wire as an infinitely long cylinder. For such a case, the wire's magnetic potential $\phi_{wire}$ can be approximated by the following expression, assuming the wire is magnetized orthogonal to its long axis:

$$\varphi_{wire}(\vec{r}, \theta) = \frac{\lambda_{wire}}{2\pi} \frac{\cos(\theta)}{\vec{r}} \quad (1)$$

where $\vec{r}$ is the position vector of the field measurement point, $\theta$ is the angular elevation of the position vector with respect to the wire's magnetization, and $\lambda_{wire}$ is the experimentally determined magnetic property of an infinitely thin wire having units of A m, denoting an effective magnetic moment per unit length. The wire magnetization may in general be a constant or a nonlinear function of the external field. The magnetic field produced by the wire can be calculated by taking the negative gradient of the magnetic scalar potential as follows:

$$\vec{H}_{wire} = -\nabla\phi.$$

Superparamagnetic nanoparticles formulated primarily from ferrite are used in a limited number biomedical applications, because they lack remnant magnetization and therefore do not tend to form irreversible aggregates. Ferrites are ferromagnetic ceramic materials, compounds of iron (e.g., iron (III) oxide), boron and barium or strontium or molybdenum. Ferrites have a high magnetic permeability, which allows them to store stronger magnetic fields than iron, and are known as ceramic magnets.

Magnetization behavior of such nanoparticles typically follows a nonlinear relationship with the external field, described by the well-known Langevin's function. In order to achieve an analytical solution related to the nanoparticles of the invention, it is proposed to model the nanoparticle behavior using a hard saturation model, consisting of a linear regime in low fields followed by a constant saturation region in high fields. In the low field regime, the magnetic moment (m) of the nanoparticle is given in expression (2), which is the well-known result for the magnetic moment of a homogeneous isotropic sphere magnetized by a uniform magnetic field (see Yellen B B, Forbes Z G, Halverson D S, Fridman G, Barbee K A, Chorny M, Levy R J, Friedman G. Targeted drug delivery to magnetic implants for therapeutic applications. Journal of Magnetism and Magnetic Materials, 293:647-654, 2005)

$$\vec{m} = \frac{3\chi}{\chi+3} V \vec{H} \quad (2)$$

where V is the volume of the spherical particle, x is the magnetic susceptibility, and H is the external field at the location of the particle. Although in this work, the field is designed to be intentionally inhomogeneous for attracting the particles, the field does not vary rapidly across the substantially smaller magnetic nanoparticle diameter, and thus the dipole moment is still expected to be a good approximation. Thus, the total magnetic field at the center of the nanoparticle is due to the field created by the wires of the stent, the field due to other nearby particles, and any externally applied field. If one considers weakly concentrated nanoparticle solutions where particles are separated from one another by at least 10 nanoparticle diameters, then particle-particle interactions are negligible and only direct particle-wire interactions need be taken into account.

The expression (3) defines magnetic force ($F_{mag}$) on a particle as follows:

$$\vec{F}_{mag} = \mu_0(\vec{m}\cdot\nabla)\vec{H} \approx \mu_0 \frac{3\chi}{\chi+3} V(\vec{H}\cdot\nabla\vec{H}) \quad (3)$$

where $\mu_0$ is the magnetic permeability of free space. When modeling hydrodynamic systems, the typical approach is to ignore particle inertia (any particle acceleration happens over time periods that are tiny compared to typical time of particle movement). Thus, the particle velocity can be obtained by equating the magnetic force in (4) to the Stoke's drag force, as given by:

$$\vec{F}_{drag} = 3\pi d\eta(\vec{v}_f - \vec{v}_p) \quad (4)$$

where $\eta$ is the fluid viscosity, d is the particle diameter, $\vec{v}_f$ and $\vec{v}_p$ are the fluid and particle velocities, respectively. In order to obtain a rough estimate for the dynamics of particle capture, consider the case of a particle initially located at a distance D from the wire's center. Assuming the optimal scenario of the particle being located in a stationary fluid, and the wire and nanoparticle magnetizations are aligned collinearly with the vector connecting their two centers, it is possible to obtain an analytical expression for the time interval t it would take to capture a nanoparticle onto the wire's surface of radius R, which is given by expression (5):

$$D = \left[H_0 \frac{2\mu_0 d^2 \lambda(H_0) t}{3\pi\eta} \frac{\chi}{(\chi+3)} - R^4\right]^{1/4} - R \quad (5)$$

wherein $H_o$ is initial magnetic field.

In this analysis, it was assumed that the external magnetic field dominates the wire's field, and hence the wire's contribution to magnetizing the particle was ignored in the above expression. For weakly magnetic materials, such as 316L, this assumption is accurate even when fields of only 10 Oerstad are applied. From (5) it is clear that the most effective control parameters for tuning nanoparticle delivery are the nanoparticle diameter, the external field, the wire magnetization, and the time interval. All of these control parameters have been investigated, and the results from theoretical simulations are shown to be in good agreement with experimental investigations.

Inventors have discovered that magnetic particles of the invention can be delivered to a magnetic implanted device (e.g., a stent) by administration to a body (e.g., an intravenous injection). In that, certain parameters can be manipulated to control the nanoparticle delivery, e.g., the nanoparticle diameter, the external field, the implanted device surface magnetization, and the time interval it would take to capture the nanoparticle onto the surface.

The term "bioactive magnetic particle" as used herein denotes a magnetic particle associated with biomaterial, which is covalently attached to a monomolecular layer formed on the surface of the particle. It should be understood that the term "bioactive magnetic particle" is not limited to particles delivering biomaterial. Any molecules capable of attachment to particles as described above, such as, for example, imaging agent can be used also.

Further provided is method for delivery of a biomaterial to a cell or a tissue, the method comprising: (a) providing a bioactive magnetic particle comprising (1) a matrix having at least one carbon, wherein the matrix is in a shape of a particle having a diameter of about 5 nm to about 10 microns, (2) the water-soluble photo-activatable polymer as a monomolecular layer covalently attached to the matrix by a covalent bond between the photo-activatable group and the at least one carbon; (3) the biomaterial having a plurality of active groups, wherein the biomaterial is covalently attached to the monomolecular layer by covalent bonding between the active groups and the reactive groups; and (4) magnetic field-responsive agent associated with the particle; (b) providing an implant comprising a magnetic surface to the cell or the tissue; (c) administering the bio active magnetic particle to the cell or the tissue; and (d) capturing the bioactive magnetic particle onto the magnetic surface. Administering the bioactive magnetic particle can be done, for example, by injection.

In certain embodiments, delivery of the biomaterial to a cell or a tissue can be manipulated by selecting at least one of a particle diameter, proximity of an external magnetic field, a degree of surface magnetization of the implant, and a time interval for capturing the particle onto the magnetic surface.

Theoretical Simulations

The magnetic properties of all the materials were measured with an alternating gradient magnometer (AGM) (Princeton Measurements Corporation, Princeton, N.J.). Hysteresis curves were generated for the nanoparticles, the bare 316L stainless steel wire, and the 316L stainless steel wire coated with Nickel/Cobalt alloy. From the hysteresis curves, the initial susceptibility of the 380 nm diameter magnetic nanoparticles was found to be in the range of 0.1~1.0, which is consistent with the properties of commercially available materials (Dynal Biotech, NY) composed of approximately 10% magnetite by volume. The magnetic moments of the stent materials were also measured, and their behavior is expressed in terms of moment per unit length to maintain consistency with the wire magnetization parameters used in simulations. The magnetic moment per unit length of the Palmaz-Shatz stent wire was found to relate linearly with the externally applied field $H_0$ in the range of 0 to 5000 Oerstads according to: $\lambda_{316L}=9.2 \cdot 10^{-11}$ $m^2 \cdot H_0 + 3.3 \cdot 10^{-6}$ A·m. The magnetic properties of a similar segment coated with a 20 µm thick layer of NiCo alloy was shown to relate linearly with the externally applied field between 0 and 700 Oerstaeds as: $\lambda_{316L+NiCo}=5.8 \cdot 10^{-8}$ $m^2 \cdot H_0 + 1.2 \cdot 10^{-4}$ A·m, which is two to three orders of magnitude stronger than bare 316L steel.

Theoretical simulations were carried out using MATH-CAD software to demonstrate the feasibility of capturing magnetic nanoparticles with existing unmodified and modified 316L stents implanted in plastic tubes with 3.2 mm inner diameter. A series of simulations were carried out to determine the effect of various control parameters as well as general scaling principles. In all simulations, each nanoparticle was assumed to have initial susceptibility of 0.5, and the particle was assumed to move towards a stent wire of 150 µm diameter through a fluid with a viscosity of 0.03 poise, which is consistent with that of blood. The theoretical design was chosen to simulate a catheter-based nanoparticle delivery device, such as the double balloon catheters, which have the capability of arresting blood flow in certain regions for time frames on the order of 60 seconds. The capture percentage is equal to the ratio of the capture distance in expression (5) with respect to the radius of the plastic tube. The physical meaning of this ratio suggests that if the wire can capture a particle located at a distance of one tube radius, then all particles in suspension can be captured.

The capture percentage was first determined as a function of the applied field. As shown in FIG. 16A, roughly 2-3% of the particles can be captured within the first 60 seconds on bare 316L stainless steel, whereas 20-30% of the particles can be captured in a similar interval on the Nickel/Cobalt modified 316L steel, as shown in FIG. 16B. The inset within each figure is provided to give an indication of the capture dynamics occurring over the first 100 milliseconds, showing the potential of magnetic nanoparticles to be captured in normal physiological flow conditions. Although this model estimate ignores several effects, such as the presence of other stent wires and the edges of the stent itself, as well as lift forces and other hydrodynamic effects induced by the boundary of the arteries, it is believed that an order of magnitude estimate can still be obtained using static capture analysis. Using the simple estimates of 1 cm/s fluid flow rate near the arterial wall and 100 µm diameter wire, it is possible to arrive at a time constant of 10 milliseconds, which is the time interval for which a particle in transit will cross one of the strut wires during blood flow. This analysis indicates that the particle must be captured within the first 10 milliseconds if it has any chance of being delivered by simple intravenous injection. Simulations suggest that bare 316L wire has virtually no chance of capturing nanoparticles within the first pass (<0.01%). Even if "stealth" nanoparticles, which are surface modified (with polyethyleneglycol for example) to prolong their persistence in the circulation, are employed to evade capture by macrophages and allow particles to survive inside the cardiovascular system for 100 passes through the coronary artery, the total capture is not expected to exceed 1%. The Nickel/Cobalt coated 316L steel, by contrast, has a chance of capturing a fraction of particles in each pass (roughly 0.5% per pass). Given a sufficient number of passes this analysis indicates that a large fraction of nanoparticles can be localized on such strongly magnetic stents.

The modeled capture percentage was also analyzed as a function of nanoparticle diameter. Due to general scaling principles, there is an advantage to using larger particles since the magnetic force increases with the cube of particle diameter whereas the drag force increases only linearly with particle diameter. Practically speaking, biological applications would be limited to using particles that can fit through the capillary beds in the cardiovascular system, restricting the maximum size of the particles to around 1000 nm. The capture dynamics of different nanoparticle diameters were simulated and the results are provided in FIG. 3c. In these simulations, the particle's moments were assumed to be saturated by an externally applied 1000 Oerstad field. As expected, over the course of 60 seconds the 1000 nm particles can be captured at higher levels (up to 5%) than the 400 nm particles (up to 2%) used in most of the present experiments.

Experimental Results—In Vitro

Theoretical predictions simulating local delivery of 380 nm sized polylactide-based magnetic nanoparticles to 316L stents were tested experimentally in simple stop-flow conditions. Stents were deployed by balloon catheter in 3.2 mm diameter plastic tubes filled with a buffer simulating blood pH and viscosity. Magnetic nanoparticles were injected into the tube nearby the stent, and then exposed to uniform 1000 Oerstad fields for 60 seconds. As a control, some stents were exposed to magnetic nanoparticles for similar time duration without exposure to an external field. Afterwards, the stents were removed, cut open, pressed flat en face on a glass slide, and imaged by fluorescent microscopy. Examples of the fluorescent images obtained from individual wires of 316L stents are shown in FIG. 17A-F. Figs A-B show representative photos taken from unmodified Palmaz-Shatz stents exposed to magnetic nanoparticles without application of external magnetic field, whereas FIG. 17 C-D show the magnetic nanoparticle accumulation on similar stents after exposure to 1000 Oerstad magnetic field. Quantitative fluorescent analysis revealed that the external field increased particle capture by roughly 10 times over the stents that were not exposed to an external field. FIG. 17 E-F shows the attraction of magnetic nanoparticles to the Palmaz-Shatz stents coated with Nickel/Cobalt alloy in 1000 Oerstad field. The relative fluorescence over commensurate areas was more than 25 times that of the unmodified Palmaz-Shatz stent under comparable conditions.

The percentage of particle capture was evaluated by semi-quantitative fluorescence analysis using a known concentration from the stock solution as a reference. Results suggest that the unmodified 316L steel stent captured roughly 1% (+/−0.3%) of the injected particles, whereas the Nickel/Cobalt coated stent captured roughly 25% (+/−5%) of the injected particles. Estimations were based on a 2.5 $cm^2$ stent surface area, leading to numbers which agree not only qualitatively, but also quantitatively, with theoretical predictions (as above).

Rat aortic smooth muscle cell (A10) culture experiments were used to demonstrate whether the magnetic localization techniques have the potential for therapeutic capabilities. To test for this potential, GFP encoding adenovirus was attached to the nanoparticles and exposed to a confluent layer of A10 cells grown in culture for 1 minute on top of a 316 Stainless Steel Electron Microscopy grid. A number of control protocols employing different formulations or magnetic exposure conditions were used to elucidate the importance of various experimental parameters. The control formulations included Ad added in the presence of nonmagnetic D1-modified NP, nIgG-modified MNP possessing no specific binding affinity for the virus, or free Ad. Control experimental conditions included cell incubation with MNP-Ad complexes in the absence of either magnetic field or a SS grid. Average and standard deviations were taken for each group and are graphically illustrated as the relative gene expression with respect to the average free virus control. As demonstrated in FIG. 18C, significant gene expression occurred only for the experimental set, which consisted of a 316L mesh coated by cells exposed to magnetic nanoparticles in a 500 Oerstad field for 60 seconds, with the virus attached to the particle through the D1 protein. By contrast, the signal was substantially lower for the controls which lacked either the mesh, the field, used non-magnetic particles or free virus, or were surface coated with nIgG instead of D1. The micrographs shown in FIG. 18A-B demonstrate that GFP expression (green) is localized around the mesh (FIG. 18B), and particles (red) are co-localized in the GFP expressing cells (FIG. 18A).

Experimental Results—In Vivo

To validate the concept of magnetic field-facilitated gene vector delivery in vivo a well-characterized rat carotid model was employed. The same amount of Ad-GFP was locally delivered to the isolated balloon-injured segments of carotid arteries, either as free vector, or conjugated to biodegradable magnetic NP. The later mode of delivery was carried out with or without preceding implantation of 316L stainless steel spring (modeling prototype stent) in the artery. Transgene expression was analyzed in the excised arterial sections 7 days after gene vector delivery. Fluorescence microscopy of the arterial sections locally treated with either free (n=5) or magnetic NP coupled Ad-GFP (the later with (n=6) or without (n=5) magnetisable coil pre-implantation) showed qualitatively much higher GFP expression levels when magnetic NP were delivered in conjunction with coil implantation (FIG. 19C vs 19A and 19B).

The invention will be illustrated in more detail with reference to the following Examples, but it should be understood that the present invention is not deemed to be limited thereto.

EXAMPLES

Example 1

Figure 2:
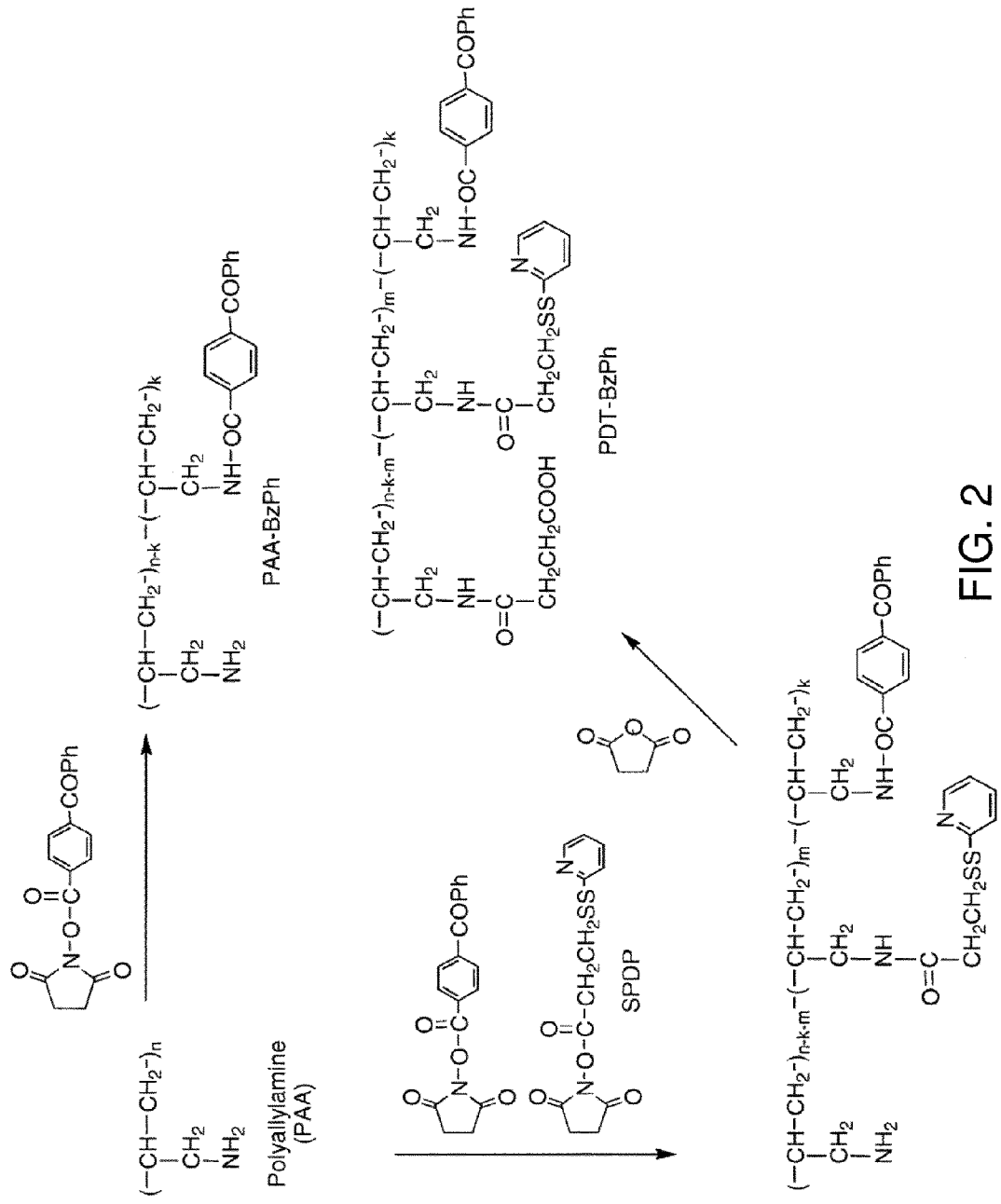
FIG. 2 is a reaction scheme demonstrating synthesis of polymeric multi-point benzophenone modifiers.

Preparation of Water-Soluble Photo-Activatable Polymers Based on Poly(allylamine) Synthesis of PAA-BzPh Synthesis of PAA-BzPh is demonstrated in FIG. 2. Poly(allylamine) (PAA) base was prepared from PAA hydrochloride (Sigma-Aldrich St. Louis, Mo., MW=70 KDa) by treatment in aqueous medium with a strong anionite Dowex G-55 followed by replacement of water by 2-propanol. A 5.1% solution of PAA base in 2-propanol (4.06 g, containing 3.65 mmol of amino groups) was diluted with $CH_2Cl_2$ (7 ml) and cooled on an ice bath. N-succinimidyl 4-benzoylbenzoate (236 mg, 0.73 mmol; synthesized by applicants and available from Toronto Research Chemicals) in $CH_2Cl_2$ (12 ml) was added over a 10-min period. The mixture was stirred near 0° C. for 10 min, then warmed to room temperature and acidified with concentrated HCl (0.24 ml, 2.9 mmol). The resulting suspension was dried in vacuo, resuspended in $CH_2Cl_2$, and the precipitate was filtered off. After washing with $CH_2Cl_2$ and pentane, 0.544 g of PAA-BzPh hydrochloride were obtained. A $^1H$ NMR study of this polymer (utilizing $D_2O$) indicated that 20% of polymer's amino groups were modified with 4-benzoylbenzoic residues (broad signal at 6.9-8.0 ppm). Analogously, using the calculated amount of fluorescein isothiocyanate (FITC) (Sigma-Aldrich, St. Louis, Mo.) simultaneously with N-succinimidyl 4-benzoylbenzoate in the reaction with PAA base, FITC-labeled PAA-BzPh having about 20% of 4-benzoylbenzoic residues and about 2% of the FITC label was prepared.

Synthesis of PDT-BzPh

Synthesis of PDT-BzPh is shown in FIG. 2. 5.1% solution of PAA base in 2-propanol (2.671 g, containing 2.40 mmol of amino groups) was diluted with $CH_2Cl_2$ (5 ml) and cooled on ice. N-succinimidyl 4-benzoylbenzoate (145 mg, 0.45 mmol) and SPDP (Pierce Biotechnology Inc, Rockford, Ill., 281 mg, 0.90 mmol) were simultaneously dissolved in $CH_2Cl_2$ (8 ml) and introduced over a 5-min period. The mixture was stirred near 0° C. for 15 min, and succinic anhydride (130 mg, 1.30 mmol) was added at once. The stirring at 0° C. was continued for 0.5 h, the mixture was dried in vacuo and extracted first with ethyl acetate and then with water. The polymeric residue was dissolved in water (15 ml) with addition of $KHCO_3$ (0.3 g, 3.0 mmol). The solution was filtered and acidified with $H_3PO_4$ to pH of 3.5. The precipitate was filtered off, washed with water, and air-dried PDT-BzPh (488 mg) was obtained. A $^1H$ NMR study of this polymer (utilizing $D_2O$ and $K_2CO_3$ at pH 9) indicated that about 40% of 2-pyridyldithio groups and about 20% of 4-benzoylbenzoic residues were attached to the PAA backbone. The rest of amino groups was modified with 3-carboxypropionyl residues resulting from succinic anhydride.

Example 2

Preparation of Water-Soluble Photo-Activatable Polymers Based on Polyacrylic Acid Polyacrylic acid can be coupled in aqueous solutions simultaneously with amino-derivatized benzophenone compound and a compound (also amino-derivatized) containing one of the reactive groups described above, particularly 2-(2-pyridyldithio)ethylamine. Water-soluble carbodiimide (EDC) can be used for such coupling (see Scheme below).

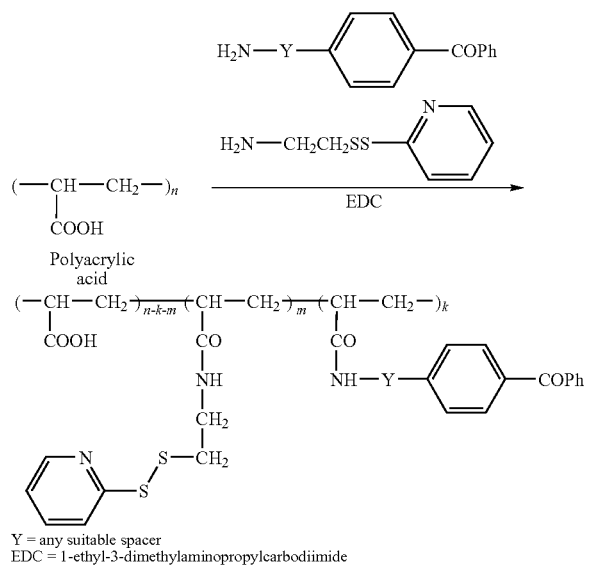

Y = any suitable spacer
EDC = 1-ethyl-3-dimethylaminopropylcarbodiimide

Example 3

Photo-Immobilization of Polymeric Modifiers onto Matrix

Surface Amination of Polymeric Matrix with PAA-BzPh.

An aqueous solution (2 mg/ml) of PAA-BzPh or its FITC-labeled variant was mixed with an equal volume of a buffer containing 0.1M $NH_4OAc$ and 0.05M $NH_3$. PU Tecothane TT-1074A films or polyester (PE) fibers were immersed into the mixture for 5-60 min, rinsed with a 1% solution of $NH_3$ and dried on a filter paper. The polymers were irradiated under an UV-lamp (UVGL-25, long wave) for 15-30 min to achieve the covalent binding of modifiers to the polymer surface. Finally, the surface modified polymers were thoroughly washed with diluted (2%) HCl and water.

Modification of Polymeric Matrix with PDT-BzPh.

PDT-BzPh (30 mg) was dissolved in water (30 ml) by addition of $KHCO_3$ (20 mg) and acidified with a 20% solution of $KH_2PO_4$ (1 ml). PU films and PE fibers were soaked in the resulting mixture for 5-40 min., rinsed with 0.1% acetic acid, dried and irradiated as above. Finally, the polymers were exhaustively washed with 0.1M $KHCO_3$ and water.

Example 4

Fluorescent Labeled PAA-BzPh Studies Demonstrating Attachment of Biomolecules

The presence of modifier bound to the polymer surfaces was confirmed by fluorescence microscopy of PU films and PE fibers surface modified with FITC-labeled PAA-BzPh (pictures are not shown herein).

Example 5

Cell Culture Data Demonstrating Antibody Linkage of Cy3 Labeled GFP-Adenovirus PU Matrix Surface-aminated PU films (group $NH_2$-A) were reacted with LC-sulfo-SPDP dissolved in PBS (9 mg/ml; 1 ml; 90 min). Then, the films were extensively washed in PBS and reacted in 5% BSA with anti-knob Ab (0.66 mg/ml) reduced with 1.5 mg of 2-mercaptoethylamine for 90 min at 37° C. Prior to conjugation, Ab was purified by gel filtration using a desalting column equilibrated with degassed PBS containing 10 mM EDTA. The conjugation was allowed to run for 38 hours at room temperature (RT) under mild shaking. Next, the films were washed in PBSx3 and immersed in the suspension of $10^{11}$ particles of Cy3-labeled adenovirus (Cy3-AdV-GFP) in 1.5 ml of 5% BSA/PBS. Surface aminated films that were not modified by antiknob Ab ($NH_2$—B) served as controls. Immunoconjugation was carried out for 12 hours at RT under mild shaking. Finally, the films were washed in PBS and examined under fluorescent microscope to assess tethering of Cy3-labeled adenoviruses. A uniform virus coverage of the surface was observed for the films conjugated with antiknob Ab, while the control films were virtually non-fluorescent (images are not shown herein).

PDT-BzPh-modified PU Tecothane TT-1074A films were directly modified with the reduced antiknob Ab. After washing the films (PDT-A) along with the control samples, the PDT-BzPh-modified PU samples that were not conjugated with the antiknob Ab (PDT-B), both PDT-A and PDT-B were incubated with Cy3-labeled GFP-AdV. Antibody reduction, purification and conjugation, and virus tethering were carried out according the procedures outlined above. Similar to the results obtained for the surface-aminated PU samples, a uniform fluorescent AdV layer was observed for the Ab-mediated AdV tethering, while no Cy-3-labeled AdV was bound to the surface of control films (images are not shown herein).

PE Matrix

PDT-BzPh-modified PE fibers were reacted with 2 mg of antiknob antibody reduced with 10 mg of 2-mercaptoethylamine at 37° C. for 1 hour. Prior to utilization, the reduced Ab was purified using a desalting column equilibrated with degassed PBS/10 mM EDTA. The conjugation was carried out in 5% BSA/PBS for 20 hours at room temperature under mild shaking.

After PBS ×3 washing, the Ab-coupled fibers were immersed into the suspension of $5 \times 10^{11}$ particles of Cy3-labeled adenovirus in 1.5 ml of 5% BSA/PBS. Immune conjugation was carried out for 14 hours at RT under mild shaking Immobilization of Cy3-AdV on the surface of PDT-BzPh-modified PE fibers was confirmed by fluorescent microscopy (images are not shown herein).

Example 6

Preparation of Nanoparticles (Nps) Surface-Modified with Pdt-Bzph

In the following example, an aqueous dispersion of NPs was prepared by emulsification-solvent evaporation and subsequently surface-modified with PDT-BzPh.

D,L-(poly)lactide (D,L-PLA, Sigma), branched poly(ethyleneimine) (PEI 25K, Aldrich) and Poloxamer 188 (Pluronic F-68, Sigma) were dissolved in 5 ml DCM HPLC grade in amounts of 300 mg, 100 mg and 50 mg, respectively.

Poly(lactide) is a nanoparticle-forming polymer (i.e. constitutes the polymeric matrix of the nanoparticle). Poly(ethyleneimine) makes the nanoparticles cationic, capable of binding anionic substances and contributes to nanoparticles' stability during the emulsification step of their preparation; is not a requisite and can be omitted. Poloxamer 188 is a non-ionic stabilizer, which is required for nanoparticles' stability, it provides sterical stabilization.

The organic solution was emulsified in 15 ml of distilled water on ice-bath at 0° C. using sonication. The solvent was removed by rotary evaporation at 35° C. The NPs were filtered through Whatman paper filter (2.5 µm cut-off). The NP size was determined by Photon Correlation Spectroscopy and was found to be 600 nm. Next, the NPs were dialyzed to remove unbound stabilizers (300 KDa cut-off MW) in distilled water at 4° C. for 48 hr with several water replacements.

2 ml of preformed PLA/PEI nanoparticles were mixed with 1 ml of 0.1% aqueous solution of PDT-BzPh. 50 µl of aqueous solution of 15% $KH_2PO_4$ were added to the reaction mixture to adjust the pH to 5.5. At this pH, PDT-BzPh separates from the solution, presumably associating with the lipophilic surface of the NPs. The total amount of PDT-BzPh in the formulation (1 mg) was calculated to have a 4-fold excess over the estimated amount of the PDT-BzPh needed to establish a monolayer on the surface of PLA/PEI nanoparticles. The reaction mixture was transferred to a round-bottom flask. The flask was rotated (at 100 rpm) causing thin layer distribution of the reaction volume over the flask's walls. The hand-held UV lamp (UVGL-25, UVP) was approximated to the rotating flask, and the reaction mixture was irradiated at about 350 nm from the distance 1-2 cm for 30 min at room temperature. PDT-BzPh-modified NPs (as described in Example 6) were separated from the excess of PDT-BzPh by the dialysis against double distilled water (DDW) through the 300 kDa cut-off membrane (24 hours, 3 changes of DDW).

Example 7

Tethering of Biomolecules to NPs Modified with DPT-BzPh

A thiolated (cysteinated) form of D1 domain of the Coxsackie-Adenovirus receptor (produced in-house according to the procedure described in Nyanguile et al, Gene Ther., 2003; 10:1362-1369) was conjugated to the thiol-reactive NP to impart adeno-virus-tethering properties.

2 mg of D1 was column-desalted in 2.7 ml of degassed PBS supplemented with 10 mM EDTA and mixed with 3.3 ml of PDT-BzPh-modified NP. The coupling reaction was carried out for 14 hours at RT under moderate shaking. D1-derivatized NPs were separated from the excess of D1 by the dialysis against PBS through the 300 kDa cut-off membrane for 36 hours at 4° C. Finally, a 2 ml aliquot of 6 ml dialyzate was mixed with 125 µl of Cy3-modified Ad-GFP ($3.75 \times 10^{11}$ particles). BSA was added to final 5% concentration. Immune conjugation was carried out at room temperature under mild shaking for 12 hours. 2 ml of diluted (1:3) non-modified PLA/PEI NPs were mixed with the same amount of BSA and Cy3-AdV-GFP to serve as control. Tethering of fluorescent Cy3-labeled adenovirus (AdV) to NPs was documented by fluorescent microscopy (images are not shown herein).

Example 8

Preparation of Nanoparticles (Nps) Surface-Modified with PDT-BzPh

An alternative method does not require use of additional stabilizers, such as PEI or Poloxamer 188, relying on the charge stabilization of the NPs provided by the anionic chains of the PDT-BzPh. 200 mg of polylactide labeled with BODIPY 564/570 was dissolved in 5 ml chloroform to form an organic phase. 10 mg of PDT-BzPh was dissolved along with 6.7 mg potassium bicarbonate in 15 ml water (pH ~6.5). The organic phase was emulsified in the aqueous solution by sonication with simultaneous addition of 1 ml MES (2-[N-morpholino]ethanesulfate) buffer (0.1 M, pH 5.5). The organic solvent was removed by evaporation under reduced pressure at 30° C. The obtained particles were filtered through a 1.0 µm glass fiber prefilter (Millipore, Bredford, Mass. USA) and exposed to long-wave UV for 5 min to achieve covalent attachment of PDT-BzPh. The NP were separated from the unbound PDT-BzPh by gel filtration (Sepharose B6 gel, Sigma-Aldrich) using MES buffer (0.01 M, pH 6.5) as an eluent.

Surface-activated NP were reacted with thiolated D1 at room temperature overnight by combining 1.5 ml of NP suspension with 1.5 ml solution containing 0.7 mg protein. Protein-modified NP were separated from the unbound protein by gel filtration and lyophilized with 10% glucose as cryoprotectant. The NP were kept at −20° C. and resuspended in 0.2 ml water before use.

Replication defective Ad vectors (Type 5; E1, E3 deleted) were obtained from the Gene Vector Core Facility of the University of Pennsylvania ($_{GFP}$Ad, $_{LUC}$Ad and $_{NULL}$Ad) and from the Gene Therapy Core Facility of the University of Iowa ($_{iNOS}$Ad). All transgenes were under the control of the CMV promoter. Poly(D,L-lactide) (Mw 75,000-120,000) was obtained from Sigma-Aldrich (St. Louis, Mo., USA). Mouse anti-knob antibody (IgG) was provided by Selective Genetics (San Diego, Calif., USA). Non-immune sheep IgG was obtained from Cedarlane laboratories (Hornby, Ontario, Canada). Recombinant fiber knob protein was prepared by cloning the DNA encoding the knob domain into pET15b (Freimuth et al., 1999) and purified as known in the art (see, e.g., Henry et al., 1994). All chemicals were of analytical grade.

Example 9

Preparation of Nanoparticles (NPs) Surface-Modified with PBPC and PBMC

Poly(allylamine) hydrochloride (Sigma-Aldrich) with number and weight average molecular weights of 8500-

11000 and ca. 15000, respectively, which on average corresponds to nearly 100 units of monomer for each macromolecule, was transformed into poly(allylamine) free base by treatment with a strongly basic anionite Dowex G-55 in OH-form. Poly(allylamine) was modified at 0° C. in anon-aqueous solvent system (2-propanol/$CH_2Cl_2$) by acylation of its amino groups with the corresponding N-hydroxysuccinimide esters to form pendant photoreactive (benzophenone) and either pyridyldithio or maleimide groups. The unreacted amino groups were quenched with succinic anhydride resulting in pendant carboxylic groups (FIG. 14). The conditions used for the modification virtually eliminated the possibility of side reactions, such as hydrolysis of the active esters. The molar ratio between the attached functional groups could be readily controlled by the amounts of the corresponding reagents and was chosen to be 1:2:2 for benzophenone, thiol-reactive and succinamoic residues, respectively). The products consisting of poly(allylamine) randomly N-acylated with residues of 4-benzoylbenzoic, succinic, and 3-(2-pyridyldithio) propionic or 6-maleimidocaproic acids were isolated as free acids and analyzed by $^1$H NMR (in $D_2O/KDCO_3$ or DMSO-$d_6$ used for the two derivatives abbreviated PBPC and PBMC, respectively). Aromatic protons of pendant benzophenone residues appeared in $D_2O/KDCO_3$ as a broad band at 6.5-8.0 ppm, whereas in DMSO-$d_6$ 3 close bands (with maxima at 7.46, 7.68 and 7.98 ppm) were observed. Pyridyldithio groups (in $D_2O/KDCO_3$) showed 3 bands of protons with maxima at 8.2 (1H), 7.5 (2H) and 7.0 (1H) ppm. Maleimido groups (in DMSO-$d_6$) exhibited a narrow band with a maximum at 6.93 ppm. $CH_2$ of succinamoic residues showed up at 2.4 ppm (both in $D_2O/KDCO_3$ and DMSO-$d_6$) overlapping with other signals of the polymer's protons.

Surface-activated NP were prepared by a modification of the emulsification-solvent evaporation method (Quintanar-Guerrero et al., 1998; Rosca et al., 2004). In a typical preparation, two hundred mg of polylactide covalently labeled with BODIPY 564/570 (Molecular Probes, Eugene, Oreg. USA) was dissolved in 5 ml chloroform to form an organic phase. Ten mg of the surface activating agent synthesized as above was dissolved along with 6.7 mg potassium bicarbonate in 15 ml water. The organic phase was emulsified in the aqueous solution by sonication with simultaneous addition of 1 ml MES (2-[N-morpholino]ethanesulfate) buffer (0.1 M, pH 5.5). The organic solvent was removed by evaporation under reduced pressure at 30° C. NP were filtered through a 1.0 μm glass fiber prefilter (Millipore, Bredford, Mass. USA) and exposed to long-wave UV for 5 min to achieve covalent attachment of PBPC or PBMC. The NP were separated from the unbound agent by gel filtration (Sepharose B6 gel, Sigma-Aldrich) using MES buffer (0.01 M, pH 6.5) as an eluent.

The human recombinant D1 domain of CAR was prepared as described previously (Nyanguile et al., 2003) and PCT Application Serial No. PCT/US04/026509 by inventors, incorporated herein in its entirety. D1 obtained in the form of thio ester was reacted with cysteine (20 mg/ml) and purified by gel filtration using a Polyacrylamide 6000 column (Pierce, Rockford, Ill. USA). Two mg of antiknob antibody or non-immune IgG was reduced with 5.0 mg of 2-mercaptoethylamine in 1 ml MES buffer (0.01 M, pH 6.5) for 1 hr at 37° C. and purified by gel filtration using Sepharose B6 gel.

Surface-activated NP were reacted with thiolated D1 or reduced IgG at room temperature overnight by combining 1.5 ml of NP suspension with 1.5 ml of a solution containing 0.7 mg protein. The total number of surface-associated pyridyldithio groups and the protein-particle binding were determined by measuring the characteristic absorbance of pyridine-2-thione formed in the course of the reaction with dithiothreitol and the protein, respectively (Hermanson, 1996), in the particle suspending medium (λ=343 nm). Protein-modified NP were separated from the unbound protein by gel filtration and lyophilized with 10% glucose as a cryoprotectant. The NP were kept at −20° C. and resuspended in deionized water before use. NP size was determined using photon correlation spectroscopy (Brookhaven Instruments, Holtville, N.Y. USA).

NP formulated and surface-activated as described above formed a colloidally stable suspension over 14 days with a narrow size distribution in the submicron range (305±40 nm). It was observed that pyridyldithio (PDT) functional groups in the composition of the polymer used for NP surface activation remained stable upon storage under argon at 4° C. maintaining their thiol reactivity for over 14 days. 15% of the PBPC polymer initially used to prepare the formulation was found to be associated with the NP, corresponding to about $4.5 \times 10^5$ of PDT groups per particle as calculated from the amount of pyridine-2-thione formed in the course of the reaction. The reaction with thiolated D1 protein was rapid, resulting in ca. $3.3 \times 10^4$ of surface-immobilized Ad binding proteins per particle after 2 hr. A similarly rapid reaction was observed with reduced non-immune IgG used for surface modification of control particles (results not shown). The modification of the NP with the proteins of interest led to an increase in the particle size from 305±40 nm to 409±55 nm and 457±53 nm for the D1-coated NP ($_{D1}$NP) and non-immune IgG-coated NP ($_{nIgG}$NP), respectively. Transmission electron microscopy confirmed formation of $_{D1}$NP-Ad complexes with each individual nanoparticle capable of immobilizing numerous viral units on its surface (see FIGS. 8A-8B).

Example 10

AdV Immobilization on the NP Surface

See FIGS. 5, 6A-C and 7 A-F

Surface Activation Agent Requirements:
1. preferably localizes on the particle surface (amphiphilic);
2. capable of multiple point covalent surface-attachment to provide stable NP-AdV association; and
3. bears thiol-reactive groups minimally affected by a short-term UV exposure.

Fluorescently labeled 370 nm NP and AdV incubated for 2 hr at 1:1 ratio in MES buffer, pH 6.5. Magnification is ×200. Note the substantial co-localization of the signal. Transmission electron micrograph shows a composite negatively stained with 2% uranyl acetate.

Fluorimetry and fluorescent microscopy of live cells:
Smooth muscle cells (A10), blood origin endothelial cells (BOEC) and heart endothelioma cells (H5V) were seeded at 104/well on 96-well plates. GFP or inducible NO synthase (iNOS) encoding AdV was incubated for 1 hr with varying concentrations of non-immune IgG- or D1-coated NP (0-4.0 μg PLA or $0-1.5 \times 10^8$ particles/well) and applied to the cells in 10% FBS-supplemented DMEM for 2 hr.

NP uptake:
NP were labeled with BODIPY 564/570; measured using RED fluorescence channel (544/580).

Transduction efficacy:
GFP was determined using GREEN fluorescence channel (485/535).

Cell appearance:
Fluorescent microscopic observation
The effect of knob fiber protein on the transduction and uptake of composite-forming NP measured as a function of NP dose in smooth muscle cells (A10).

The cells were pretreated with knob (5 µg/ml) for 1 hr prior to addition of AdV (2×108/well) in the presence of D1NP (0-4 µg PLA/well), or nIgGNP used as a control. Knob containing cell medium was aspirated; the cells were washed with PBS and incubated for 2 hr with the formulations. Gene expression was assayed 2 days post treatment.

Biodegradable polymer based NP-AdV composites were formulated using a vector-specific affinity attachment strategy (with D1). The composites were effectively taken up by vascular cells via a CAR-independent pathway resulting in a potent gene transfer in vitro. No non-specific cell toxic effects were associated with the composites in the studied dose range. The ability to deliver therapeutic genes was demonstrated using composites formulated with iNOS AdV that significantly inhibited growth of smooth muscle cells in good correlation with the GFP reporter expression. The growth inhibitory effect is of relevance for gene therapy of cardiovascular disease and needs further evaluation in vivo.

Example 11

Cell Culture Experiments with NP

Rat aortic smooth muscle cells (A10) and murine heart endothelioma cells (H5V) were grown in DMEM medium supplemented with 10% fetal calf serum (FCS). Sheep blood outgrowth endothelial cells were obtained from freshly drawn peripheral blood (Lin et al., 2000) and cultured in EGM-2 medium (Cambrex, East Rutherford, N.J.) supplemented with 5% fetal calf serum (Cambrex) on tissue culture dishes precoated with acetic acid denatured collagen. The cells were seeded on clear bottom 96-well plates at a density of 104 or 3×103 cells/well for reporter expression and growth inhibition studies, respectively. NP were combined with Ad in MES buffer (0.01 M, pH 6.5) containing 5% albumin to prevent non-specific binding, left on a shaker for 1 hr at room temperature, then diluted with respective medium at a volume ratio of 1:4. The cells were incubated with the formulation of interest (100 µl/well) for 2 hr and the medium was replaced after washing with PBS. NP uptake and GFP expression were assayed fluorimetrically in live cells using $\lambda em/\lambda ex$ of 485 nm/535 nm and 544 nm/580 nm, respectively. In the knob competition experiment A10 cells were incubated for 2 hr with DINP-Ad or equivalent amounts of Ad and nIgGNP used as a control (2×108/well and 0-4 µg PLA/well, respectively) after pretreatment with 5 µg/ml knob for 1 hr. Growth inhibition of A10 cells was determined using the Alamar Blue assay as described by the manufacturer (Biosource, Camarillo, Calif. USA). All cell culture experiments were carried out in triplicates.

Example 12

The Extent of Gene Transfer by NP-Ad Complexes In Vitro

To determine the effect of Ad association with NP on the uptake of the complexes and level of gene transfer in different cell types, the NP-Ad were added to cultured rat aortic smooth muscle cells (A10), sheep endothelial precursor cells (BOEC) and murine endothelioma cells (H5V). The latter cell type was chosen as an example of a CAR-deficient cell line (Ogawara et al., 2004). The cellular uptake of D1NP-Ad was proportional to the NP dose, and was equally efficient in A10 and BOEC cells, being slightly higher for H5V (FIGS. 9 A and B). The amounts of the NP resident inside the cells decreased gradually over 72 hours with comparable NP retention levels averaging for all cells types $61\pm3\%$ and $54\pm4\%$ of the initially measured amounts for the D1NP and nIgGNP, respectively, administered at a dose of 1.6 µg PLA/well (FIG. 9 B). Ad immobilization on D1NP effectively increased gene transfer in all types of cells in a NP dose dependent fashion in comparison to free Ad ($p<0.001$) or Ad in the presence of control nIgGNP ($p<0.001$, FIGS. 7 A-F) despite the comparably high internalization of the two NP types, suggesting a lack of stable NP-Ad association in the control formulation. The transduction rates by the NP-Ad correlated with the permissivity for gene transfer by free Ad in the three cell types, with BOEC and H5V exhibiting the highest and the lowest transduction efficiencies, respectively. While the amount of the GFP continued to increase over a 72 hr period in A10 and BOEC (FIGS. 7 D, 7E), the gain in the extent of gene transfer mediated by D1NP-Ad (expressed as the fold increase in comparison to cells treated with equal amounts of nIgGNP and Ad) was the highest 1 day post treatment in these cell lines (5.3- and 3.4-fold, respectively, at 1.6 µg PLA/well). In contrast, GFP expression in the H5V cells treated with D1NP-GFPAd continuously increased in a near-linear fashion for 7 days (results not shown), while the reporter levels in the control cells treated with nIgGNP remained slightly above the detection limit of the assay (FIG. 7 F).

The effect of knob protein on cellular uptake and gene transfer by NP-Ad complexes will now be described.

Pretreatment of cultured smooth muscle cells with knob protein resulted in a substantial inhibition of gene transfer by Ad applied in the presence of control nIgGNP, as well as free Ad ($53\pm4\%$, FIGS. 6 A, 6B) in agreement with its receptor-dependent cell entry. In contrast, when Ad was administered with D1NP (FIGS. 6A-C), the inhibitory effect of the knob pretreatment on the transduction decreased with the NP dose ($13\pm8\%$ at 4.0 µg PLA/well), corresponding apparently to an increase in the fraction of Ad transported into the cells in a NP surface-immobilized form. These results support the view that cellular uptake of the NP-Ad involves a CAR-independent transport mechanism. Receptor-uncoupled transport of the Ad formulated in D1NP-based complexes is also supported by similar rates of the D1NP uptake by smooth muscle cells with or without knob pretreatment (FIG. 6 C).

The effect of the type of NP-Ad binding will now be described.

The NP-Ad complexes taken up by cells would come in contact with the reducing environment of the cell interior (Saito et al., 2003) where the disulfide linkage of the Ad binding protein molecule to the particle surface could hypothetically be cleaved to release the virus from the carrier particle and allow it enter the intracellular processing leading eventually to the expression of the gene. Alternatively, the entry of the virus into the intracellular processing pathway may involve the dissociation of the affinity bond between the Ad binding protein and the knob protein of the virus, or it may occur through decomposition of the virion shell. To elucidate the significance of the cleavable disulfide bond that links either D1 or antibody to NP, we used the PBMC derivative incorporating maleimido (MI) groups that form non-biodegradable C—S bonds upon reaction with thiols, but otherwise is analogous to the PBPC surface modification that results in PDT-based derivatization (FIG. 10 A). The NP modified with either of the two polymers was formed with comparable size distributions ($305\pm40$ nm and $303\pm36$ nm for PDTNP and MINP, respectively). Internalization of the NP-Ad prepared with MI-activated NP was comparable to that observed with the PDT derivative both in terms of efficiency and the linear pattern of the dependence on the particle dose (FIG. 10 B). In accordance with the similarly efficient cellular uptake, a comparable time course of gene expression and transduction rates were exhibited by the two formulations (FIGS. 10 C and 10 D) with MINP being slightly superior in efficiency at higher NP doses, suggesting that the biodegradable linkage between the NP and the Ad binding protein does not contribute significantly to the mechanism responsible for the potentiation of gene transfer by NP-Ad.

Virus immobilization using D1 vs. anti-knob antibody will now be described.

A knob-specific monoclonal IgG antibody that has previously been shown by our group to provide affinity-based attachment of Ad to solid surfaces with effective delivery of the vector in vitro and in vivo (Klugherz et al., 2002), was investigated here in comparison to D1 for the surface immobilization of Ad on biodegradable NP. While control nIgGNP were unable to potentiate viral gene transfer at any dose as was shown in another series of experiments (FIGS. 7A-F), anti-knob IgG-coated NP (AKNP) applied at 0.8 mg PLA/well increased the gene expression in A10 cells by a factor of 7 to 11 (FIG. 11A) compared to free Ad. The greatest increase in gene transfer efficiency was achieved at the lowest dose of Ad applied ($8.4 \times 10^7$/well). The transduction levels of the AKNP-based formulation amounted to 50% to 80% of that of D1NP at the above particle concentration (FIG. 11B). However, in contrast to D1, the potentiating effect of the AKNP decreased for the higher NP doses (1.6-4.0 µg PLA/well) resulting in a poor dose dependence ($p<0.001$ and $p=0.97$ for D1NP and AKNP, respectively). The decrease in efficiency at particle doses higher than 1.6 µg PLA/well was associated with the extensive formation of large-sized aggregates (data not shown) that was detected by fluorescent microscopic examination and was not observed in the presence of either D1NP or nIgGNP. The NP aggregation was triggered by addition of Ad manifesting colloidal destabilization of the carrier particles upon binding increasing amounts of Ad, and this strongly affected the cell entry of the complexes apparently resulting in suboptimal intracellular levels of the gene vector. Additionally, the rate of Ad entering its intracellular processing following internalization might be compromised by entrapment in aggregated particle clusters.

A substantially larger amount of perinuclearly localized D1NP was observed in all cells 24 hours post treatment in comparison to AKNP (FIG. 12 (samples A and B)), the latter also showing a less uniform distribution between the cells. The level of the gene expression was correspondingly higher for D1NP-Ad than for AKNP-Ad formed at the highest NP dose (FIG. 12 (samples D and E)), while cells treated with free Ad showed the lowest transduction rates (FIG. 12 (sample F)).

The effect of NP-iNOSAd complexes on arterial smooth muscle cell growth will now be described.

The extent of iNOSAd-mediated A10 cell growth inhibition was significantly greater with D1NP as compared to control nIgGNP ($p<0.001$ and $p=0.07$, respectively) amounting to 66% and 22% at the highest tested amounts of the NP and Ad (FIGS. 4 A, 4 B) per cell proliferation assay results. In addition, cell growth was examined following treatment with the GFPAd- and null Ad-carrying formulations (FIG. 4 C, 4 D). These controls were included in order to estimate the effect of the complexes mediating transfer of a gene with no specific cell inhibitory activity, as well as the effect of the formulation per se in the absence of gene expression. While the cell growth was not strongly affected by the NP dose of the null vector-based formulation ($p=0.19$), a substantial cell growth inhibition increasing with the NP dose was evident following treatment with NP-GFPAd ($p<0.001$), and could be attributed to the gene product expressed and accumulated at high levels in the cells. The nonspecific effect of GFP on the rate of cell growth however remained notably lower than that of iNOSAd associated with higher doses of D1NP (23% vs. 66%, respectively, at the highest tested amounts of the NP and Ad). The strong direct dose dependence of the cell growth inhibition on both NP and Ad exhibited by the D1NP-iNOSAd, and the notably weaker dependence on the particle dose observed in the presence of nIgGNP were paralleled by the GFP expression pattern (FIGS. 4 E, 4 F): a direct dose dependence was characteristic of D1NP with saturation reached at a particle dose of 3.2 µg PLA/well ($p<0.001$), while control NP had no significant potentiating effect ($p=0.08$).

Example 13

In Vivo Gene Expression

Animal procedures were performed in compliance with NIH standards pertaining to the care and use of laboratory animals utilizing a protocol approved by the I.A.C.U.C. of The Children's Hospital of Philadelphia. Sprague-Dawley rats (male, 100-110 g) were anesthetized using a mixture of ketamine and xylazine (80 mg/kg and 5 mg/kg, respectively) followed by a subcutaneous injection in dorsal caudal region with a 100 µl suspension containing either free LUCAd (n=5, $8 \times 10^9$ viral particles per animal) or D1NP-LUCAd complex (n=4, $8 \times 10^9$ viral particles combined with DINP at a dose of 150 µg PLA per animal). One and five days post treatment the animals were anesthetized, injected in the tail vein with luciferin (60 mg/kg) and the bioluminescence was both imaged and quantitatively measured using the IVIS 100 imaging system (Xenogen Corporation, Alameda, Calif. USA) 15 minutes after injection with a signal acquisition time of 20 sec.

$_{D1}$NP-$_{LUC}$Ad complexes subcutaneously administered to rats resulted in a localized luciferase expression that was 3.7-fold higher than that produced by free $_{LUC}$Ad 1 day post treatment ($p=0.016$, FIG. 13 A). The expression at one day was the strongest at the injection sites and had a similar concentric spatial distribution in the $_{D1}$NP-$_{LUC}$Ad and free $_{LUC}$Ad treated animals. At 5 days $_{LUC}$Ad expression was at comparable levels in both free Ad and Ad-NP groups; it is of interest that this reflected a 16-fold reduction in the Ad-NP expression level noted at 1 day. This most likely reflects mobilization of the transduced cells in the subcutaneous injection site during the period between the 1 and 5 day data acquisition points.

Example 14

Preparation of Magnetic Particles

Magnetically-responsive particles can be prepared similarly to the procedure described in Examples 6 and 7 using ultra small iron oxide nanocrystals dispersion in chloroform instead of pure chloroform as stated in the procedure above. Such dispersion can be obtained by precipitation of aqueous ferrous chloride or its co-precipitation with ferric chloride in an alkaline aqueous solution and further stabilized with a fatty acid (See De Cuyper M, Joniau M. Magnetoliposomes. Formation and structural characterization. Eur Biophys J 1988;

15:311-9; Khalafalla S E. Magnetic fluids, Chemtech 1975, September: 540-7) that also imparts a degree of lipophilicity to the nanocrystal surface depending on the hydrocarbon chain length and the coating density. Such coated nanocrystals can further be extracted into or re-suspended in chloroform as well as other organic solvents, such as dichloromethane, tetrahydrofuran, acetone etc., which can be used for polymer-based particle formulation by the methods mentioned above.

Example 15

Delivery of Magnetic Particles bearing Biomaterial

Magnetic Particle Materials were as follows: Poly(D,L-lactide) (MW 75,000-120,000), (poly)allylamine hydrochloride (MW 15,000), oleic acid, sepharose beads (45-165 µm), iron (II) chloride tetrahydrate and iron (III) chloride hexahydrate were purchased from Sigma-Aldrich (St. Louis, Mo., USA). BODIPY 564/570 succinimidyl ester was purchased from Molecular Probes (Eugene, Oreg., USA). All other reagents were of analytical grade.

Magnetic Implant Materials were as follows: Palmaz-Shatz Stents composed of 316L grade stainless steel were obtained from Cordis (Warren, N.J.). The stents were approximately 1.5 cm in length, and 2.7 mm in diameter in the unexpanded state. The wire struts had cross-sectional dimensions of approximately 300 µm wide and 100 µm thick. Electron microscopy grids composed of 316 grade stainless steel (E-0200) were purchased from Electron Microscopy Sciences (Hatfield, Pa.). The electron microscopy grids consisted of a mesh of wires having cross-sectional dimensions of approximately 40 µm wide and 20 µm thick and having a 120 µm pitch.

Electroplating materials were as follows: cobalt (II) chloride hexahydrate, nickel (II) chloride hexahydrate, saccharin, and boric acid were purchased from Sigma Aldrich. A model 363 Potentiostat/Galvanostat was purchased from AMETEK Princeton Applied Research (Oakridge, Tenn.) for current control of up to 1 Ampere.

Cell Culture Materials were as follows: phosphate buffer saline (PBS) with Ca and Mg, phosphate buffer saline (PBS) without Ca and Mg, trypsin-EDTA 1×, and Fetal Bovine Serum (FBS) were purchased from Invitrogen, Inc. (Grand Island, N.Y.), DMEM 1× was purchased from Mediatech, Inc. (Hernandon, Va.).

Nanoparticles were prepared as follows. A thiol- and photoreactive polymer, PBPC, for the nanoparticle surface chemical activation was synthesized. Magnetic nanoparticles were prepared by a modification of the emulsification-solvent evaporation method. Ferrous and ferric chlorides were dissolved in water, and mixed iron oxide was obtained by precipitation with 1 N sodium hydroxide. Oleic acid was added to the mixture containing the precipitate, and heated to 90° C. in water bath for 5 min with stirring. The precipitate was washed with ethanol and resuspended in chloroform. Poly(D,L-lactide) covalently labeled with BODIPY 564/570 was dissolved in the mixed iron oxide suspension in chloroform to form an organic phase. The organic phase was emulsified in the aqueous solution containing PBPC. Subsequently, the chloroform was evaporated under reduced pressure; the particles were filtered through a 1.0 µm glass fiber prefilter, and irradiated for 5 min with long-wave UV to effect covalent surface attachment of PBPC to make nanoparticles thiol-reactive. The thiol-reactive were separated from the unbound polymer by gel filtration on sepharose gel.

Nanoparticle modification with recombinant D1 protein: Human recombinant D1 domain of the Coxsackie-adenovirus receptor was prepared as described above and reacted in the form of thioester with cysteine (20 mg/ml) to obtain thiolated D1. 2 mg of sheep non-immune immunoglobulin (nIgG) obtained from Cedarlane laboratories (Hornby, Ontario, Canada) and used as a control was reduced with 2-mercaptoethylamine (5 mg) in 1 ml IVIES buffer (0.01 M, pH 6.5); both proteins were purified by gel filtration. Thiol-reactive NP were reacted overnight with thiolated D1 or reduced nIgG (0.7 mg) by combining 1.5 ml of NP suspension with 1.5 ml protein solution. Protein-coated NP were separated from free protein by gel filtration and lyophilized with 10% glucose as cryoprotectant. The NP were kept at −20° C. and resuspended in 0.2 ml water before use. NP size was determined using photon correlation spectroscopy (Brookhaven Instruments, Holtville, N.Y. USA).

Stent Metallization: A solution of 0.8 M $NiCl_2$, 0.25 M $CoCl_2$, 30 g/L $H_3BO_3$, and 1 g/L Saccharin was prepared at a pH of 3. An electroplating bath containing 400 mL of the stock solution was heated to 60° C., and a 0.05 Ampere current (corresponding to ~2 $A/mm^2$ current density) was passed through the stent (having roughly 2 $cm^2$ surface area) for a total of 5 minutes using Cobalt sheet metal as the counter electrode. About 10% of the stent's original weight was added by this process.

Stent-Nanoparticle Magnetic Uptake: The Palmaz-Shatz stents were mounted on a BxVelocity balloon expandable stent system obtained from Cordis (Miami Lakes, Fla.) and expanded into 3.2 mm diameter tubes purchased from United States Plastic Corp (Lima, Ohio). A stock vial of lypholized magnetic nanoparticles was dissolved in 0.05 M Hepes buffer containing 0.9% NaCl, 5% albumin, and adjusted to pH 7.4. One fifth of the stock volume was injected into the tube nearby the stent, and the tube was exposed to uniform 1000 Oerstad field for 60 seconds by holding the tube in between two solenoid coils with iron cores. After sixty seconds, the stents were explanted from the tubes, cut open, pressed flat en face onto a glass slide, and imaged in a Nikon Eclipse TE300 Microscope. The 535/580 channel was used to view the BODIPY label incorporated into the nanoparticles. Six representative stent wires were selected for each group. A histogram reading was employed to quantify the average luminosity of each wire in the photograph and the values were subtracted from the background in the same photograph. The stent wires in each photograph have planar dimensions of 210 µm by 860 µm. As a reference, the original stock volume of nanoparticles was diluted one hundred fold, and then 24 was dispensed into a glass slide and allowed to evaporate. The average luminosity of a representative area of the drop, equivalent to the region used to image the stent wire, was quantified and compared to the luminosity of the experimental groups. The total area of the evaporated drop was 5.3 $mm^2$, which allowed for quantification of the fraction of injected nanoparticles that were trapped by the stent wire. The total surface area of the stent was estimated to be 2.5 $cm^2$ by counting the number of wires and surface area for each wire in the stent. By this method, the fraction of captured nanoparticles was deduced from the original amount injected.

Nanoparticle-Magnetic Mesh: A sterilized mesh was placed in each well of a 24 well plate, and 500 µL of rat aortic smooth muscle cells (A10 cells; ATCC, Gaithersburg, Md.) at Passage 68 were seeded at a concentration of $10^5$ cells/mL onto the mesh at the bottom of the 24 well plate. The cells were allowed to attach to the mesh and substrate for 72 hours. After reaching confluency, 2.0 µl of replication defective Type 5 (E1, E3 deleted) GFP-encoding adenovirus obtained from the Gene Vector Core Facility of the University of Pennsylvania ($5.3 \times 10^{12}$/ml) was mixed with MES buffer (0.01 M, pH7.4) containing 10% albumin. Then, 200 µl of the nanoparticles (surface-modified with D1 or nIgG as a control, were dispersed in 1.6 ml MES buffer. The two were mixed (typically 0.5 ml of virus with 0.5 ml of particles) and incubated at room temperature for 30 min. Finally, 4.0 ml medium supplemented with 12.5% FBS was added to each particle preparation. The groups (triplicates) were exposed to the Ad-nanoparticle complexes for 1 minute in the conditions noted below and the medium was replaced with fresh DMEM after washing the cells 3 times to remove the complexes. Then, the 24 well plates were placed in the incubator and periodically evaluated for GFP gene expression.

Fluorescent Microscopy: The smooth muscle cell cultures were rinsed each day with PBS with Mg & Ca, and each well was mapped in the SpectraMax Gemini EM Fluorescent Scanner (Molecular Devices, Sunnyvale, Calif.). The wells were divided into 1 mm square sections (9 by 9) and scanned using 485/510 excitation and emission wavelengths. The maximum fluorescent signal in each well was averaged for each of the groups and mapped as a function of time.

Local Arterial Delivery in Rat Model: Male Sprague-Dawley rats (450-500 g) underwent a denudation angioplasty injury of the common carotid artery with a 2F Fogarty catheter. The animals were then randomized into three groups: 1) Ad-GFP intraluminal delivery with no magnetic field applied (n=5), 2) Ad-GFP/magnetic NP delivery+magnetic field (n=5), and 3) Ad-GFP/magnetic NP delivery with pre-implanted 316 L stainless steel spring+magnetic field (n=6). In all groups delivery with or without magnetic field enhancement was carried out for one minute into isolated Fogarty-injured segment of common carotid artery. After delivery in the groups 2 and 3 a magnetic field (150 Gauss) was applied for the first 10 mm of reperfusion.

To prepare gene vectors for local delivery $4.5 \times 10^{10}$ particles of Ad-GFP were mixed with 200 µl of reconstituted suspension of lyophilized magnetic NP-D1. For control purposes (group 1) the same amount of Ad-GFP was diluted in 200 µl of 0.01 M MES buffer.

The animals were sacrificed on the day 7 after delivery. After coil removal (where applicable), the arteries were embedded in OCT, cut and examined by fluorescence microscopy.

Statistical Methods: Data are expressed as means±standard error (mean±se). The significance of differences between means of experiment groups was determined using Student t tests.

REFERENCES

[1]. AMOS R A, ANDERSON A B, CLAPPER D L, DUQUETTE P H, DURAN L W, HOHLE S G, SOGARD D J, SWANSON M J, GUIRE P E, (1995) Biomaterial surface modification using photochemical coupling technology. In: Wise D L, Trantolo D J, Altobelli D E, Yaszemski M J, Gresser J D, Schwartz E R editors. Encyclopedic handbook of biomaterials and bioengineering, Part A: materials. New-York: Marcel Dekker Inc. p. 895-926.

[2]. WETZELS G M R, KOOLE L H, (1999). Photoimmobilization of poly(N-vinylpyrrolidone) as a means to improve haemocompatibility of polyurethane biomaterials, Biomaterials, 20, 1879-87.

[3]. MCCLUNG W G, CLAPPER D L, HU S-P, BRASH J L, (2001) Lysine-derivatized polyurethane as a clot lysing surface: conversion of absorbed plasminogen to plasmin and clot lysis in vitro, Biomaterials, 22, 1919-24.

[4]. ALDENHOFF Y B J, BLEZER R, LINDHOUT T, KOOLE L, (1997). Photo-immobilization of dipyridamole (Persantin®) at the surface of polyurethane biomaterials: reduction of in vitro trombogenicity, Biomaterials 18, 167-72.

[5]. KUIJPENS J M H, KARDAUN G A, BLEZER R, PIJPERS A P, KOOLE L H, (1995). Immobilization of theophylline on medical-grade polyurethane inhibits surface-induced activation of blood platelets, J. Am. Chem. Soc. 117, 8691-8697.

[6]. SCHERER ET AL., (2002). "Magnetofection: Enhancing and Targeting Gene Delivery by Magnetic Force in Vitro and in Vivo", Gene Therapy 9, pp. 102-109.

[7]. BAKER, A. H. (2004). Designing gene delivery vectors for cardiovascular gene therapy. Prog Biophys Mol Biol 84, 279-299.

[8]. BRUNETTI-PIERRI, N., PALMER, D. J., BEAUDET, A. L., CAREY, K. D., FINEGOLD, M., and NG, P. (2004). Acute toxicity after high-dose systemic injection of helper-dependent adenoviral vectors into nonhuman primates. Hum Gene Ther 15, 35-46.

[9]. FREIMUTH, P., SPRINGER, K, BERARD, C., HAINFELD, J., BEWLEY, M., and FLANAGAN, J. (1999). Coxsackie virus and adenovirus receptor amino-terminal immunoglobulin V-related domain binds adenovirus type 2 and fiber knob from adenovirus type 12. J Virol 73, 1392-1398.

[10]. HAIM, H., STEINER, I., and PANET, A. (2005). Synchronized infection of cell cultures by magnetically controlled virus. J Virol 79, 622-625.

[11]. HENRY, L. J., XIA, D., WILKE, M. E., DEISENHOFER, J., and GERARD, R. D. (1994). Characterization of the knob domain of the adenovirus type 5 fiber protein expressed in *Escherichia coli*. J Virol 68, 5239-5246.

[12]. HERMANSON, G. T. (1996). Thiol-Reactive Chemical Reactions. In Bioconjugate Techniques. (Academic Press, San Diego).

[13]. HUGHES, C., GALEA-LAURI, J., FARZANEH, F., and DARLING, D. (2001). Streptavidin paramagnetic particles provide a choice of three affinity-based capture and magnetic concentration strategies for retroviral vectors. Mol Ther 3, 623-630.

[14]. KLUGHERZ, B. D., SONG, C., DEFELICE, S., CUI, X., LU, Z., CONNOLLY, J., HINSON, J. T., WILENSKY, R. L., and LEVY, R. J. (2002). Gene delivery to pig coronary arteries from stents carrying antibody-tethered adenovirus. Hum Gene Ther 13, 443-454.

[15]. LAURENCIN, C. T., and ELGENDY, H. (1994). The biocompatibility and toxicity of degradable polymeric materials: implications for drug delivery. In Polymeric site-specific pharmacotherapy. A. J. Domb, ed. (John Wiley & Sons Ltd, Massachusetts) pp. 27-43.

[16]. LIN, Y., WEISDORF, D. J., SOLOVEY, A., and HEBBEL, R. P. (2000). Origins of circulating endothelial cells and endothelial outgrowth from blood. J Clin Invest 105, 71-77.

[17]. LIU, H. S., JAN, M. S., CHOU, C. K., CHEN, P. H., and KE, N. J. (1999). Is green fluorescent protein toxic to the living cells? Biochem Biophys Res Commun 260, 712-717.

[18]. LORTAT-JACOB, H., CHOUIN, E., CUSACK, S., and VAN RAAIJ, M. J. (2001). Kinetic analysis of adenovirus fiber binding to its receptor reveals an avidity mechanism for trimeric receptor-ligand interactions. J Biol Chem 276, 9009-9015.

[19]. LUO, D., and SALTZMAN, W. M. (2000). Enhancement of transfection by physical concentration of DNA at the cell surface. Nat Biotechnol 18, 893-895.

[20]. MAH, C., FRAITES, T. J., JR., ZOLOTUKHIN, I., SONG, S., FLOTTE, T. R., DOBSON, J., BATICH, C., and BYRNE, B. J. (2002). Improved method of recombinant AAV2 delivery for systemic targeted gene therapy. Mol Ther 6, 106-112.

[21]. MEIER, O., and GREBER, U. F. (2003). Adenovirus endocytosis. J Gene Med 5, 451-462.

[22]. NOBS, L., BUCHEGGER, F., GURNY, R., and ALLEMANN, E. (2003). Surface modification of poly(lactic acid) nanoparticles by covalent attachment of thiol groups by means of three methods. Int J Pharm 250, 327-337.

[23]. NOBS, L., BUCHEGGER, F., GURNY, R., and ALLEMANN, E. (2004). Poly(lactic acid) nanoparticles labeled with biologically active Neutravidin for active targeting. Eur J Pharm Biopharm 58, 483-490.

[24]. NYANGUILE, O., DANCIK, C., BLAKEMORE, J., MULGREW, K., KALEKO, M., and STEVENSON, S. C. (2003). Synthesis of adenoviral targeting molecules by intein-mediated protein ligation. Gene Ther 10, 1362-1369.

[25]. OGAWARA, K, ROTS, M. G., KOK, R. J., MOORLAG, H. E., VAN LOENEN, A. M., MEIJER, D. K., HAISMA, H. J., and MOLEMA, G. (2004). A novel strategy to modify adenovirus tropism and enhance transgene delivery to activated vascular endothelial cells in vitro and in vivo. Hum Gene Ther 15, 433-443.

[26]. PANDORI, M., HOBSON, D., and SANO, T. (2002a). Adenovirus-microbead conjugates possess enhanced infectivity: a new strategy for localized gene delivery. Virology 299, 204-212.

[27]. PANDORI, M. W., HOBSON, D. A., OLEJNIK, J., KRZYMANSKA-OLEJNIK, E., ROTHSCHILD, K J., PALMER, A. A., PHILLIPS, T. J., and SANO, T. (2002b). Photochemical control of the infectivity of adenoviral vectors using a novel photocleavable biotinylation reagent. Chem Biol 9, 567-573.

[28]. PANDORI, M. W., and SANO, T. (2005). Chemically inactivated adenoviral vectors that can efficiently transduce target cells when delivered in the form of virus-microbead conjugates. Gene Ther 12, 521-533.

[29]. PERRIN, D. A., and ENGLISH, J. P. (1997). Polyglycolide and polylactide. In Handbook of Biodegradable Polymers. A. J. Domb, J. Kost, and D. M. Wiseman, eds. (Harwood Academic Publishers, Amsterdam) pp. 3-26.

[30]. QIANG, B., SEGEV, A., BELIARD, I., NILI, N., STRAUSS, B. H., and SEFTON, M. V. (2004). Poly(methylidene malonate 2.1.2) nanoparticles: a biocompatible polymer that enhances peri-adventitial adenoviral gene delivery. J Control Release 98, 447-455.

[31]. QUINTANAR-GUERRERO, D., ALLEMANN, E., FESSI, H., and DOELKER, E. (1998). Preparation techniques and mechanisms of formation of biodegradable nanoparticles from preformed polymers. Drug Dev Ind Pharm 24, 1113-1128.

[32]. ROSCA, I. D., WATARI, F., and UO, M. (2004). Microparticle formation and its mechanism in single and double emulsion solvent evaporation. J Control Release 99, 271-280.

[33]. SAITO, G., SWANSON, J. A., and LEE, K. D. (2003). Drug delivery strategy utilizing conjugation via reversible disulfide linkages: role and site of cellular reducing activities. Adv Drug Deliv Rev 55, 199-215.

[34]. THOMAS, C. E., BIRKETT, D., ANOZIE, I., CASTRO, M. G., and LOWENSTEIN, P. R. (2001). Acute direct adenoviral vector cytotoxicity and chronic, but not acute, inflammatory responses correlate with decreased vector-mediated transgene expression in the brain. Mol Ther 3, 36-46.

[35]. WICKHAM, T. J., ROELVINK, P. W., BROUGH, D. E., and KOVESDI, I. (1996). Adenovirus targeted to heparan-containing receptors increases its gene delivery efficiency to multiple cell types. Nat Biotechnol 14, 1570-1573.

[36]. WICKHAM, T. J., TZENG, E., SHEARS, L. L., 2ND, ROELVINK, P. W., LI, Y., LEE, G. M., BROUGH, D. E., LIZONOVA, A., and KOVESDI, I. (1997). Increased in vitro and in vivo gene transfer by adenovirus vectors containing chimeric fiber proteins. J Virol 71, 8221-8229.

[37]. XU, Z. L., MIZUGUCHI, H., SAKURAI, F., KOIZUMI, N., HOSONO, T., KAWABATA, K., WATANABE, Y., YAMAGUCHI, T., and HAYAKAWA, T. (2005). Approaches to improving the kinetics of adenovirus-delivered genes and gene products. Adv Drug Deliv Rev 57, 781-802.

[38]. YEI, S., MITTEREDER, N., WERT, S., WHITSETT, J. A., WILMOTT, R. W., and TRAPNELL, B. C. (1994). In vivo evaluation of the safety of adenovirus-mediated transfer of the human cystic fibrosis transmembrane conductance regulator cDNA to the lung. Hum Gene Ther 5, 731-744.

While the invention has been described in detail and with reference to specific examples thereof, it will be apparent to one skilled in the art that various changes and modifications can be made therein without departing from the spirit and scope thereof.

What is claimed is:

1. A composition comprising a monomolecular layer of a water-soluble photo-activatable polymer and a matrix having at least one carbon, wherein the photo-activatable polymer comprises (a) a photo-activatable group, wherein the photo-activatable group is adapted to be activated by an irradiation source and to form a covalent bond between the water-soluble photo-activatable polymer and a matrix having at least one carbon;

(b) a reactive group, wherein the reactive group is adapted to covalently react with a biomaterial;

(c) a hydrophilic group, wherein the hydrophilic group is present in an amount sufficient to make the water-soluble photo-activatable polymer soluble in water; and (d) a polymer precursor;

wherein the water-soluble polymer is represented by a formula:

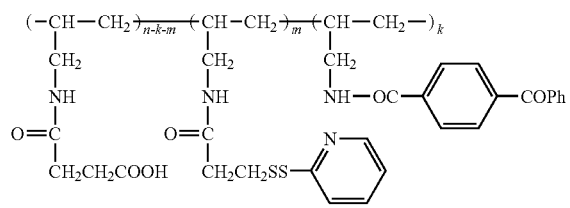

wherein n is 50 to 2000, k is 10 to 1000, and m is 10 to 1000; and wherein the matrix comprises a polymer or an organosilylated material, said polymer or organosilylated material comprising C—H bonds and said at least one carbon, and wherein the monomolecular layer is attached to the matrix by a covalent bond between the photo-activatable group and the at least one carbon.

2. The composition of claim 1, further comprising a biomaterial having a plurality of active groups, wherein the biomaterial is covalently attached to the monomolecular layer by covalent bonding between the active groups and reactive groups.

3. The composition of claim 2, wherein at least one of the active groups is a member selected from the group consisting of amine, carboxyl, hydroxyl, thiol, phenol, imidazole, and indole.

4. The composition of claim 2, wherein at least one of the active groups comprises thiol.

5. The composition of claim 2, wherein the covalently attached biomaterial is paclitaxel.

6. The composition of claim 2, wherein the biomaterial comprises a member selected from the group consisting of an antibody, a viral vector, a growth factor, a bioactive polypeptide, a polynucleotide coding for the bioactive polypeptide, a cell regulatory small molecule, a peptide, a protein, an oligonucleotide, a gene therapy agent, a gene transfection vector, a receptor, a cell, a drug delivering agent, nitric oxide, an antimicrobial agent, an antibiotic, an antimitotic, dimethyl sulfoxide, an antisecretory agent, an anti-cancer chemotherapeutic agent, steroidal and non-steroidal anti-inflammatories, hormones, an extracellular matrix, a free radical scavenger, an iron chelator, an antioxidant, an imaging agent, and a radiotherapeutic agent.

7. The composition of claim 6, wherein the biomaterial is at least one of an anti-knob antibody, an adenovirus, a D1 domain of the Coxsackie-adenovirus receptor, insulin, an angiogenic peptide, an antiangiogenic peptide, avidin, biotin, IgG, protein A, transferrin, and a receptor for transferrin.

8. The composition of claim 6, wherein the biomaterial comprises a drug.

9. The composition of claim 1, wherein the matrix is a member selected from a group consisting of poly(urethane), poly(ester), poly(ethyleneimine), poly(styrene), poly(amide), rubber, silicone rubber, poly(acrylonitrile), poly(acrylate), poly(methacrylate), poly(orthoester), poly(etherester), mixtures thereof and copolymers of corresponding monomers.

10. The composition of claim 9, wherein the matrix further comprises a magnetic field-responsive agent.

11. The composition of claim 9, wherein the matrix is a poly(ester) and said polyester is a poly(lactone) or a poly(alpha-hydroxy acid).

12. The composition of claim 9, wherein the matrix is a poly(ester) selected from the group consisting of poly(lactic acid), poly(glycolic acid), poly(lactide-co-glycolide), poly(ε-caprolactone) and poly(dioxanone).

13. The composition of claim 10, wherein the magnetic field-responsive agent is a superparamagnetic agent selected from the group consisting of magnetite and maghemite nanocrystals.

14. The composition of claim 1, wherein the matrix is an implantable device.

15. The composition of claim 14, wherein the implantable device comprises at least one member selected from the group consisting of poly(urethane), poly(ester), poly(ethyleneimine), poly(styrene), poly(amide), rubber, silicone rubber, poly(acrylonitrile), poly(acrylate), poly(methacrylate), poly(tetrafluoroethylene), organosilane, mixtures thereof and copolymers of corresponding monomers.

16. The composition of claim 15, wherein the matrix is a poly(ester) selected from the group consisting of, poly(lactic acid), poly(lactide-co-glycolide) and poly(ε-caprolactone).

17. The composition of claim 1, wherein the matrix is a particle having a diameter of about 5 nm to about 10 microns.

18. The composition of claim 17, wherein the particle further comprises a drug dissolved or dispersed in the matrix.

19. The composition of claim 17, wherein the particle further comprises a drug adsorbed to the surface thereof.

20. The composition of claim 19, wherein the drug is paclitaxel.

21. The composition of claim 17, wherein the particle comprises at least one member selected from the group consisting of poly(lactic acid), poly(glycolic acid), poly(lactide-co-glycolide), poly(ethyleneimine), poly(lactone), mixtures thereof and copolymers of corresponding monomers.

22. The composition of claim 21, wherein the particle comprises a poly(lactone) and the poly(lactone) is poly(ε-caprolactone).

23. The composition of claim 21, wherein the particle further comprises a biomaterial having a plurality of active groups, wherein the biomaterial is covalently attached to the monomolecular layer by covalent bonding between the active groups and reactive groups.

24. The composition of claim 23, wherein the biomaterial comprises a member selected from the group consisting of an antibody, a viral vector, a growth factor, a bioactive polypeptide, a polynucleotide coding for the bioactive polypeptide, a cell regulatory small molecule, a peptide, a protein, an oligonucleotide, a gene therapy agent, a gene transfection vector, a receptor, a cell, a drug delivering agent, nitric oxide, an antimicrobial agent, an antibiotic, an antimitotic, dimethyl sulfoxide, an antisecretory agent, an anti-cancer chemotherapeutic agent, steroidal and non-steroidal anti-inflammatories, hormones, an extracellular matrix, a free radical scavenger, an iron chelator, an antioxidant, an imaging agent, and a radiotherapeutic agent.

25. The composition of claim 24, wherein the biomaterial is at least one of an anti-knob antibody, an adenovirus, a D1 domain of the Coxsackie-adenovirus receptor, insulin, an angiogenic peptide, an antiangiogenic peptide, avidin, biotin, IgG, protein A, transferrin, and a receptor for transferrin.

26. The composition of claim 25, wherein the biomaterial is iNOS-AdV or GFP-AdV.

27. The composition of claim 24, wherein the biomaterial comprises a drug.

28. A method of making the composition of claim 1, the method comprising:
providing the matrix having at least one carbon;
providing an aqueous solution of the water-soluble photo-activatable polymer having the photo-activatable group and the reactive group;
contacting the matrix with the aqueous solution; and
photo-activating the photo-activatable group by irradiation to covalently attach the water-soluble polymer via the photo-activatable group to the matrix and thereby forming the monomolecular layer of the composition.

29. The method of claim 28, wherein the irradiation is performed at a wavelength from about 190 to about 900 nm.

30. The method of claim 29, wherein the irradiation is performed at a wavelength of 280 to 360 nm.

31. The method of claim 28, further comprising:
providing a biomaterial having a plurality of active groups; and
reacting the plurality of active groups with the water-soluble photo-activatable polymer to covalently attach the biomaterial to the matrix.

32. The method of claim 28, wherein the matrix is an implantable device.

33. A method for delivery of a biomaterial to a cell, the method comprising:
contacting the composition of claim 1 with a biomaterial having a plurality of active groups under conditions sufficient to attach the biomaterial to the monomolecular layer by covalent bonding between the active groups and the reactive groups; and
administering the matrix to the cell and thereby delivering the biomaterial.

34. The method of claim 33, wherein the biomaterial is at least one of a protein, a D1 domain of the Coxsackie-adenovirus receptor, an adenovirus, or an antibody specifically bound to a nucleic acid.

35. The method of claim 33, wherein the matrix is an implantable device.

36. The method of claim 33, wherein the matrix is a particle having a diameter of about 5 nm to about 10 microns.

37. The method of claim 36, wherein the biomaterial is iNOS-AdV or GFP-AdV.

38. A method for delivery of a biomaterial to a cell or a tissue, the method comprising:
providing a bioactive magnetic particle comprising (1) the composition of claim 2, wherein the matrix is in a shape of a particle having a diameter of about 5 nm to about 10 microns, and (2) a magnetic field-responsive agent associated with the matrix;
providing an implant comprising a magnetic surface to the cell or the tissue;
administering the bioactive magnetic particle to the cell or the tissue; and
capturing the bioactive magnetic particle onto the magnetic surface, and thereby delivering the biomaterial.

39. The method of claim 38, wherein delivery of the biomaterial to a cell or a tissue comprises manipulating at least one of a particle diameter, proximity of an external magnetic field, a degree of surface magnetization of the implant, and a time interval for capturing the particle onto the magnetic surface.

40. The method of claim 38, wherein the implant is a stent.

41. The method of claim 40, wherein the stent is in an artery.

42. The method of claim 38, wherein the step of capturing the bioactive magnetic particle onto the magnetic surface, and thereby delivering the biomaterial, comprises the step of applying a uniform magnetic field to generate a magnetic field gradient in proximity to the implant.

43. The method of claim 42, wherein the uniform magnetic field is provided by an electromagnet.

44. The method of claim 42, comprising the step of administering additional bioactive magnetic particles and reapplying the uniform magnetic field to deliver additional particles onto the magnetic surface of the implant.

45. The composition of claim 18, wherein the drug is paclitaxel.

* * * * *